(12) United States Patent
Sun et al.

(10) Patent No.: US 10,441,588 B2
(45) Date of Patent: *Oct. 15, 2019

(54) METHODS AND COMPOSITIONS FOR TREATING BACTERIAL INFECTION

(71) Applicants: Curators of the University of Missouri, Columbia, MO (US); Nanova, Inc., Columbia, MO (US)

(72) Inventors: Hongmin Sun, Columbia, MO (US); David W. Anderson, Columbia, MO (US); Feng Qi, Columbia, MO (US)

(73) Assignees: Curators of the University of Missouri, Columbia, MO (US); Nanova, Inc., Columbia, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/711,648

(22) Filed: Sep. 21, 2017

(65) Prior Publication Data

US 2018/0042928 A1  Feb. 15, 2018

Related U.S. Application Data

(63) Continuation-in-part of application No. 15/335,156, filed on Oct. 26, 2016, now Pat. No. 9,814,719, which is a continuation-in-part of application No. 14/397,798, filed as application No. PCT/US2013/039257 on May 2, 2013, now Pat. No. 9,504,688.

(60) Provisional application No. 61/641,590, filed on May 2, 2012.

(51) Int. Cl.
| | | |
|---|---|---|
| A61K 31/517 | (2006.01) | |
| A61K 9/00 | (2006.01) | |
| A61K 47/06 | (2006.01) | |
| A61K 31/5377 | (2006.01) | |
| A61K 45/06 | (2006.01) | |
| A61K 31/527 | (2006.01) | |
| A61K 31/505 | (2006.01) | |
| A61K 47/44 | (2017.01) | |
| A61K 31/519 | (2006.01) | |
| A61L 27/54 | (2006.01) | |
| A61L 29/16 | (2006.01) | |
| A61L 31/16 | (2006.01) | |

(52) U.S. Cl.
CPC .......... *A61K 31/517* (2013.01); *A61K 9/0014* (2013.01); *A61K 31/505* (2013.01); *A61K 31/519* (2013.01); *A61K 31/527* (2013.01); *A61K 31/5377* (2013.01); *A61K 45/06* (2013.01); *A61K 47/06* (2013.01); *A61K 47/44* (2013.01); *A61L 27/54* (2013.01); *A61L 29/16* (2013.01); *A61L 31/16* (2013.01); *A61L 2300/404* (2013.01); *Y02A 50/473* (2018.01)

(58) Field of Classification Search
CPC .................................................... C07D 241/08
See application file for complete search history.

(56) References Cited

U.S. PATENT DOCUMENTS

| | | | |
|---|---|---|---|
| 4,209,621 A | 6/1980 | Dusza et al. | |
| 5,298,481 A | 3/1994 | Tice | |
| 8,501,722 B2* | 8/2013 | Ginsburg | G01B 11/0625 506/2 |
| 9,504,688 B2* | 11/2016 | Ginsburg | A61K 31/505 |
| 9,814,719 B2* | 11/2017 | Sun | A61K 31/517 |
| 2003/0191144 A1 | 10/2003 | Connop | |
| 2009/0182140 A1 | 7/2009 | Furukubo et al. | |
| 2010/0331351 A1* | 12/2010 | Ginsburg | G01B 11/0625 514/267 |

OTHER PUBLICATIONS

Markosyan, et al, Transglycosylation of benzo[h]quinazolines, Applied Biochemistry and Microbiology (2009), 45(2), 130-136. (Year: 2009).*
Agarwal, et al., Medical significance and management of staphylococcal biofilm. FEMS Immunol Med Microbiol, 2010, vol. 58, pp. 147-160.
Alanis, "Resistance to antibiotics: are we in the post-antibiotic era?", Arch Med Res., 2005, vol. 36, No. 6, pp. 697-705.
Bax, et al., The millennium bugs—the need for and development of new antibacterials, Int J Antimicrob Agents, 2000, vol. 16, No. 1, pp. 51-59.
Caratoa, et al., Synthesis of 6- and 7-acyl-4H-benzothiazin-3-ones, Tetrahedron, Sep. 18, 2006, vol. 62, No. 38, pp. 9054-9058.
Chambers & Deleo FR, Waves of resistance: *Staphylococcus aureus* in the antibiotic era, Nat Rev Microbiol., 2009, vol. 7, No. 9, pp. 629-641.
Costerton, et al., Bacterial biofilms: a common cause of persistent infections, Science, 1999, vol. 284, No. 5418, pp. 1318-1322.
Donlan, Biofilms and Device-Associated Infections, Emerging Infectious Diseases, Mar.-Apr. 2001, vol. 7, No. 2, pp. 277-281.
Fux, et al., Survival strategies of infectious biofilms, Trends Microbiol, 2005, vol. 13, No. 1, pp. 34-40.
Gao, et al.. "An efficient synthesis of 5,6-dihydrobenzo[h]quinazoline derivatives under solvent-free conditions" Journal of Heterocyclic Chemistry Mar. 2010, vol. 47, No. 2, pp. 358-362.
Grundmann, et al., "Emergence and resurgence of meticillin-resistant *Staphylococcus aureus* as a public-health threat." Lancet., 2006; vol. 368, No. 9538, pp. 874-885.
Klevens, et al., "Invasive methicillin-resistant *Staphylococcus aureus* infections in the United States." JAMA, 2007, vol. 298, No. 15, pp. 1763-1771.

(Continued)

*Primary Examiner* — Erich A Leeser
(74) *Attorney, Agent, or Firm* — Stinson LLP

(57) ABSTRACT

The present disclosure relates to chemical compounds, methods for their discovery, and their therapeutic and research use. In particular, the present disclosure provides compounds as therapeutic agents against bacterial infections (e.g., biofilms). The present disclosure also provides topical formulations for use in methods for treating bacterial infections.

8 Claims, 25 Drawing Sheets
(13 of 25 Drawing Sheet(s) Filed in Color)

(56) References Cited

OTHER PUBLICATIONS

Life Sciences Institute, University of Michigan, LSI Innovative Partnership Year-One Report, 2009-2010.

Lowy, et al., "Staphylococcus aureus infections." N Engl J Med., 1998, vol. 339, No. 8, pp. 520-532.

Ma, et al., "Novel inhibitors of Staphylococcus aureus virulence gene expression and biofilm formation." PLoS One, 2012, vol. 7, No. 10, pp. e47255.

Maki, et al., "The risk of bloodstream infection in adults with different intravascular devices: a systematic review of 200 published prospective studies." Mayo Clin Proc., 2006, vol. 81, No. 9, pp. 1159-1171.

Martinez & Baquero, "Interactions among strategies associated with bacterial infection: pathogenicity, epidemicity, and antibiotic resistance." Clin Microbiol Rev. 2002, vol. 15, No. 4, pp. 647-679.

Norrby, et al., "Lack of development of new antimicrobial drugs: a potential serious threat to public health." Lancet Infect Dis. 2005, vol. 5, No. 2, pp. 115-119.

Otto, "Looking toward basic science for potential drug discovery targets against community-associated MRSA" Med Res Rev. 2010, vol. 30, No. 1, pp. 1-22.

Otto, "Staphylococcal Biofilms" Cliff Top MicrobiolImmunol. 2008; vol. 322, pp. 207-228.

Schiano Moriello et al., "Development of the first potential covalent inhibitors of anandamide cellular uptake." J Med Chem. 2006, vol. 49, No. 7, pp. 320-332.

Silver, "Multi-targeting by monotherapeutic antibacterials." Nat Rev Drug Discov., 2007, vol. 6, No. 1, pp. 41-55.

Stewart & Costerton, "Antibiotic resistance of bacteria in biofilms." Lancet, 2001, vol. 358, No. 9276, pp. 135-138.

Sun, et al., "Inhibitor of streptokinase gene expression improves survival after group A Streptococcus infection in mice." Proc Natl Acad Sci USA, 2012, vol. 108, No. 9, pp. 3469-3474.

Uckay, et al., "Foreign body infections due to Staphylococcus epidermidis." Ann Med. 2009, vol. 41, No. 2, pp. 109-119.

Yestrepsky, et al., "Novel inhibitors of bacterial virulence: development of 5,6-dihydrobenzo[h]quinazolin-4(3H)-ones for the inhibition of group A streptococcal streptokinase expression." Bioorg Med Chem., 2013, vol. 21, No. 7, pp. 1880-1897.

Moriello, et al., Development of the First Potential Covalent Inhibitors of Anandaminde Cellular Uptake, J. Med. Chem, 2006, vol. 49, No. 7, pp. 2320-2332.

Osaki, et al., Controlled Drug Release through a Plasma Polymerized Tetramethylcyclo-tetrasiloxane Coating Barrier, Journal of Biomaterials Science, Polymer Edition, vol. 23, 2012, pp. 486-496.

Antoci, et al., The inhibition of Staphylococcus epidermidis biofilm formation by vancomycin-modified titanium alloy and implications for the treatment of periprosthetic infection, Biomaterials, 2008, vol. 29, No. 35, pp. 4684-4690.

Hume EBS, Biomaterials vol. 25, 2004, pp. 5023-5030.

Markosyan, et al., Transglycosylation of benzo[h]quinazolines, Applied Biochemistry and Microbiology, vol. 45, No. 2, pp. 130-136.

* cited by examiner

S aureus RN6390B
S epidermis

S aureus RN6390B
S epidermis

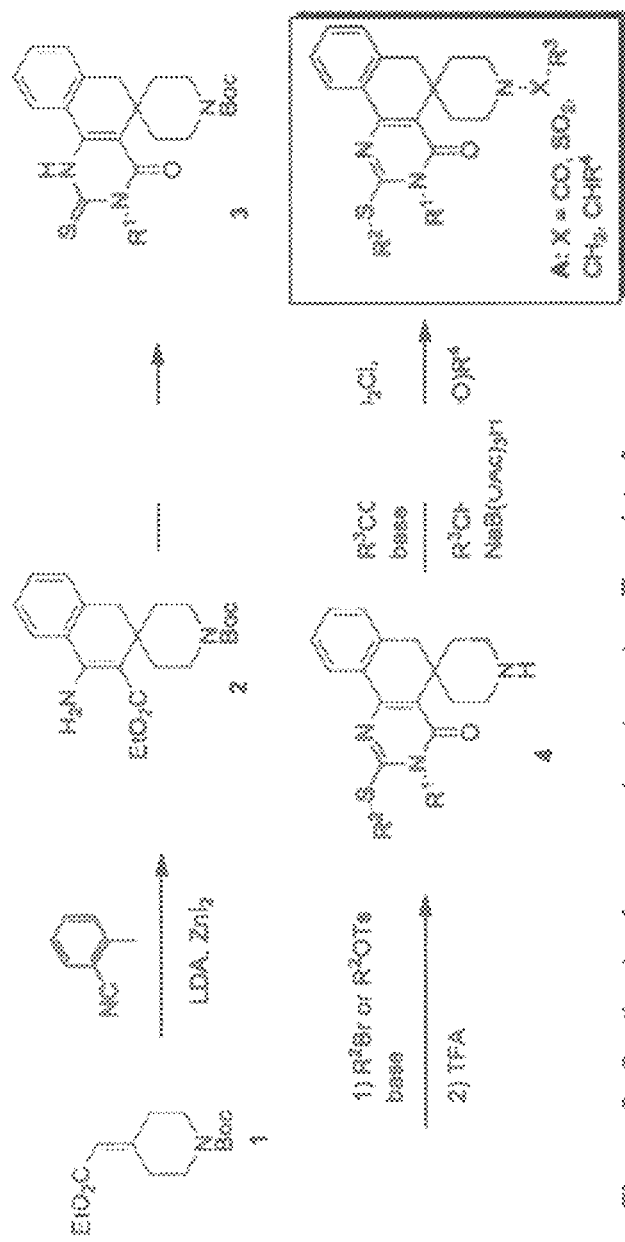
Figure 6. Synthesis of new analogs based on Template A.

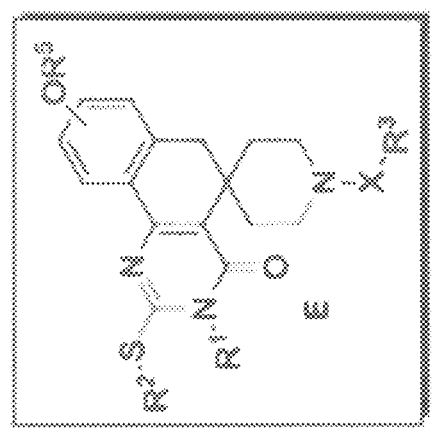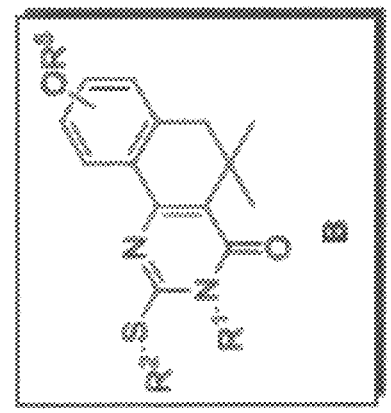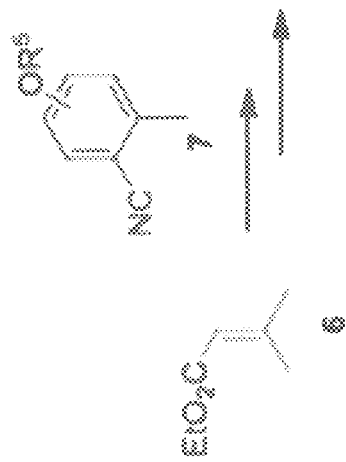
Figure 7

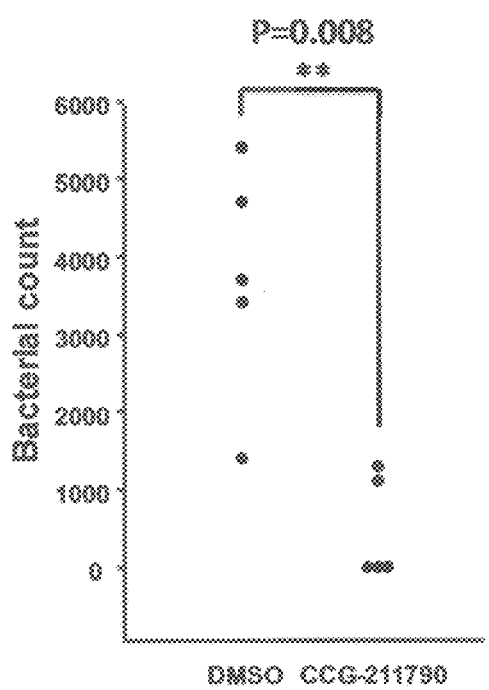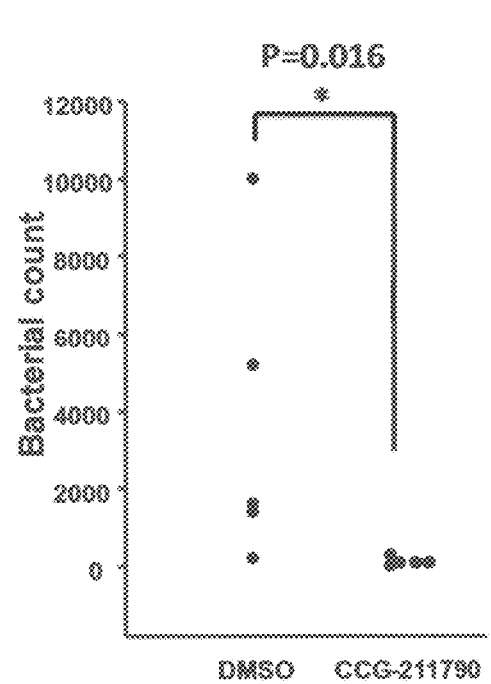

0 µM  5 µM  10 µM  20 µM  30 µM

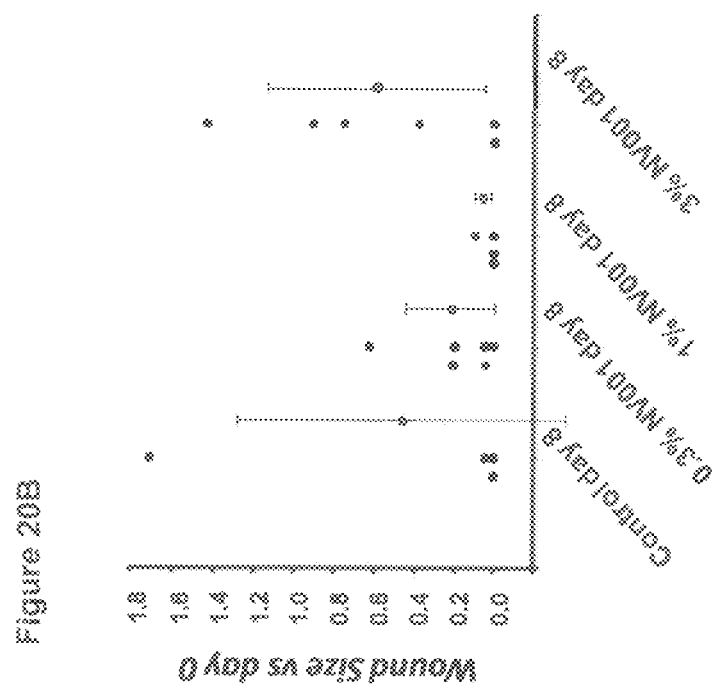
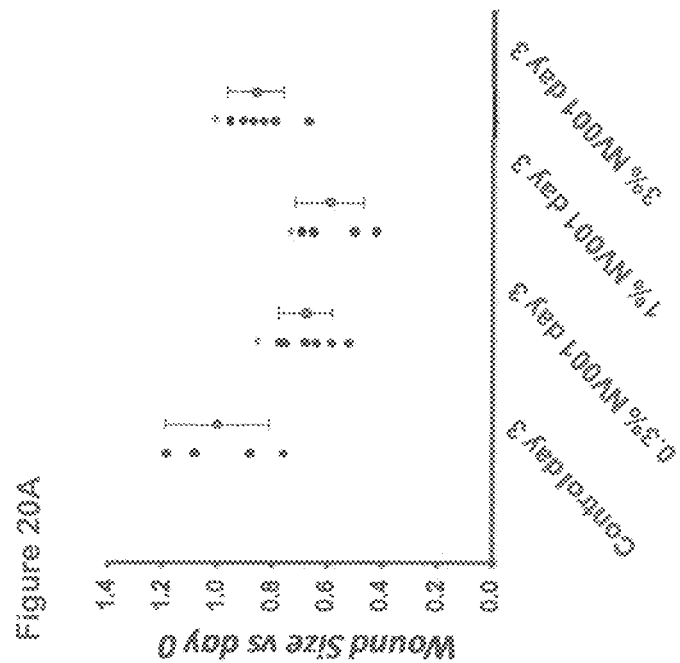
Figure 20A
Figure 20B

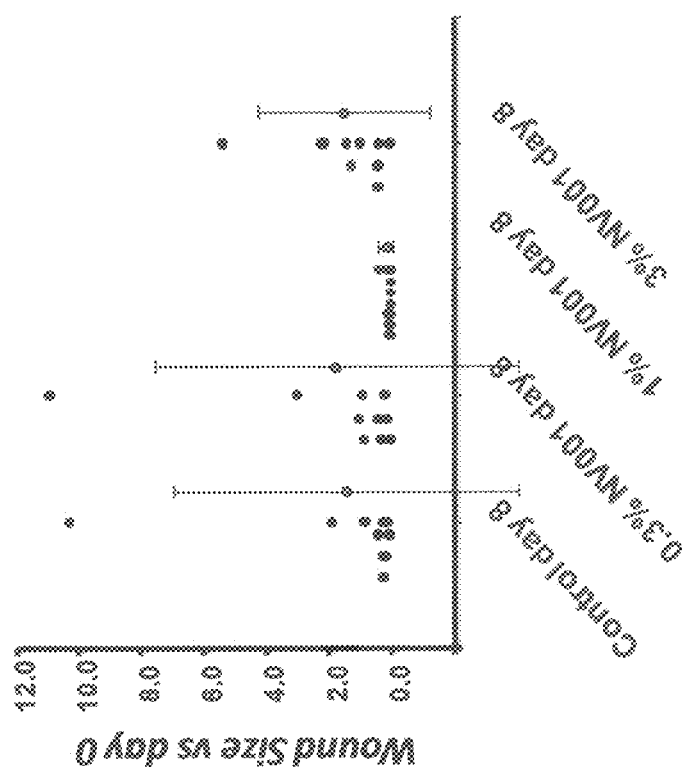
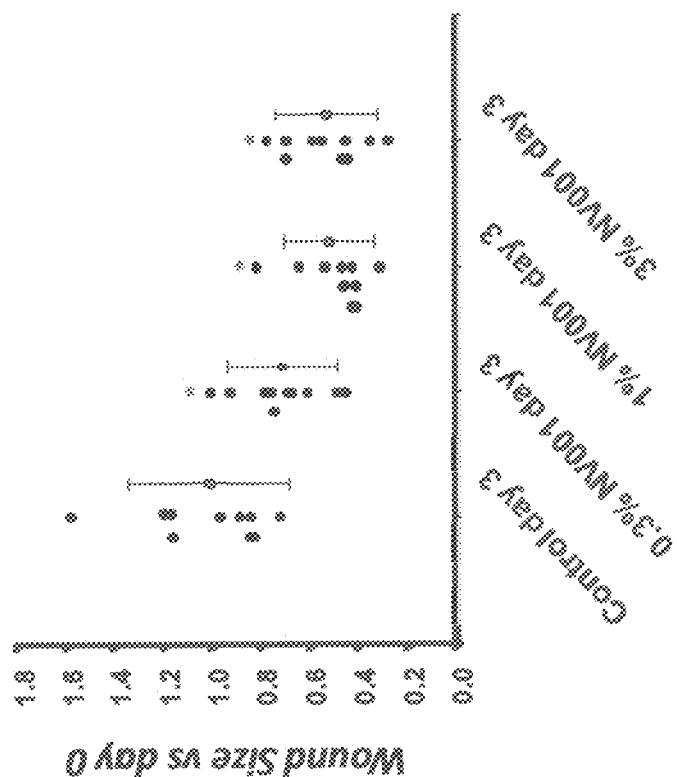

METHODS AND COMPOSITIONS FOR TREATING BACTERIAL INFECTION

This continuation in-part application claims priority to U.S. patent application Ser. No. 15/335,156, filed on Oct. 26, 2016, which is a continuation in-part application to U.S. patent application Ser. No. 14/397,798, filed on Oct. 29, 2014, which is a national phase application under 35 U.S.C. § 371 of PCT International Application No. PCT/US2013/039257, filed May 2, 2013, which claims priority to U.S. Provisional Patent Application No. 61/641,590, filed May 2, 2012, each of which is hereby incorporated by reference in its entirety.

STATEMENT REGARDING FEDERALLY SPONSORED RESEARCH OR DEVELOPMENT

This invention was made with government support under grant number PO1 HL 057346 awarded by the National Institutes of Health. The government has certain rights in the invention.

FIELD OF THE DISCLOSURE

The present disclosure relates to chemical compounds and methods for their therapeutic use. In particular, the present disclosure relates to compounds and methods for their therapeutic use for treating bacterial infections.

BACKGROUND OF THE DISCLOSURE

The prevalence of antibiotic resistance in bacteria is becoming one of the leading public health threats. Current antibiotics interfere with the critical biological processes of the pathogens and cause death or growth arrest of the bacteria. As a result, antibiotic therapy exerts a strong selective pressure to favor emergence of antibiotic resistant strains. In order to circumvent this serious problem, alternative antimicrobial reagents are needed that suppress the virulence of the pathogens without generating strong selection for antibiotic resistance.

Bacteria can develop biofilm on a submerged surface. Bacteria in biofilm behave differently from planktonic bacteria, especially in term of their response to antibiotic treatment (Donlan, 2001. *Emerg. Infect. Dis.* 7:277-281). Biofilm formation on or within indwelling medical devices such as catheters, mechanical heart valves, pacemakers, prosthetic joints, and contact lenses pose a critical problem for medical care. Both gram-negative and gram-positive bacteria can form biofilms on indwelling medical devices. The most common biofilm-forming bacteria include *Enterococcus faecalis, Staphylococcus aureus, Staphylococcus epidermidis, Streptococcus viridans, Escherichia coli, Klebsiella pneumoniae, Proteus mirabilis*, and *Pseudomonas aeruginosa* (Donlan, 2001, supra).

Among these biofilm-forming bacteria, *S. aureus* and *S. epidermidis* are most commonly found on cardiovascular devices (Otto, 2008. Staphylococcal biofilms. *Curr. Top. Microbiol. Immunol.* 322:207-228; Otto, M. 2009. *Med. Res. Rev.* 1-22). It was estimated that *S. aureus* and *S. epidermidis* caused about 40-50% of prosthetic heart valve infections, and 50-70% catheter biofilm infections (Agarwal et al., *FEMS Immunol. Med. Microbiol.* 58:147-160). 250,000-500,000 primary blood stream infections resulted from the 150 million intravascular devices implanted in the USA annually. Each episode of these infections can increase health care cost by $4,000 to $56,000 (Maki et al., 2006. *Mayo Clin. Proc.* 81:1159-1171; Uckay et al., 2009. *Ann. Med.* 41:109-119). Approximately 87% of blood stream infections were caused by staphylococci (Agarwal et al., 2010; supra). Taken together, *S. aureus* and *S. epidermidis* in biofilm exert a staggering burden on the healthcare system.

*Staphylococcus aureus* is a major human pathogen, and it is estimated that approximately 30% of humans are asymptomatic nasal carriers (Chambers and DeLeo 2009. *Nat. Rev. Microbiol.* 7:629-641). *S. aureus* causes skin, soft tissue, respiratory, bone, joint and endovascular diseases. Life threatening cases caused by *S. aureus* include bacteremia, endocarditis, sepsis and toxic shock syndrome (Lowy 1998. *N. Engl. J. Med.* 339:520-532). Antibiotic resistance in *S. aureus* is increasingly becoming an urgent medical problem. The methicillin resistance in *S. aureus* is approaching epidemic level (Chambers and DeLeo, supra; Grundmann et al., 2006. *Lancet* 368:874-885). It was estimated that 94,360 invasive MRSA infections occurred in the US in 2005, and these infections were associated with death in 18,650 cases (Klevens et al., 2007. *JAMA* 298:1763-1771). Although *S. epidermidis* is part of the normal human epithelial bacterial flora, it can cause infection when skin or mucous membrane is injured. Biofilm formation on implanted indwelling medical devices is the major manifestation of *S. epidermidis* pathogenesis (Otto et al., 2008; supra).

Biofilm-associated bacteria are particularly resistant to antibiotic treatment compared to planktonic organisms, probably due to the unique structure of biofilm that prevents antibiotics from reaching the bacteria, or the altered microenvironment within the biofilm that could inactivate antibiotics (Otto et al., 2008; supra). Furthermore, antibiotics mainly target active cell processes, leading to limited efficacy against bacteria in biofilm which are different from planktonic bacteria physiologically. Depletion of nutrition and accumulation of waste within biofilm could induce bacteria into a slow-growing or starved state resistant to antibiotics. Additionally, some bacteria may adopt a distinct biofilm phenotype in response to growing on surfaces which also decreases their sensitivity to antibiotics (Otto et al., 2008; supra; Costerton et al., 1999. *Science* 284:1318-1322; Fux et al., 2005. *Trends Microbial.* 13:34-40; Stewart et al., 2001. *Lancet* 358:135-138)

In addition to the difficulty of treating biofilm with conventional antibiotic therapy, treating biofilm is further complicated by the rising antibiotic resistance among *staphylococcus*. Antibiotics target a small set of proteins essential for bacterial survival, such as cell wall formation or synthesis of bacterial DNA, RNA, lipid and protein. As a result, antibiotic resistant strains have been favored by selective pressure (Martinez and Baquero, 2002. *Clin. Microbial. Rev.* 15:647-679). Antibiotic resistance in major human pathogens has become a serious public health burden.

Collectively, these factors indicate that novel therapeutic strategies beyond treatment with conventional bactericidal antibiotics are needed to address the morbidity and mortality resulting from biofilm formation.

SUMMARY

The present disclosure relates to chemical compounds, methods for their discovery, and their therapeutic and research use. In particular, the present disclosure provides compounds as therapeutic agents against bacterial infections.

For example, embodiments of the present disclosure provide a composition, comprising: a compound having the structure of Formula I, II, III or IV

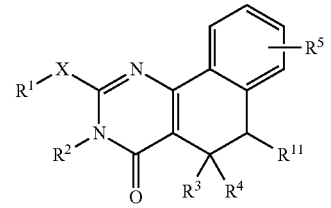

I

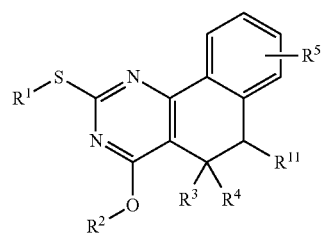

II

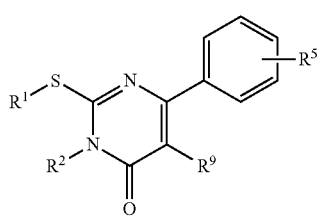

III

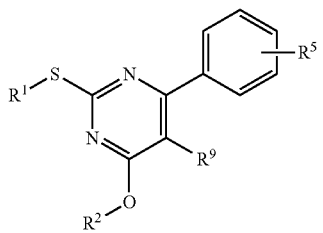

IV wherein X is S, NH, or O; $R^1$ and $R^2$ are, independently, a C1-C8 alkyl or alkenyl or cycloalkyl, optionally substituted with F, CN, $OR^6$, $NR^6_2$, $COR^6$, $CO_2R^6$, $CONHR^6$, aryl or heteroaryl, wherein one or more alkyl carbons may be replaced by O; $R^3$ and $R^4$ are independently H, joined in a cycloalkyl ring of 3-7 carbons wherein at least one ring $CH_2$ is replaced by O or N-G; G is H, C(=O)$R^6$, $SO_2R^6$ or C(=O)$OR^6$; $R^5$ is H, C1-C6 alkyl, CN, $OR^6$, $NR^6_2$, $COR^6$, $CO_2R^6$, $CONHR^6$, aryl, heteroaryl, $SO_2R^6$, $NHCOR^6$, $SO_2NHR^6$, or $OCOR^6$; $R^6$ is H, C1-C6 alkyl, C0-C3 alkyl-aryl, or C0-C3 alkyl-heteroaryl, all optionally substituted; $R^7$ and $R^8$ are a C1-C6 alkyl, or joined in a cycloalkyl ring of 3-7 carbons, wherein one of the ring $CH_2$ groups may be replaced by O or N-G; $R^9$ is C1-C5 alkyl; $R^{10}$ is a C2-C8 alkyl or alkenyl or cycloalkyl, optionally substituted with F, CN, $OR^6$, $NR^6_2$, $CO_2R^6$, $CONHR^6$, aryl or heteroaryl, wherein one or more alkyl carbons may be replaced by O; and R11 is H or a C1 alkyl. In some embodiments, the compound is, for example,

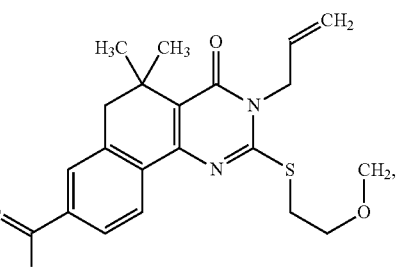

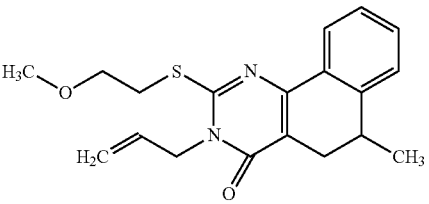

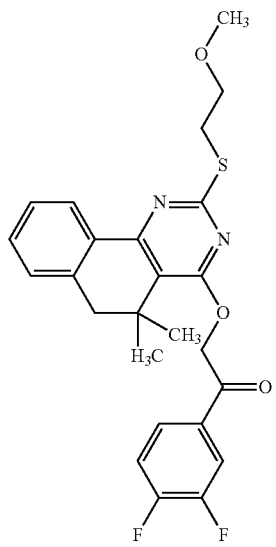

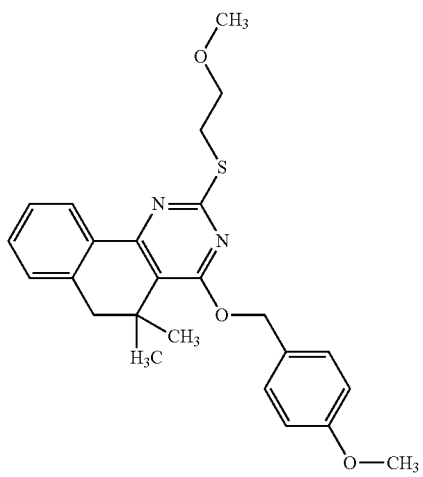

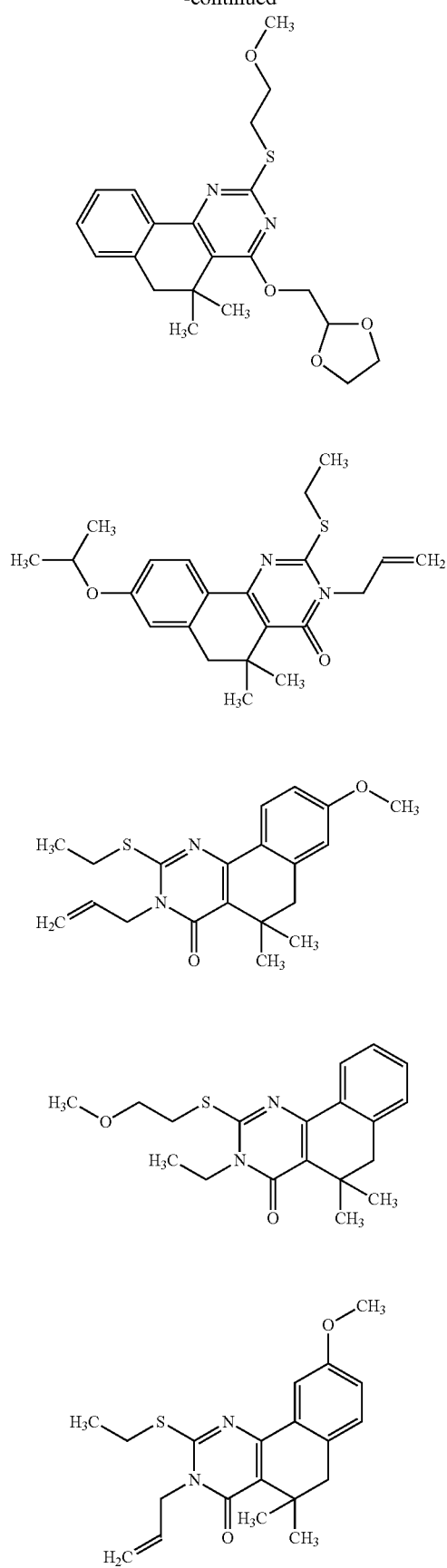
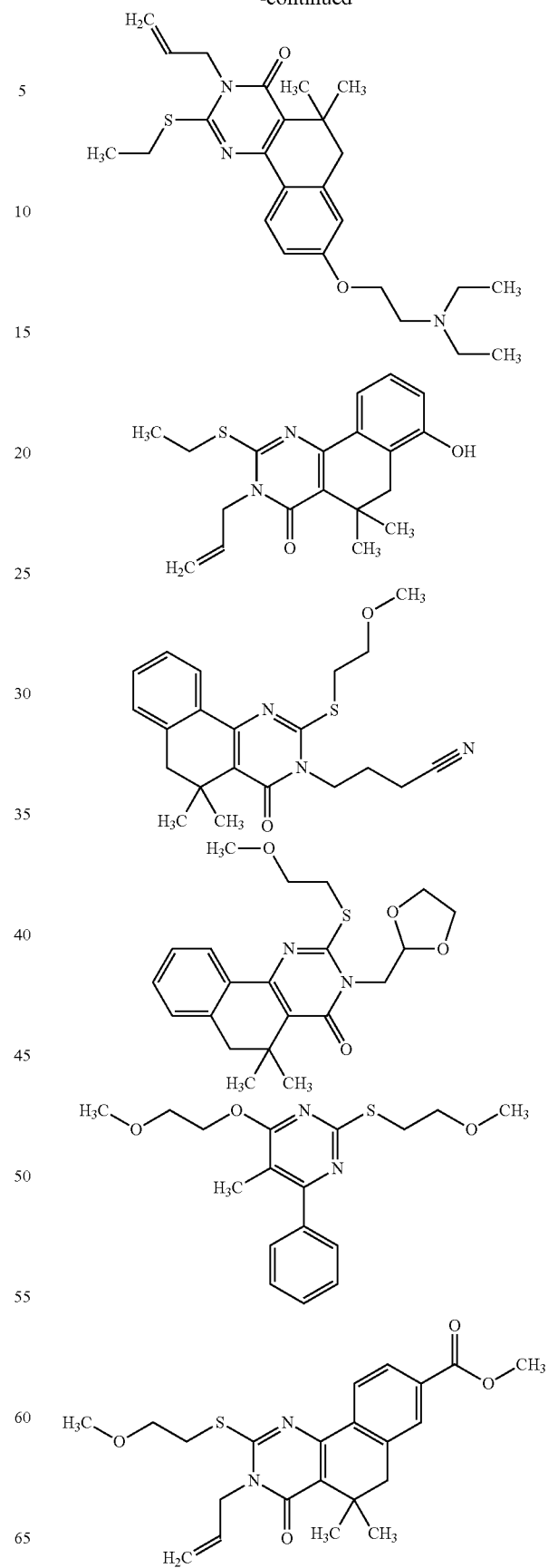

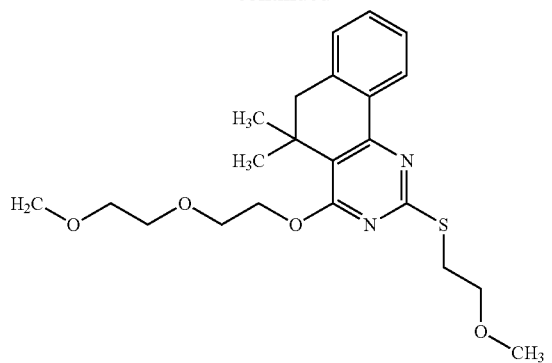
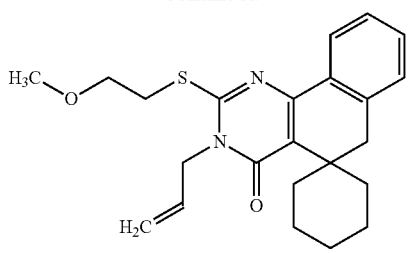
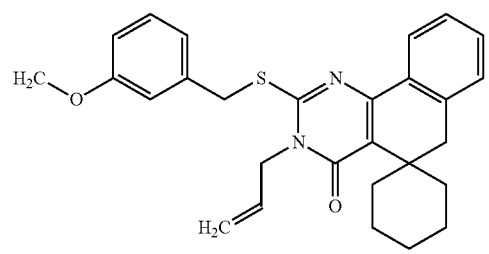
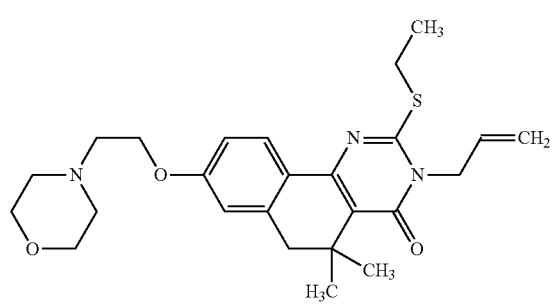
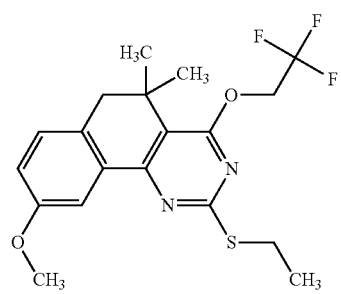
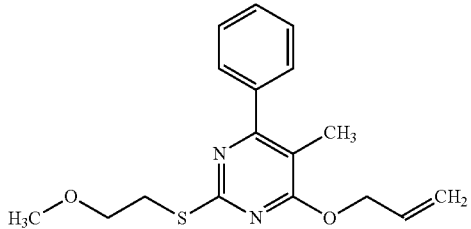
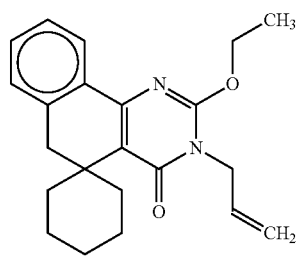
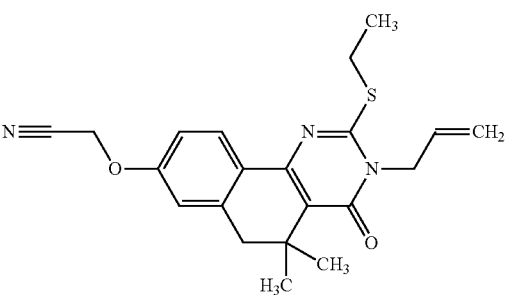
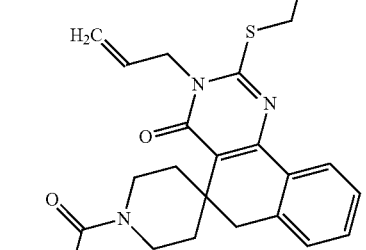
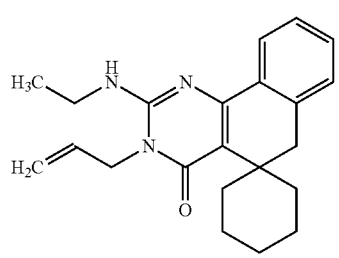

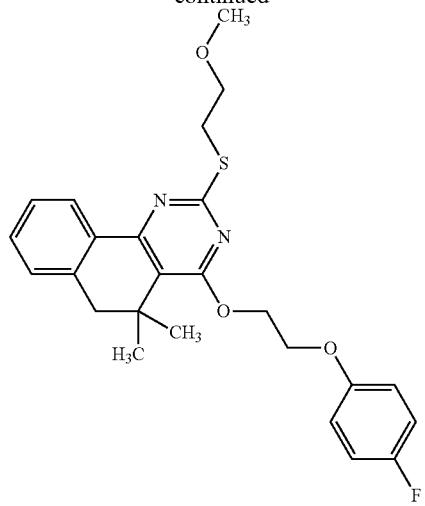
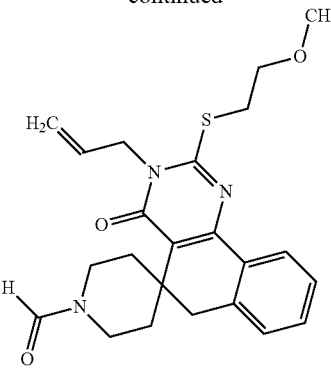
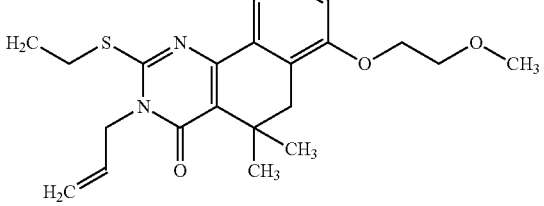
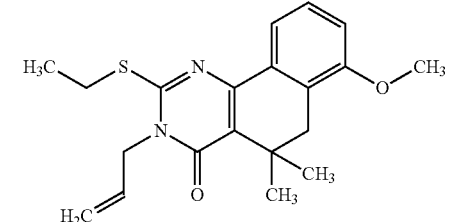
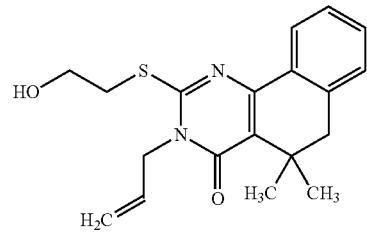
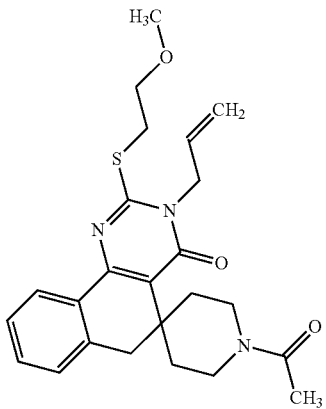
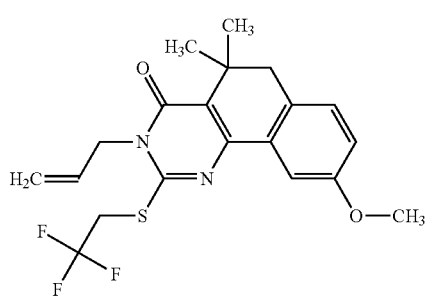
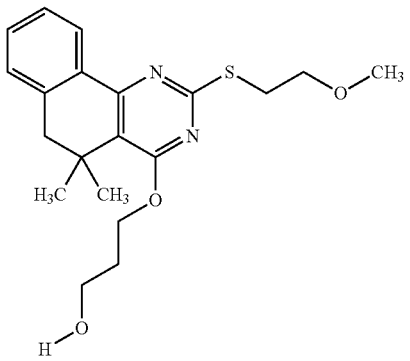

-continued
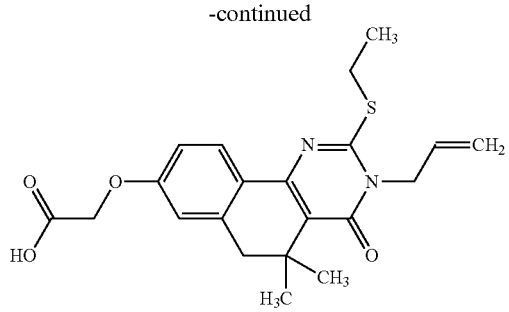
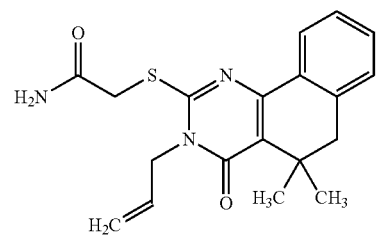
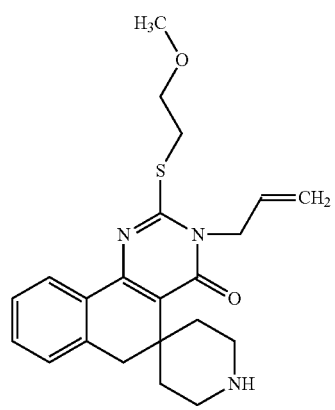
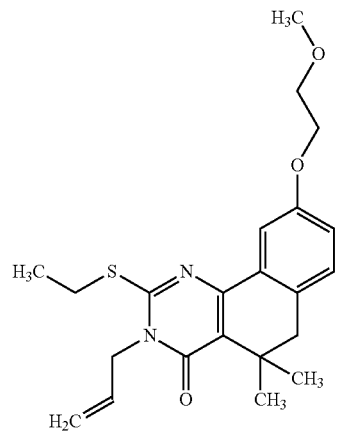
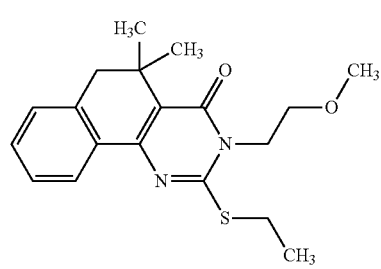
-continued
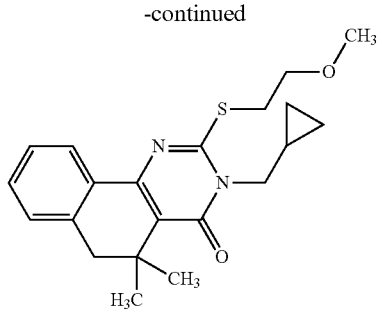
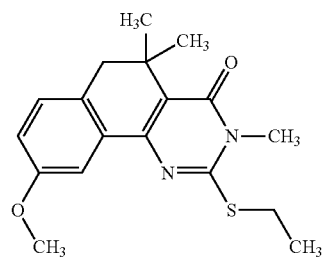
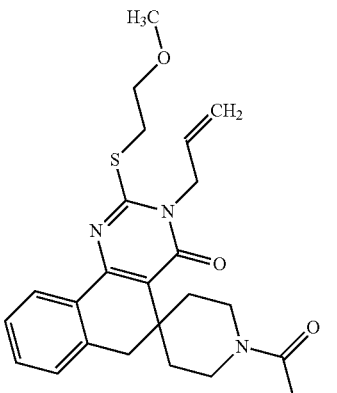
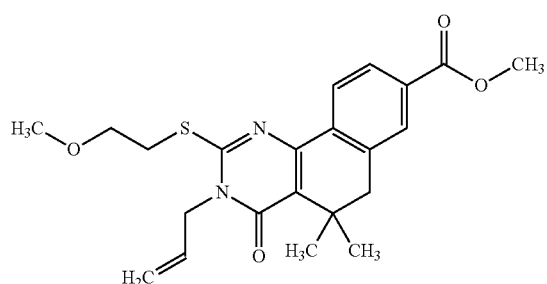
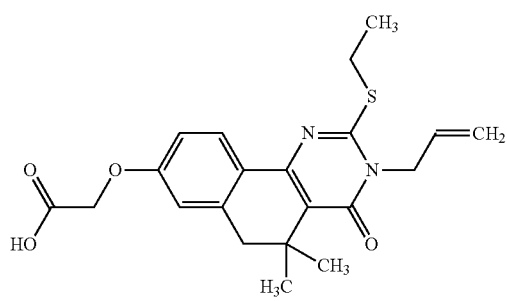
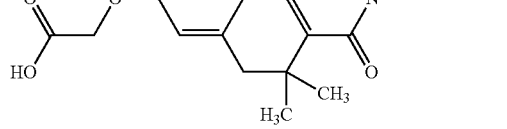

-continued
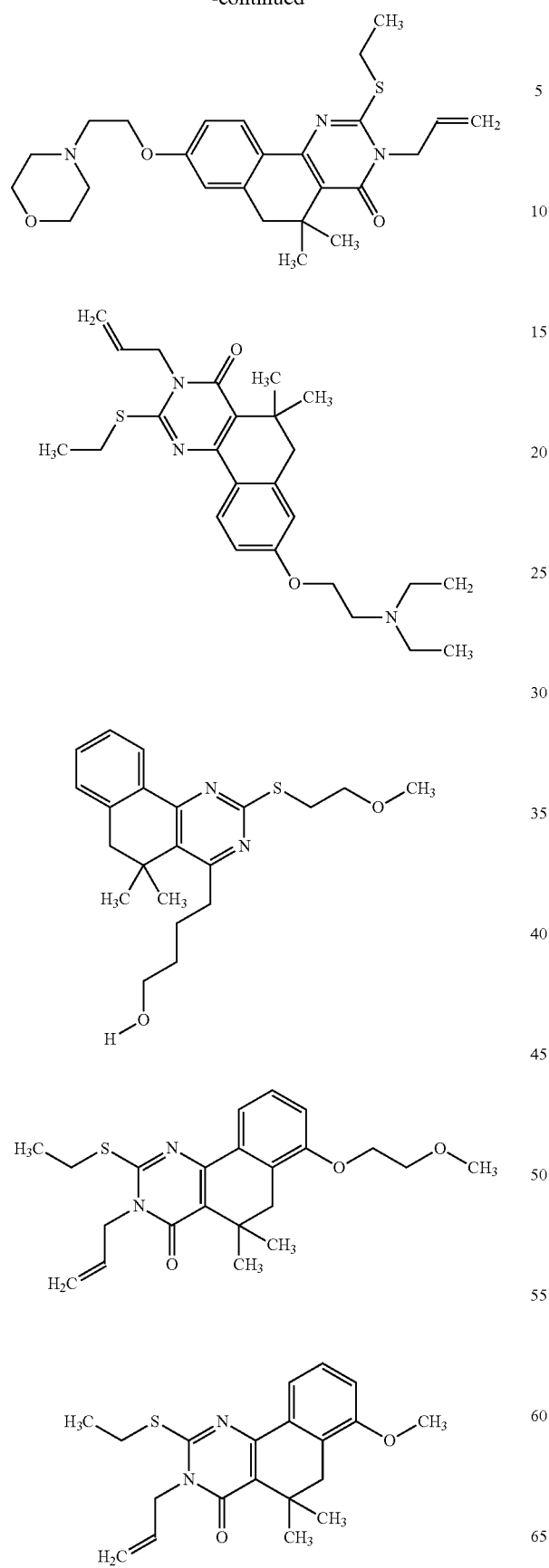
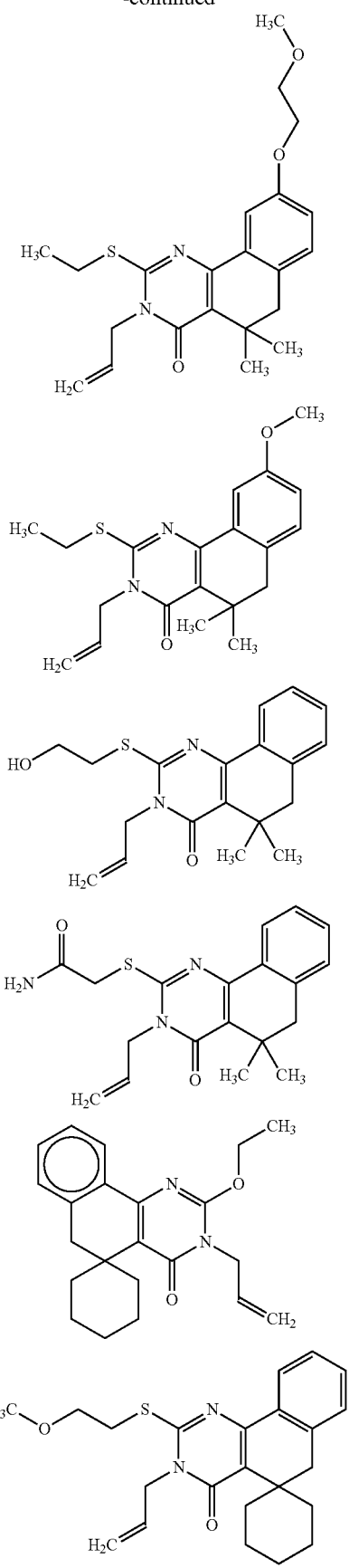

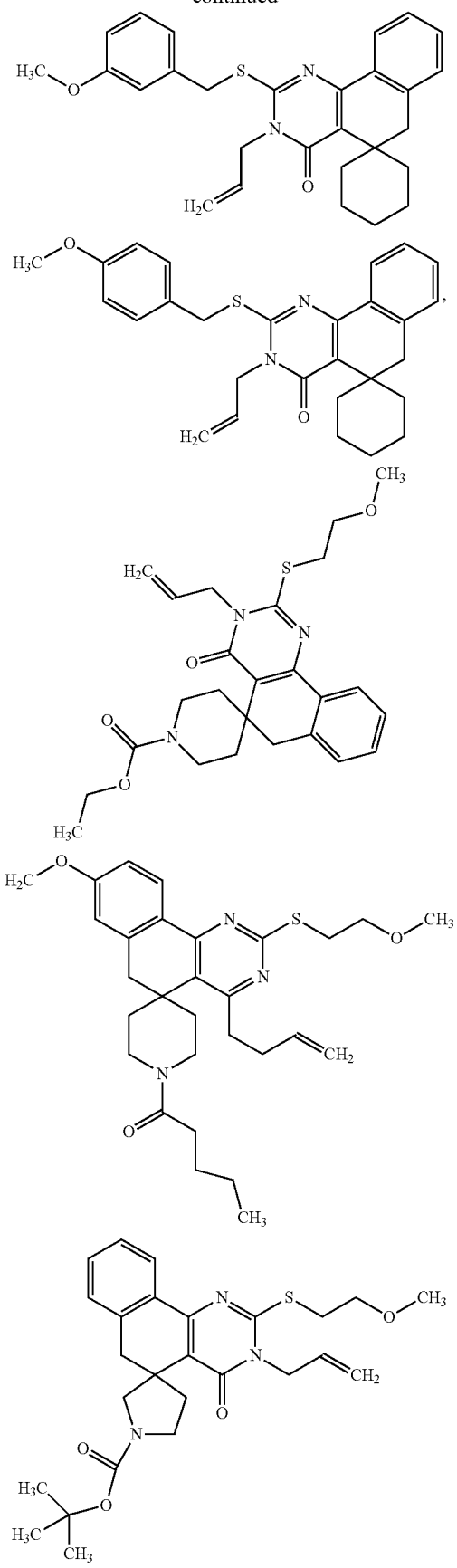

17
-continued
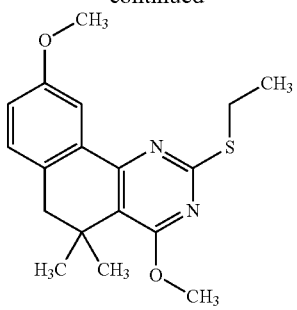
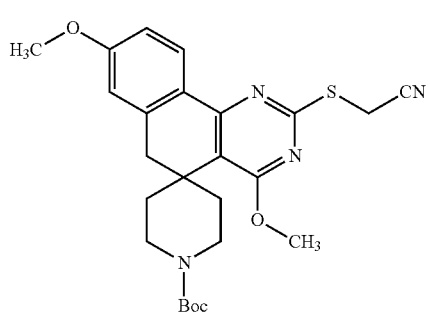
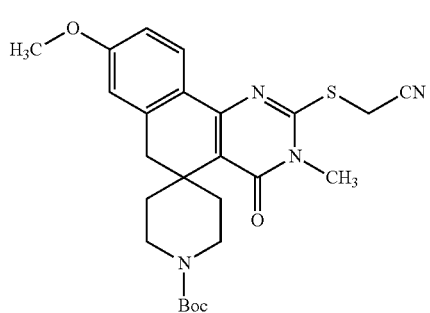
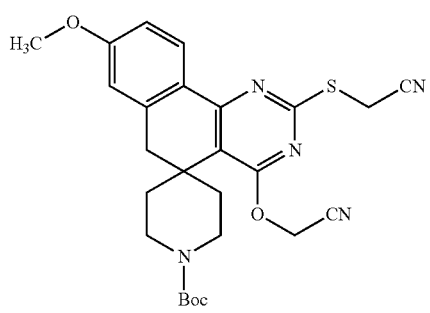
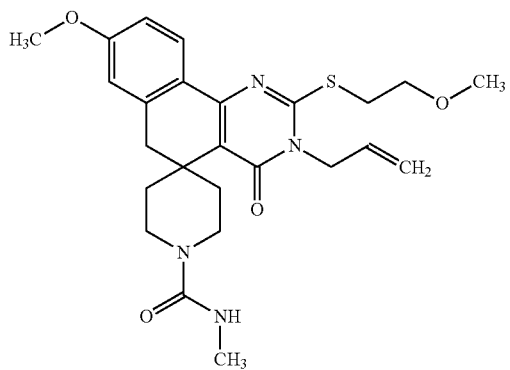
18
-continued
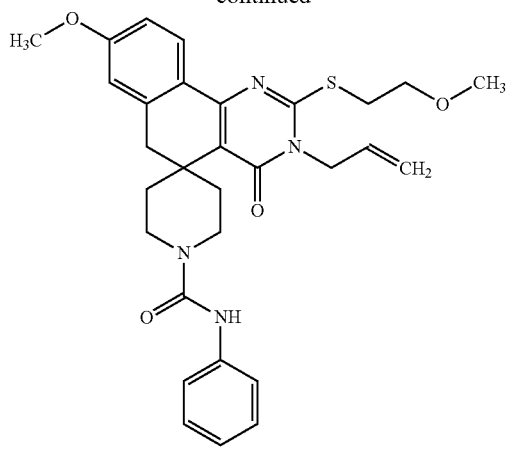
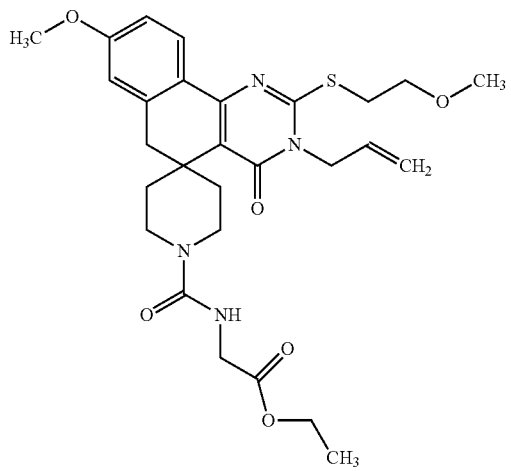
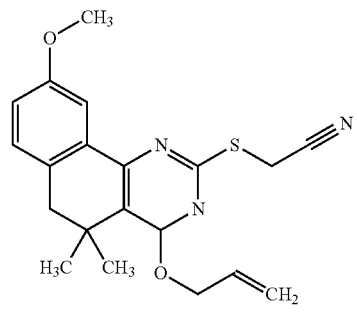
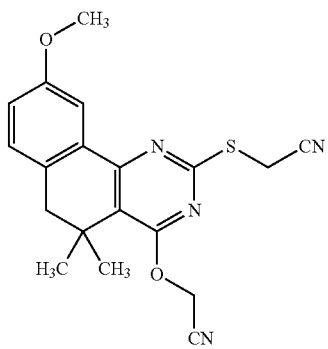

-continued

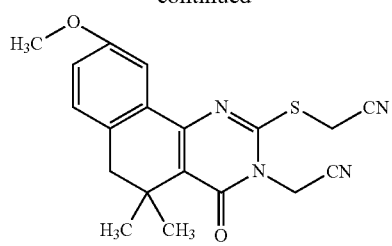

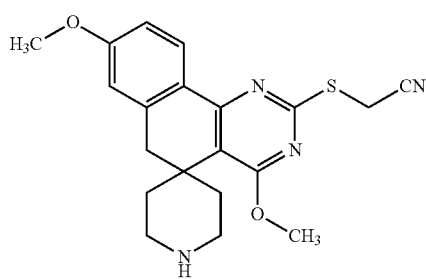

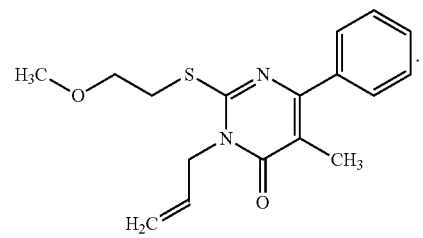

or

In another embodiment, the compound is, for example

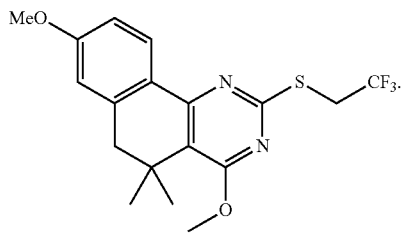 [SMILES: COc1ccc2c(c1)CC(C)(C)c1c(OC)nc(SCC(F)(F)F)nc1-2]

Another embodiment of the present disclosure provides a composition comprising: a compound having the structure of Formula V

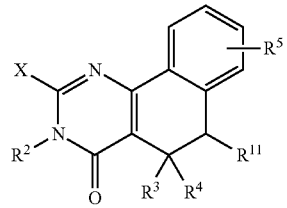

wherein X is $SR^1$, $NH_2$, $NHR^1$, $NR^1R$, OH, $OR^1$, or Cl; wherein R, $R^1$ and $R^2$ are, independently, H, a C1-C8 alkyl or alkenyl or cycloalkyl, optionally substituted with F, CN, $OR^6$, $NR^6_2$, $COR^6$, $CO_2R^6$, $CONHR^6$, aryl or heteroaryl, wherein one or more alkyl carbons may be replaced by O; $R^3$ and $R^4$ are, independently, a C1-C8 alkyl; $R^5$ is H, C1-C6 alkyl, CN, $OR^6$, $NR^6_2$, $COR^6$, $CO_2R^6$, $CONHR^6$, aryl, heteroaryl, $SO_2R^6$, $NHCOR^6$, $SO_2NHR^6$, or $OCOR^6$; $R^6$ is H, C1-C6 alkyl, C0-C3 alkyl-aryl, or C0-C3 alkyl-heteroaryl, all optionally substituted; and $R^{11}$ is H or a C1 alkyl. Exemplary compounds are shown below:

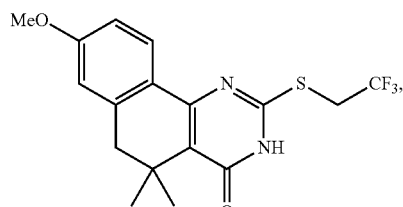

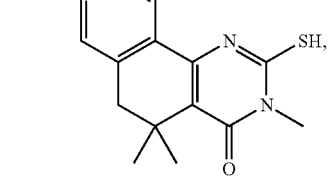

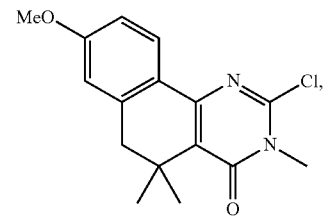

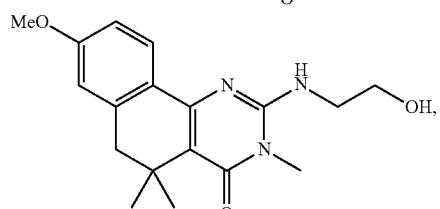

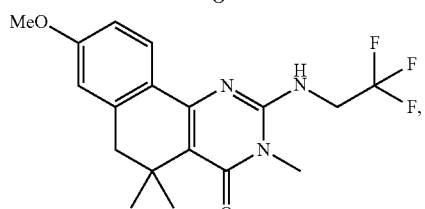

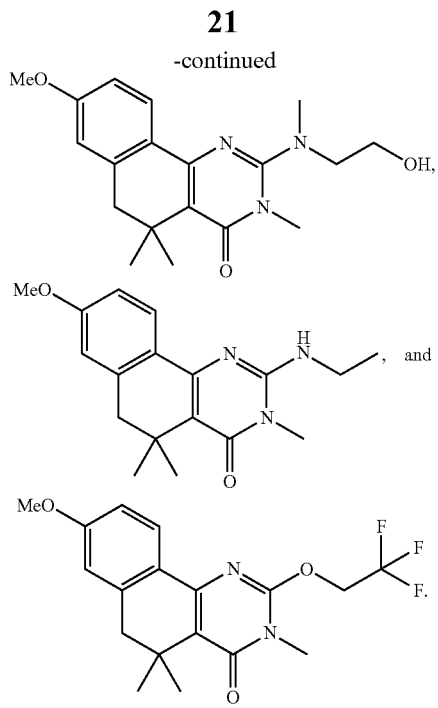

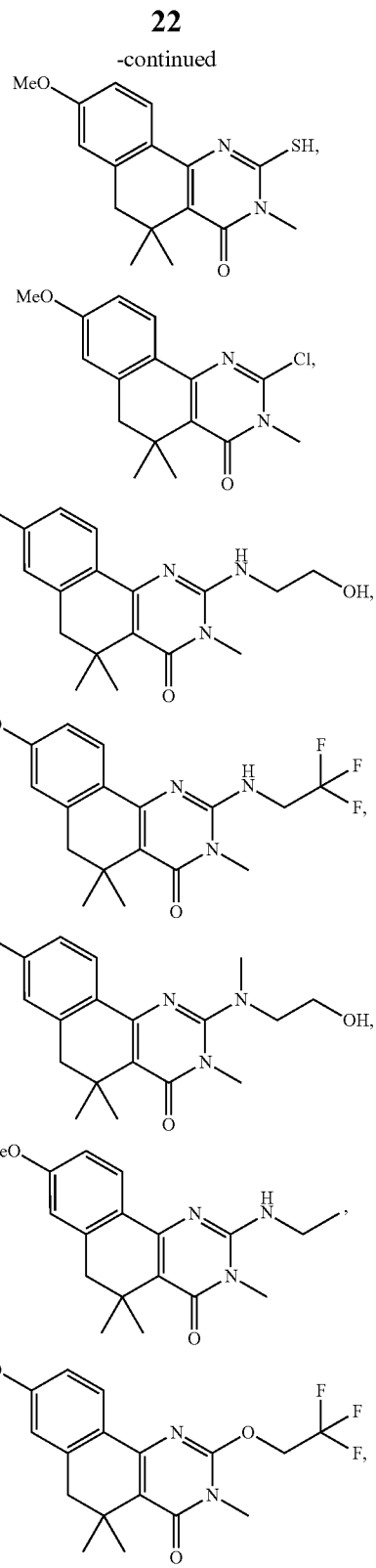

In some embodiments, the composition further comprises a pharmaceutically acceptable carrier.

The present disclosure is further directed to topical formulations comprising: a compound having the structure of Formula V (V)

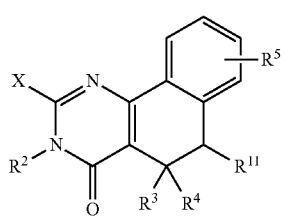

wherein X is $SR^1$, $NH_2$, $NHR^1$, $NR^1R$, OH, $OR^1$, or Cl; wherein R, $R^1$ and $R^2$ are, independently, H, a C1-C8 alkyl or alkenyl or cycloalkyl, optionally substituted with F, CN, $OR^6$, $NR^6_2$, $COR^6$, $CO_2R^6$, $CONHR^6$, aryl or heteroaryl, wherein one or more alkyl carbons may be replaced by O; $R^3$ and $R^4$ are, independently, a C1-C8 alkyl; $R^5$ is H, C1-C6 alkyl, CN, $OR^6$, $NR^6_2$, $COR^6$, $CO_2R^6$, $CONHR^6$, aryl, heteroaryl, $SO_2R^6$, $NHCOR^6$, $SO_2NHR^6$, or $OCOR^6$; $R^6$ is H, C1-C6 alkyl, C0-C3 alkyl-aryl, or C0-C3 alkyl-heteroaryl, all optionally substituted; and $R^{11}$ is H or a C1 alkyl; and a base.

In some embodiments, the compound is selected from the group consisting of:

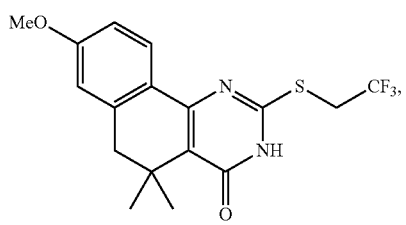

and combinations thereof.

The present disclosure is further directed to methods of treating a bacterial infection in a subject in need thereof, the method comprising applying to the subject in need thereof a topical formulation comprising a compound having the structure of Formula V

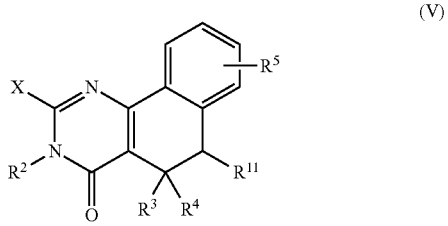

(V)

wherein X is $SR^1$, $NH_2$, $NHR^1$, $NR^1R$, OH, $OR^1$, or Cl; wherein R, $R^1$ and $R^2$ are, independently, H, a C1-C8 alkyl or alkenyl or cycloalkyl, optionally substituted with F, CN, $OR^6$, $NR^6{}_2$, $COR^6$, $CO_2R^6$, $CONHR^6$, aryl or heteroaryl, wherein one or more alkyl carbons may be replaced by O; $R^3$ and $R^4$ are, independently, a C1-C8 alkyl; $R^5$ is H, C1-C6 alkyl, CN, $OR^6$, $NR^6{}_2$, $COR^6$, $CO_2R^6$, $CONHR^6$, aryl, heteroaryl, $SO_2R^6$, $NHCOR^6$, $SO_2NHR^6$, or $OCOR^6$; $R^6$ is H, C1-C6 alkyl, C0-C3 alkyl-aryl, or C0-C3 alkyl-heteroaryl, all optionally substituted; and $R^{11}$ is H or a C1 alkyl; and a base.

The method can further include combination with conventional antibiotics and other antibacterial therapies.

Another embodiment provides a method treatment for humans and animals (companion and agriculture) are potential applications. The inventive compounds may also be used in agricultural animals to control infections and reduce the use of classical antibiotics that leads to resistant bacteria and the diminished efficacy for humans.

Additional embodiments are described herein.

BRIEF DESCRIPTION OF THE DRAWINGS

The patent or patent application file contains at least one drawing executed in color. Copies of this patent or patent application publication with color drawings will be provided by the Office upon request and payment of the necessary fee. The disclosure will be better understood, and features, aspects and advantages other than those set forth above will become apparent when consideration is given to the following detailed description thereof. Such detailed description makes reference to the following drawings, wherein:

FIG. 1A) Microarray analysis of gene expression changes in MGAS2221 treated with CCG-102487 compared to DMSO. FIG. 1B) Effect of CCG-2979 on mice survival after infection with GAS (105-6 CFU per mouse).

FIG. 2A) CCG-203592 and FIG. 2B) CCG-205363 inhibited *S. aureus* RN6390 strain biofilm formation different concentrations. FIG. 2C) effect of 203592 on *S. aureus* RN6390 strain gene expression at 50 μM. Real time RT-PCRs were performed at mid-logarithmic growth phase (ML), late logarithmic growth phase (LL) and stationary (S) phase. FIG. 2D) CCG-203592 protected BALB/cJ mice against intranasal *S. aureus* Newman strain infection (3-4× 10⁸ CFU per mouse). FIG. 2E) CCG-203043 inhibited *S. epidermidis* RP62A strain biofilm formation in microtiter plate without inhibiting bacterial growth.

FIG. 6 shows synthesis of exemplary biofilm inhibitors.
FIG. 7 shows synthesis of exemplary biofilm inhibitors.

FIGS. 11A and 11B show anti-virulence of *S. aureus* virulence in vivo. FIG. 11A shows bacterial counts in lung tissues of mice intranasally infected with 10⁷ CFU bacteria and treated with 0.15 μmole CCG-211790 or DMSO. FIG. 11B shows bacterial counts in spleen tissues of mice intranasally infected with 10⁷ CFU bacteria and treated with 0.15 μmole CCG-211790 or DMSO.

FIG. 13A shows CCG-211790 mitigated wound infections by MRSA in diet induced obesity (DIO) mice. FIG. 13B shows CCG-211790 reduced cytotoxicity of MRSA on CCL-1 by the alpha-hemolysis virulence factor (red dye indicated apoptosis/dead cells). FIGS. 13C and 13D show CCG-211790 mitigated wound infections by *P. aeruginosa* in diet induced obesity (DIO) mice.

FIG. 15A is a western blot of fliC expression at different concentrations of CCG-211790 (NV001). FIG. 15B shows reduction in *E. coli* adhesion to Caco2 cells by CCG-211790 (NV001).

FIG. 16A shows CCG-211790 had little effect on MRSA growth. FIG. 16B shows a dose-response curve of MRSA response to amoxicillin and amoxicillin with 50 μM CCG-211790. FIG. 16C shows a dose-response curve of MRSA response to vancomycin and vancomycin with 50 μM CCG-211790. FIG. 16D shows a dose-response curve of MRSA response to clindamycin and clindamycin with 50 μM CCG-211790. FIG. 16E shows a dose-response curve of MRSA response to tetracycline and tetracycline with 50 μM CCG-211790. FIG. 16F shows a dose-response curve of MRSA response to erythromycin and erythromycin with 50 μM CCG-21790.

FIG. 17A shows enhancement of vancomycin potency by CCG-211790 against *Acinetobacter baumannii* (dotted line) as compared to vancomycin alone (solid line). FIG. 17B shows enhancement of ciprofloxacin potency by CCG-211790 against *P. aeruginosa* (dotted line) as compared to ciprofloxacin alone (solid line).

FIGS. 20A and 20B are graphs depicting reduced *P. aeruginosa* infected wound lesion size in wounds treated with topical cream formulation with different concentrations of NV001 for 3 days (FIG. 20A) and Day 8 (FIG. 20B).

FIGS. 21A and 21B are graphs depicting reduced MRSA infected wound lesion size in wounds treated with topical cream formulation with different concentrations of NV001 for 3 days (FIG. 21A) and Day 8 (FIG. 21B).

DETAILED DESCRIPTION

Figure 1A:
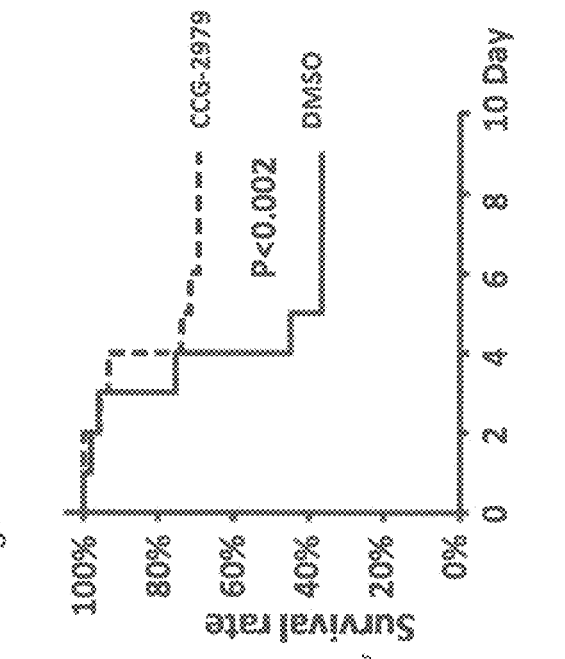
FIGS. 1A & 1B show the identification of a chemical series of compounds inhibiting group A *streptococcus* virulence.

To facilitate an understanding of the present disclosure, a number of terms and phrases are defined below.

As used herein, the term "aliphatic" represents the groups including, but not limited to, alkyl, alkenyl, alkynyl, alicyclic.

As used herein, the term "alkyl" refers to an unsaturated carbon chain substituent group. In general, alkyls have the general formula $C_nH_{2n+1}$. Exemplary alkyls include, but are not limited to, methyl ($CH_3$), ethyl ($C_2H_5$), propyl ($C_3H_7$), butyl ($C_4H_9$), pentyl ($C_5H_{11}$), etc.

As used herein, the term "aryl" represents a single aromatic ring such as a phenyl ring, or two or more aromatic rings (e.g., bisphenyl, naphthalene, anthracene), or an aromatic ring and one or more non-aromatic rings. The aryl group can be optionally substituted with a lower aliphatic group (e.g., alkyl, alkenyl, alkynyl, or alicyclic). Additionally, the aliphatic and aryl groups can be further substituted by one or more functional groups including, but not limited to, chemical moieties comprising N, S, O, —$NH_2$, —$NHCOCH_3$, —OH, lower alkoxy ($C_1$-$C_4$), and halo (—F, —Cl, —Br, or —I).

As used herein, the term "substituted aliphatic" refers to an alkane, alkene, alkyne, or alicyclic moiety where at least one of the aliphatic hydrogen atoms has been replaced by, for example, a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such include, but are not limited to, 1-chloroethyl and the like.

As used herein, the term "substituted aryl" refers to an aromatic ring or fused aromatic ring system consisting of at least one aromatic ring, and where at least one of the hydrogen atoms on a ring carbon has been replaced by, for example, a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl and the like.

As used herein, the term "cycloaliphatic" refers to an aliphatic structure containing a fused ring system. Examples of such include, but are not limited to, decalin and the like.

As used herein, the term "substituted cycloaliphatic" refers to a cycloaliphatic structure where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 1-chlorodecalyl, bicyclo-heptanes, octanes, and nonanes (e.g., nonrbornyl) and the like.

As used herein, the term "heterocyclic" represents, for example, an aromatic or nonaromatic ring containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted with one or more groups selected from aliphatic, nitro, acetyl (i.e., —C(=O)—$CH_3$), or aryl groups.

As used herein, the term "substituted heterocyclic" refers to a heterocylic structure where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to 2-chloropyranyl.

As used herein, the term "electron-rich heterocycle," means cyclic compounds in which one or more ring atoms is a heteroatom (e.g., oxygen, nitrogen or sulfur), and the heteroatom has unpaired electrons which contribute to a 6-π electronic system. Exemplary electron-rich heterocycles include, but are not limited to, pyrrole, indole, furan, benzofuran, thiophene, benzothiophene and other similar structures.

As used herein, the term "linker" refers to a chain containing up to and including eight contiguous atoms connecting two different structural moieties where such atoms are, for example, carbon, nitrogen, oxygen, or sulfur. Ethylene glycol is one non-limiting example.

As used herein, the term "lower-alkyl-substituted-amino" refers to any alkyl unit containing up to and including eight carbon atoms where one of the aliphatic hydrogen atoms is replaced by an amino group. Examples of such include, but are not limited to, ethylamino and the like.

As used herein, the term "lower-alkyl-substituted-halogen" refers to any alkyl chain containing up to and including eight carbon atoms where one of the aliphatic hydrogen atoms is replaced by a halogen. Examples of such include, but are not limited to, chlorethyl and the like.

As used herein, the term "acetylamino" shall mean any primary or secondary amino that is acetylated. Examples of such include, but are not limited to, acetamide and the like.

As used herein, the term "a moiety that participates in hydrogen bonding" as used herein represents a group that can accept or donate a proton to form a hydrogen bond thereby. Some specific non-limiting examples of moieties that participate in hydrogen bonding include a fluoro, oxygen-containing and nitrogen-containing groups that are well-known in the art. Some examples of oxygen-containing groups that participate in hydrogen bonding include: hydroxy, lower alkoxy, lower carbonyl, lower carboxyl, lower ethers and phenolic groups. The qualifier "lower" as used herein refers to lower aliphatic groups ($C_1$-$C_4$) to which the respective oxygen-containing functional group is attached. Thus, for example, the term "lower carbonyl" refers to inter alia, formaldehyde, acetaldehyde. Some non-limiting examples of nitrogen-containing groups that participate in hydrogen bond formation include amino and amido groups. Additionally, groups containing both an oxygen and a nitrogen atom can also participate in hydrogen bond formation. Examples of such groups include nitro, N-hydroxy and nitrous groups. It is also possible that the hydrogen-bond acceptor in the present disclosure can be the π electrons of an aromatic ring.

The term "derivative" of a compound, as used herein, refers to a chemically modified compound wherein the chemical modification takes place either at a functional group of the compound or backbone.

As used herein, the term "subject" refers to organisms to be treated by the methods of the present disclosure. Such organisms preferably include, but are not limited to, mammals (e.g., murines, simians, equines, bovines, porcines, canines, felines, and the like), and most preferably includes humans. As used herein, the term "subject" generally refers to an individual who will receive or who has received treatment (e.g., administration of a compound of the present disclosure and optionally one or more other agents) for a condition characterized by bacterial infection.

The term "diagnosed," as used herein, refers to the recognition of a disease by its signs and symptoms (e.g., resistance to conventional therapies), or genetic analysis, pathological analysis, histological analysis, and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "effective amount" refers to the amount of a compound (e.g., a compound of the present disclosure) sufficient to effect beneficial or desired results. An effective amount can be administered in one or more administrations, applications or dosages and is not intended to be limited to a particular formulation or administration route.

As used herein, the term "co-administration" refers to the administration of at least two agent(s) (e.g., a compound of the present disclosure) or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present disclosure which, upon administration to a subject, is capable of providing a compound of this disclosure or an active metabolite or residue thereof. As is known to those of skill in the art, "salts" of the compounds of the present disclosure may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds disclosed herein and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present disclosure compounded with a suitable cation such as $Na^+$, $NH_4^+$, and $NW_4^+$ (wherein W is a $C_{1-4}$ alkyl group), and the like.

For therapeutic use, salts of the compounds of the present disclosure are contemplated as being pharmaceutically acceptable. However, salts of acids and bases that are non-pharmaceutically acceptable may also find use, for example, in the preparation or purification of a pharmaceutically acceptable compound.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present disclosure.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

As used herein, the term "modulate" refers to the activity of a compound (e.g., a compound of the present disclosure) to affect (e.g., to promote or retard) an aspect of cellular function, including, but not limited to, bacterial growth and the like.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., bacterial infection). Test compounds comprise both known and potential therapeutic compounds. A test compound can be determined to be therapeutic by using the screening methods of the present disclosure. A "known therapeutic compound" refers to a therapeutic compound that has been shown (e.g., through animal trials or prior experience with administration to humans) to be effective in such treatment or prevention.

As used herein, the term "biofilm" refers to an aggregate of microorganisms (e.g., bacteria) in which cells adhere to each other on a surface. These adherent cells are frequently embedded within a self-produced matrix of extracellular polymeric substance. Biofilms are formed in a variety of infections of the human body and on medical devices. Examples include, but are not limited to, urinary tract infections, catheter infections, middle-ear infections, formation of dental plaque, gingivitis, coating contact lenses, endocarditis, infections in cystic fibrosis, and infections of permanent indwelling devices such as joint prostheses and heart valves. A variety of bacteria form biofilms. Examples include but are not limited to, Pseudomonas aeruginosa, Staphylococcus aureus, Staphylococcus epidermidis, dental plaque (e.g., Streptococcus mutans and Streptococcus sanguinis), Legionella, and Neisseria gonorrhoeae.

The present disclosure relates to chemical compounds, methods for their discovery, and their therapeutic and research use. In particular, the present disclosure provides compounds as therapeutic agents against bacterial infections.

The emergence of antibiotic resistance is an urgent medical problem worldwide. Many of the current antibiotics are derivatives of parental compounds that were developed more than forty years ago and target a small set of proteins essential for bacterial survival, such as cell wall formation, and synthesis of bacterial DNA, RNA, lipid and protein. As a result, antibiotic resistant strains have been favored by selective pressure (Martinez et al., Clin. Microbiol. Rev. 2002; 15:647-679). A number of other factors, including inappropriate and excessive use of antibiotics, have contributed to the emergence of pathogens that are highly resistant to most currently available antibiotics (Alanis, Arch. Med. Res. 2005; 36:697-705; Bax et al., Int. J. Antimicrob. Agents 2000; 16:51-59; Norrby et al., Lancet Infect. Dis. 2005; 5:115-119; Silver, Nat. Rev. Drug Discov. 2007; 6:41-55). Current antimicrobial development is largely limited to improving the efficacy of existing antibiotics.

There is thus a great need for the development of novel strategies to combat infectious diseases. The inhibition of pathogen virulence without introducing selection for antibiotic resistance holds tremendous promise as an alternative to traditional antibiotic strategies.

Accordingly, in some embodiments, the present disclosure provides compositions and methods active against bacterial infections (e.g., group A streptococcus and biofilms caused by a variety of bacteria). In experiments conducted during the course of development of embodiments of the present disclosure, a chemical series of compounds capable of inhibiting biofilm formation on a number of biomaterial surfaces by Staphylococcus aureus and Staphylococcus epidermidis without inhibiting bacterial growth significantly was identified. It was also demonstrated that these compounds are able to inhibit expression of a number of virulence factors including genes involved in biofilm formation. The chemical series of compounds are further capable of inhibiting virulence other bacteria including both gram-positive and gram-negative bacteria. The chemical series of compounds are useful in methods for treating pneumonia in a subject in need thereof, methods for reducing bacterial virulence, methods for treating a bacterial wound infection in a subject in need thereof, methods for treating a urinary tract infection in a subject in need thereof, and methods for treating a bacterial infection, wherein the bacterial infection has or is suspected of having an antibiotic-resistant bacteria.

The present disclosure is not limited to a particular mechanism. Indeed, an understanding of the mechanism is not necessary to practice the present disclosure. Nonetheless, it is contemplated that the compositions and methods described herein, that inhibit biofilm formation without inhibiting bacterial growth, do not induce rapid resistance of bacteria to antibiotics (e.g., the compounds described herein and conventional antibiotics).

In some embodiments, the present disclosure provides a local drug delivery method that combine the compounds described herein and a coating (e.g., plasma coating) as a drug release control barrier (M Chen, et al., Journal of Biomaterials Science 23: 483-496, 2012). In some embodiments, compounds are covalently bound onto the surface of the biomaterials (V. Antoci, et al., Biomaterials 29:4684-4690, 2008; Hume EBS, Biomaterials 25: 5023-5030, 2004).

I. Inhibitors

As described in more detail below, embodiments of the present disclosure provide compounds that specifically inhibit bacterial virulence or growth, for example, in biofilms (e.g., biofilms on biological or medical surfaces).

In some embodiments, inhibitors have the structure compound having the structure of Formula I, II, III or IV

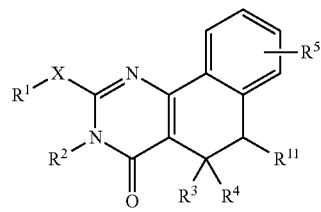

I

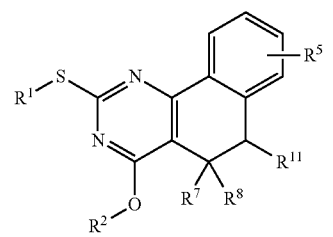

II

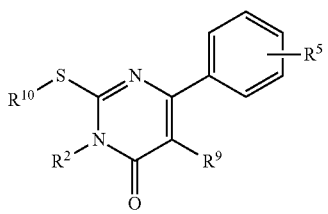

III

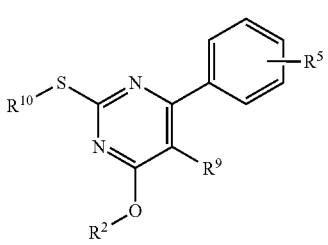

IV wherein X is S, SH, N, NH, OH, or $OR^1$; wherein $R^1$ and $R^2$ are, independently, a C1-C8 alkyl or alkenyl or cycloalkyl, optionally substituted with F, CN, $OR^6$, $NR^6_2$, $COR^6$, $CO_2R^6$, $CONHR^6$, aryl or heteroaryl, wherein one or more alkyl carbons may be replaced by O; $R^3$ and $R^4$ are joined in a cycloalkyl ring of 3-7 carbons wherein at least one ring $CH_2$ is replaced by O or N-G; G is H, C(=O)$R^6$, $SO_2R^6$ or C(=O)$OR^6$; $R^5$ is H, C1-C6 alkyl, CN, $OR^6$, $NR^6_2$, $COR^6$, $CO_2R^6$, $CONHR^6$, aryl, heteroaryl, $SO_2R^6$, $NHCOR^6$, $SO_2NHR^6$, or $OCOR^6$; $R^6$ is H, C1-C6 alkyl, C0-C3 alkyl-aryl, or C0-C3 alkyl-heteroaryl, all optionally substituted; $R^7$ and $R^8$ are independently H, C1-C6 alkyl, or joined in a cycloalkyl ring of 3-7 carbons, wherein one of the ring $CH_2$ groups may be replaced by O or N-G; $R^9$ is C1-C5 alkyl; and $R^{10}$ is a C2-C8 alkyl or alkenyl or cycloalkyl, optionally substituted with F, CN, $OR^6$, $NR^6_2$, $CO_2R^6$, $CONHR^6$, aryl or heteroaryl, wherein one or more alkyl carbons may be replaced by O. Exemplary compounds are shown below:

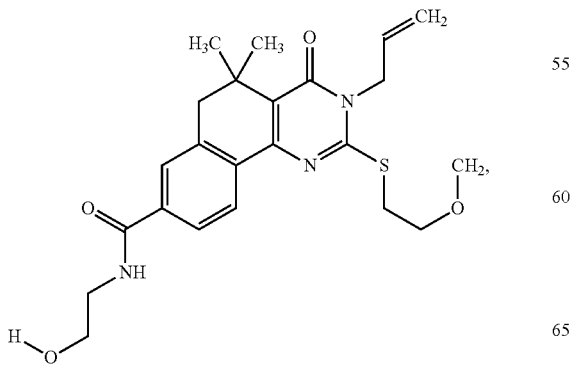

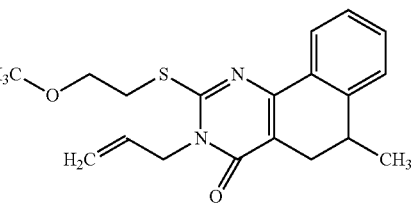

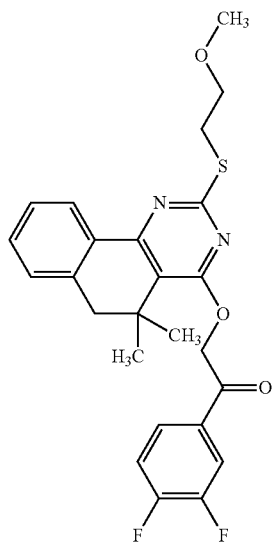

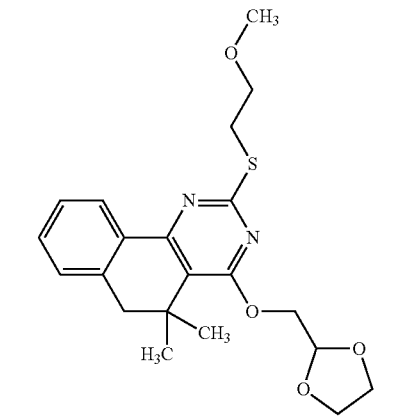

-continued
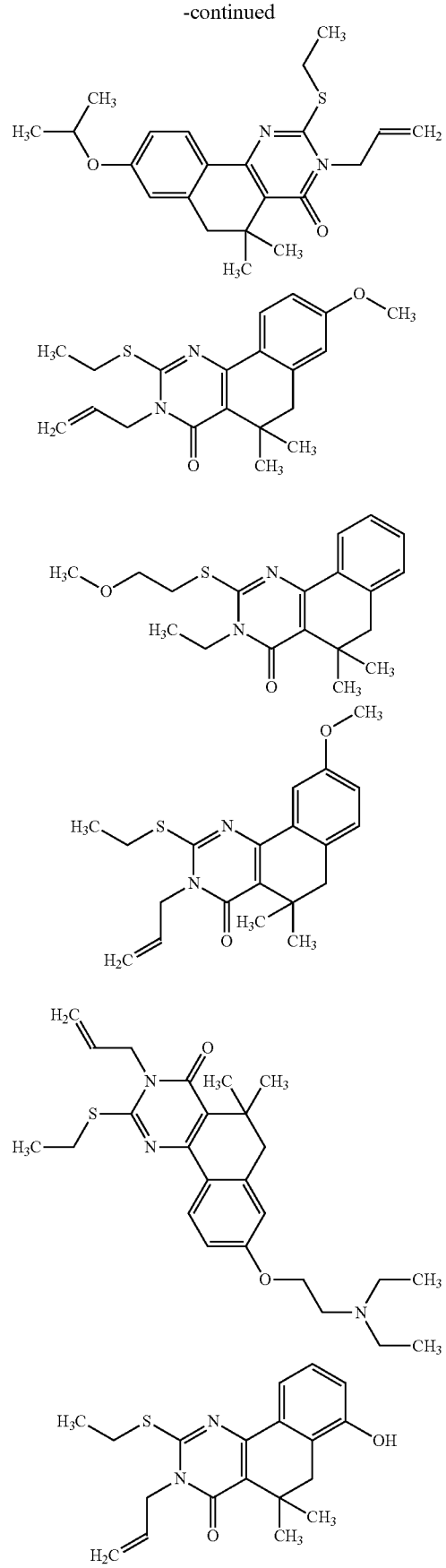
-continued
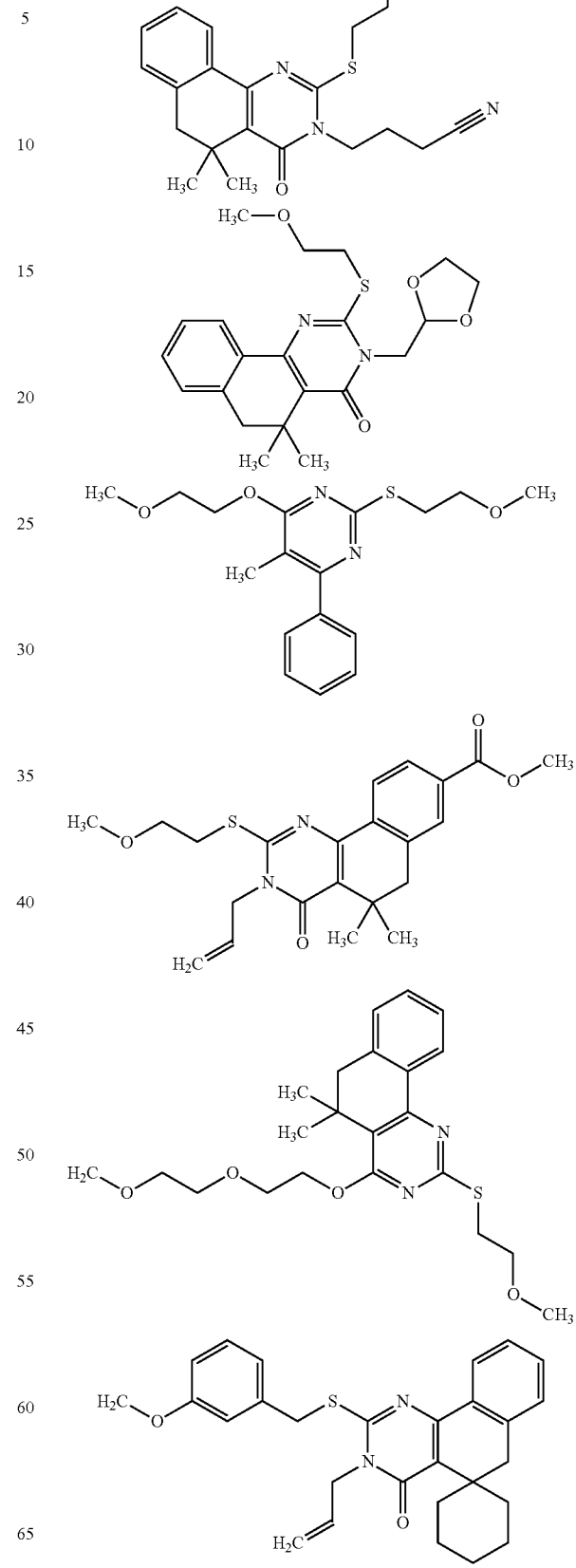

35
-continued
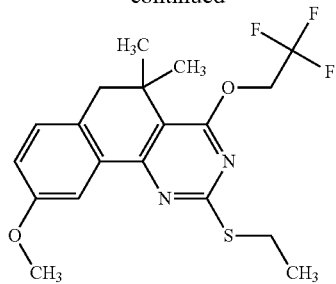
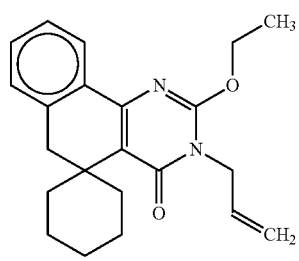
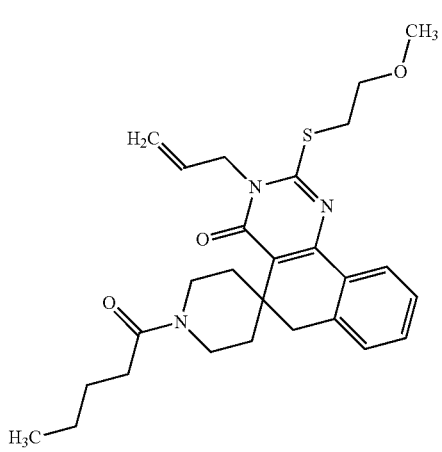
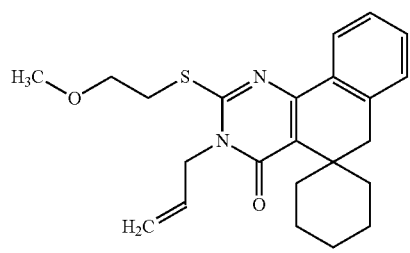
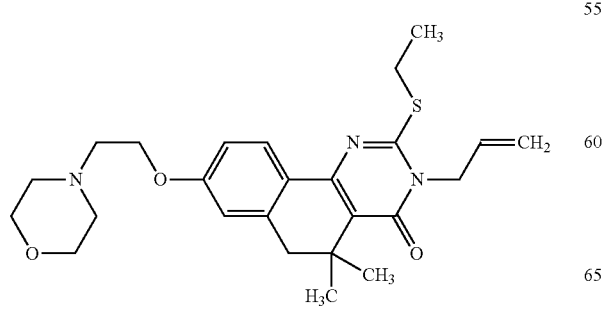
36
-continued
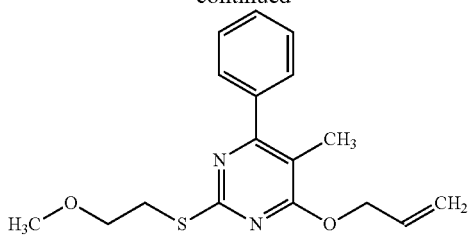
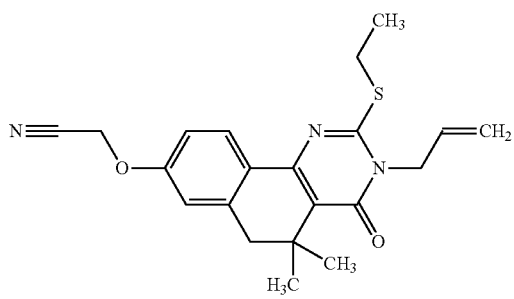
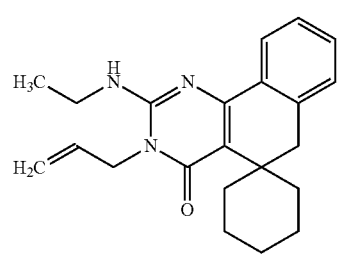
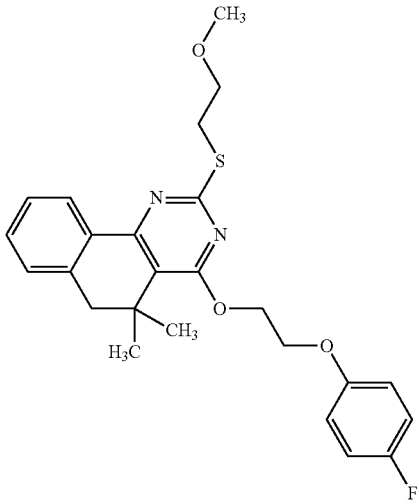
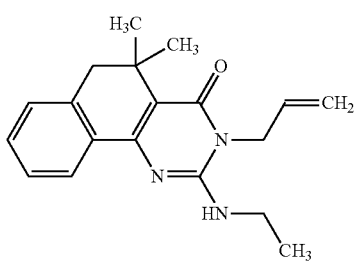

-continued
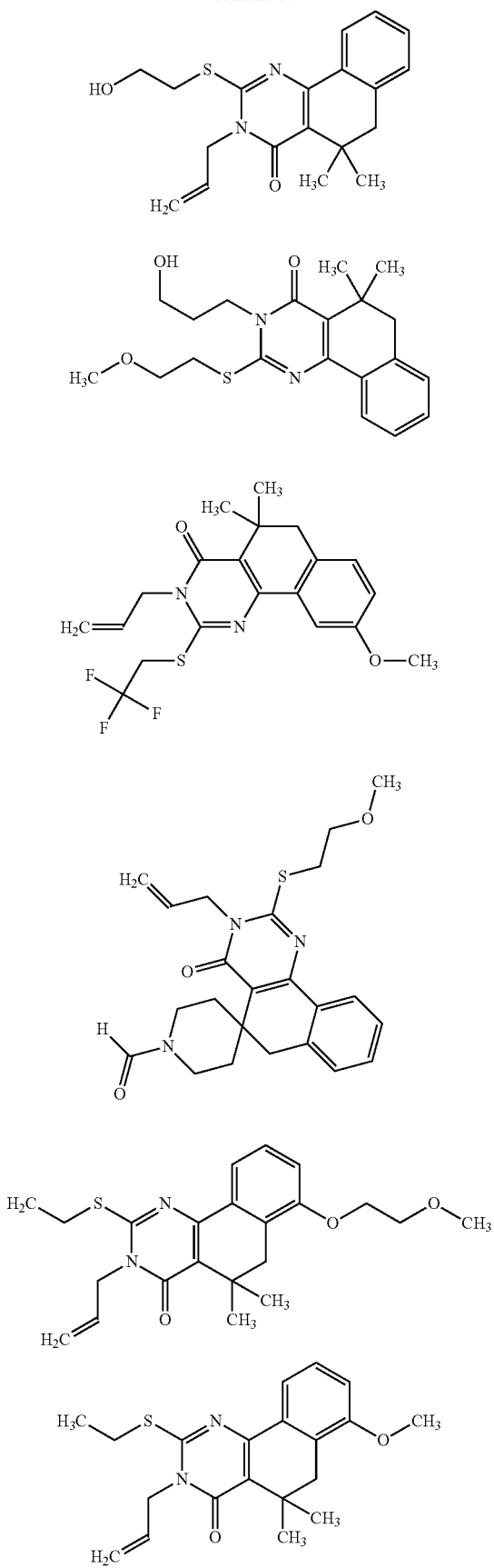
-continued
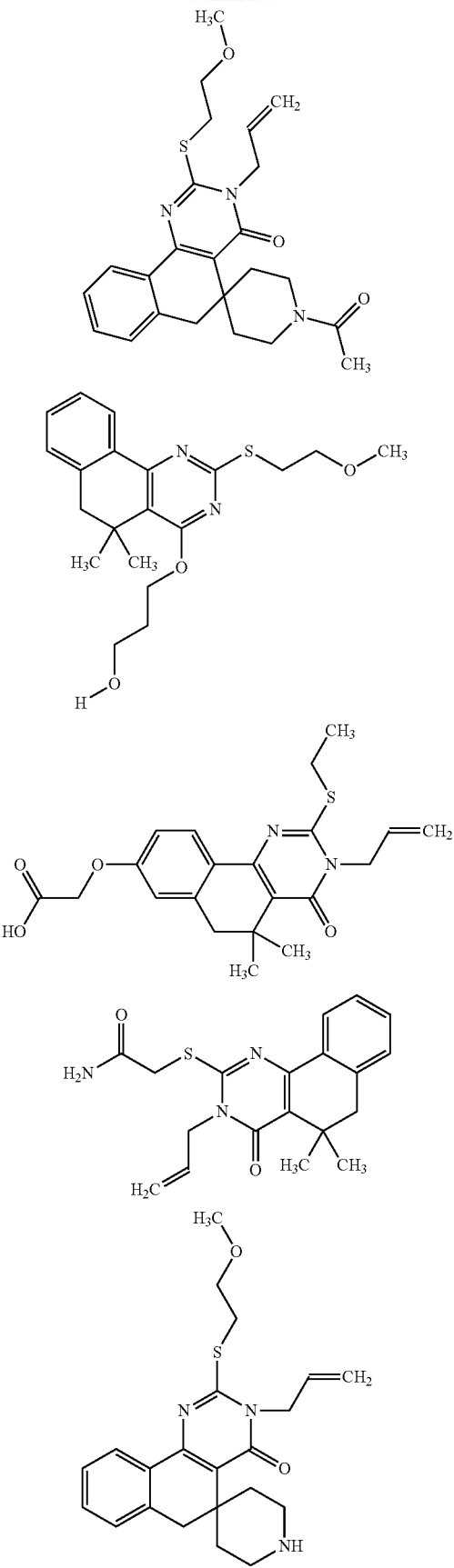

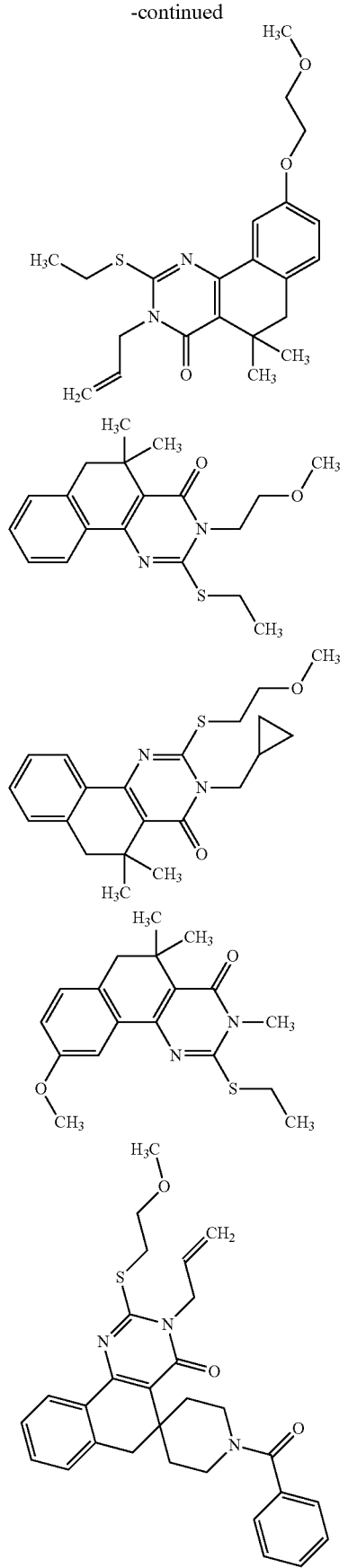
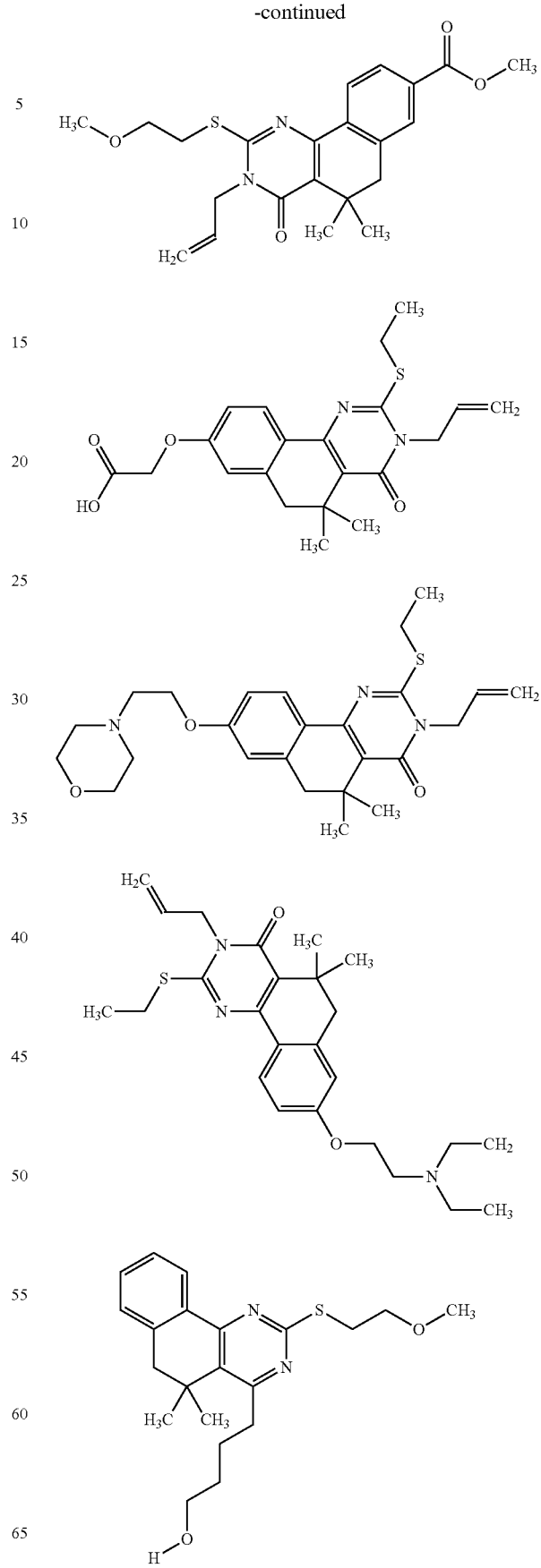

-continued
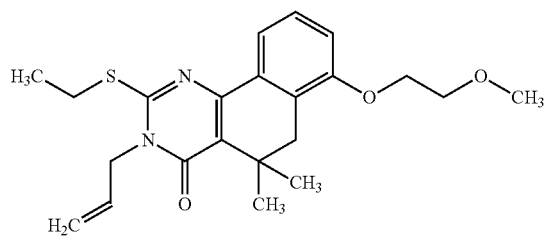
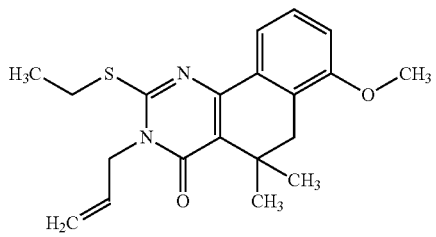
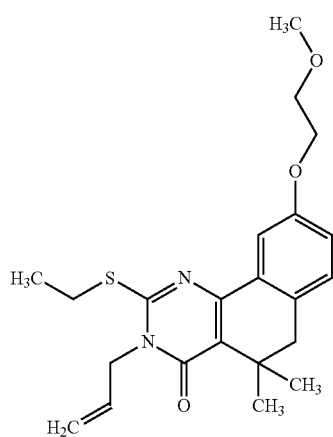
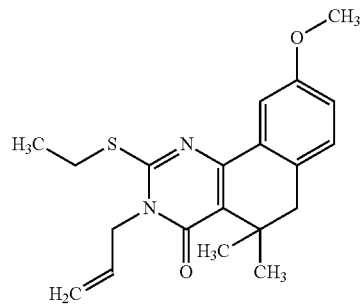
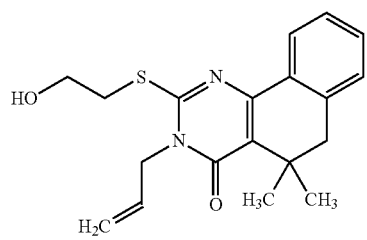
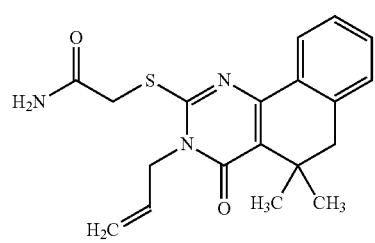
-continued
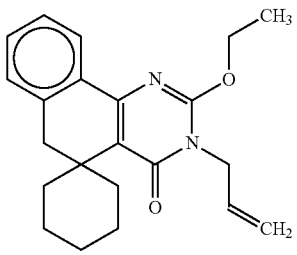
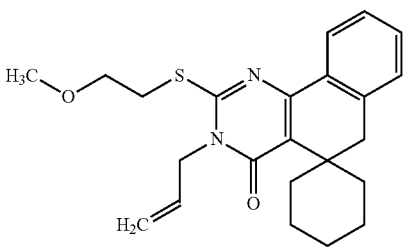
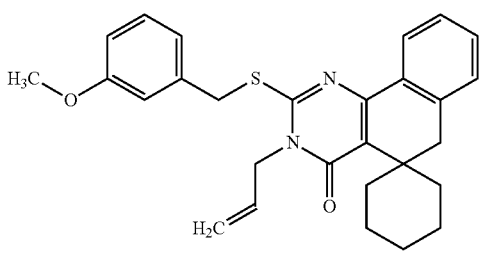
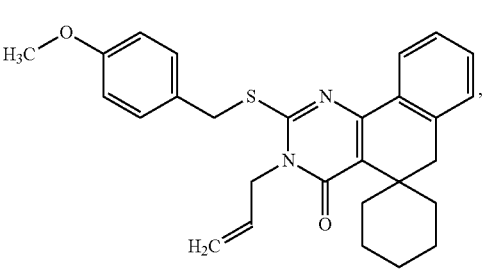
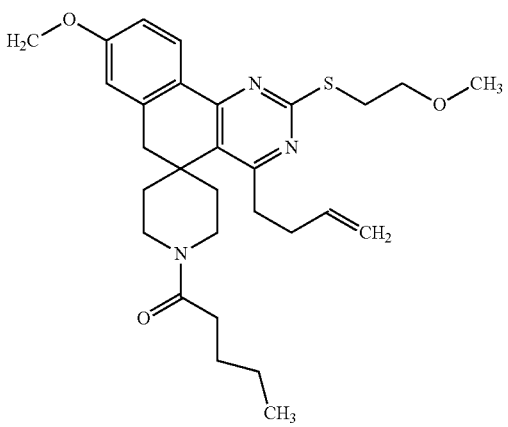

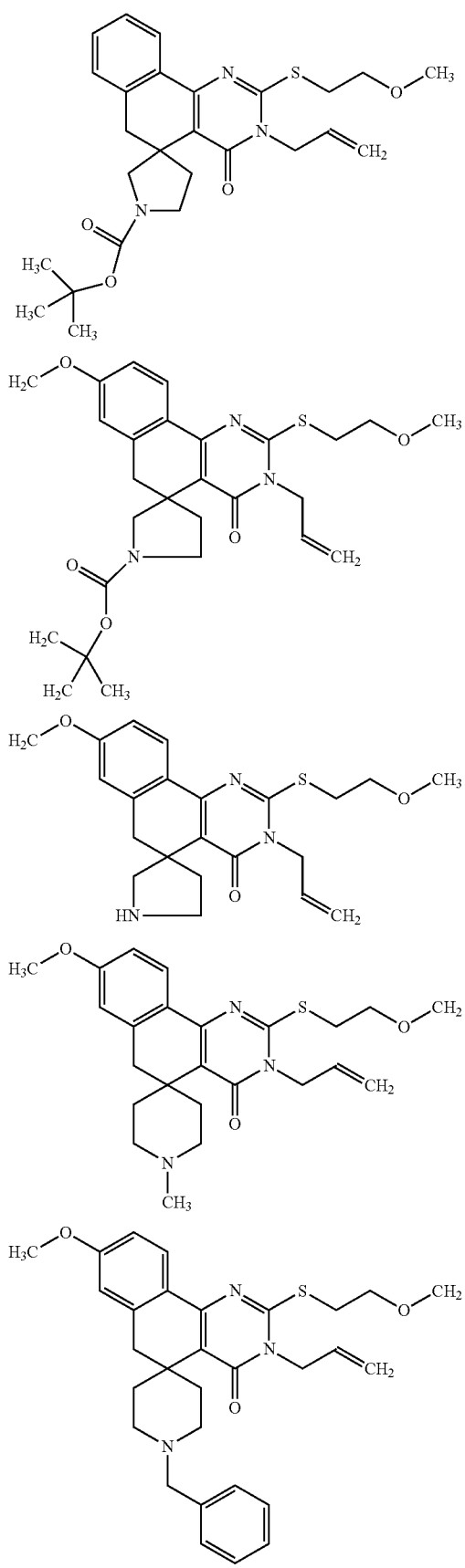
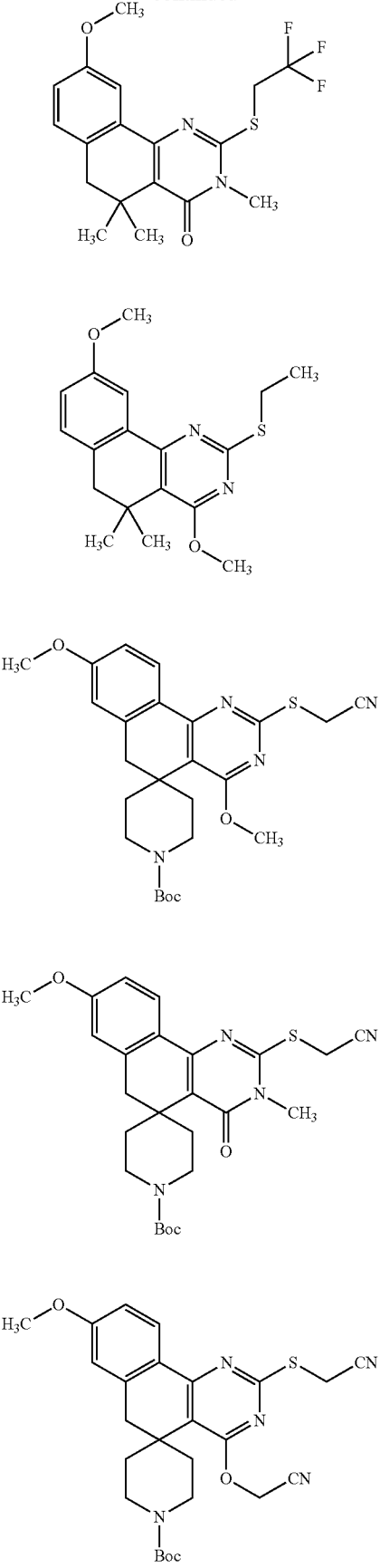

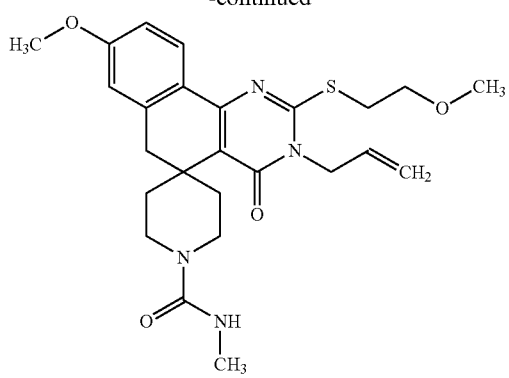
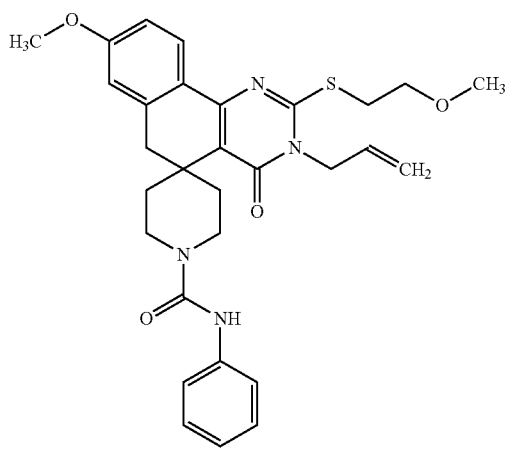
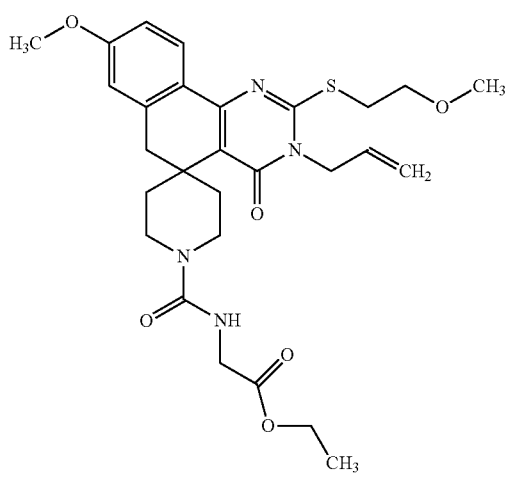
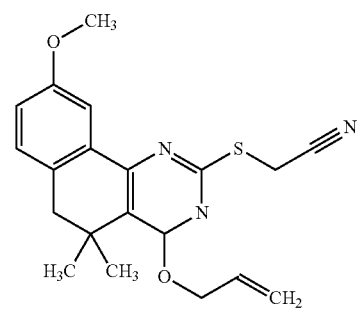
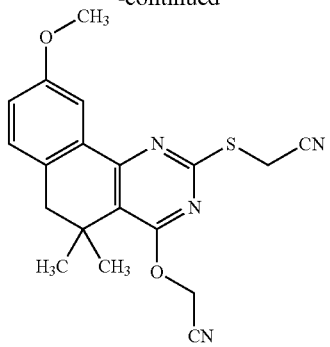
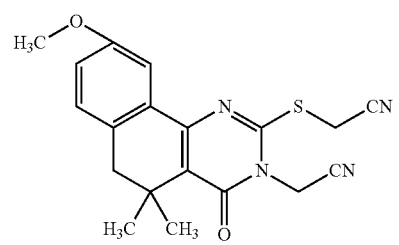
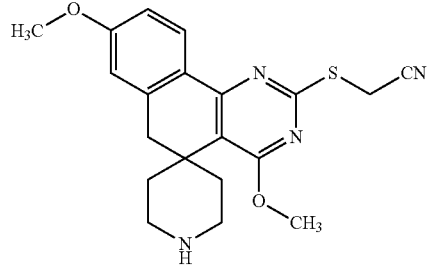
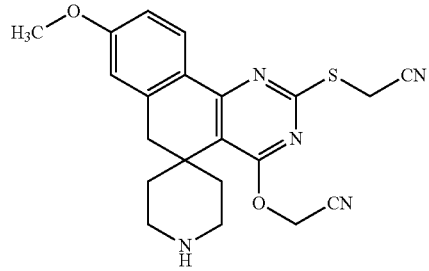
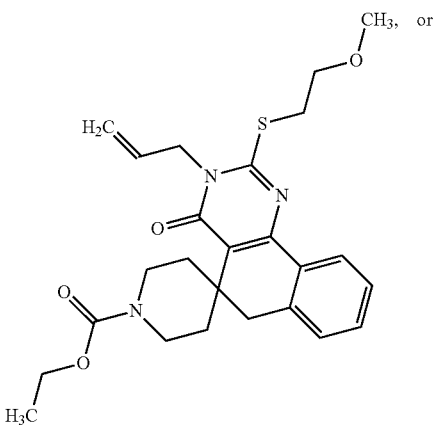

-continued

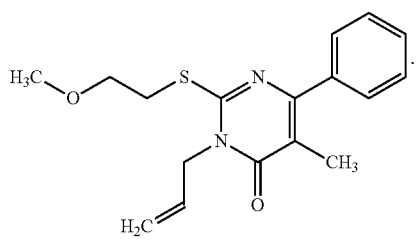

Another exemplary compound is

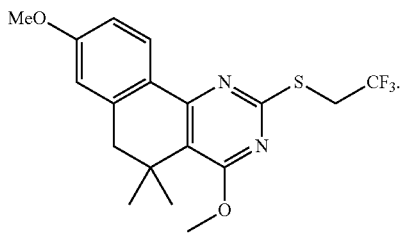 [SMILES: COc1ccc2c(c1)CC(C)(C)c1c(OC)nc(SCC(F)(F)F)nc1-2]

In another embodiment, compounds have the structure of Formula V

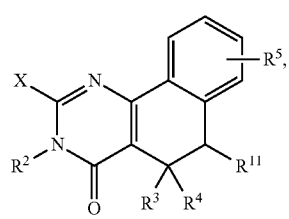

wherein X is $SR^1$, $NH_2$, $NHR^1$, $NR^1R$, OH, $OR^1$, or Cl; wherein R, $R^1$ and $R^2$ are, independently, H, a C1-C8 alkyl or alkenyl or cycloalkyl, optionally substituted with F, CN, $OR^6$, $NR^6{}_2$, $COR^6$, $CO_2R^6$, $CONHR^6$, aryl or heteroaryl, wherein one or more alkyl carbons may be replaced by O; $R^3$ and $R^4$ are, independently, a C1-C8 alkyl; $R^5$ is H, C1-C6 alkyl, CN, $OR^6$, $NR^6{}_2$, $COR^6$, $CO_2R^6$, $CONHR^6$, aryl, heteroaryl, $SO_2R^6$, $NHCOR^6$, $SO_2NHR^6$, or $OCOR^6$; $R^6$ is H, C1-C6 alkyl, C0-C3 alkyl-aryl, or C0-C3 alkyl-heteroaryl, all optionally substituted; and $R^{11}$ is H or a C1 alkyl. Exemplary compounds are shown below:

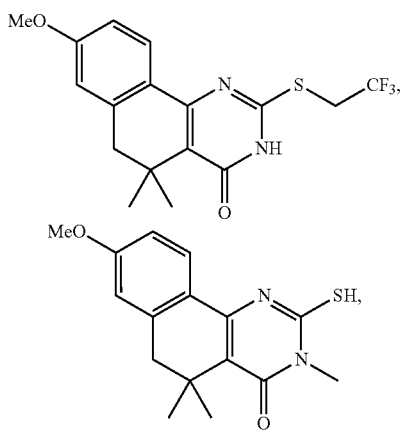

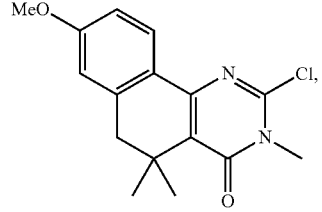

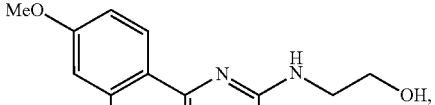

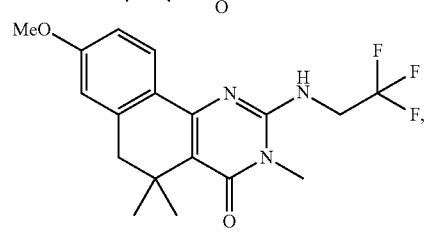

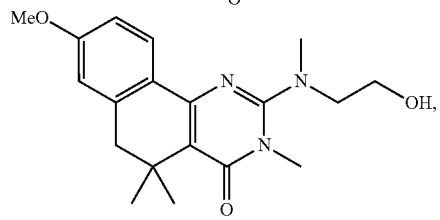

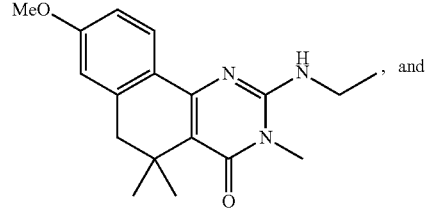

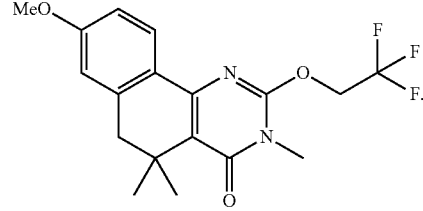 [SMILES: COc1ccc2c(c1)CC(C)(C)c1c-2nc(OCC(F)(F)F)n(C)c1=O]

II. Pharmaceutical Compositions, Formulations, and Exemplary Administration Routes and Dosing Considerations Exemplary embodiments of various contemplated medicaments and pharmaceutical compositions are provided below.

A. Preparing Medicaments

The compounds of the present disclosure are useful in the preparation of medicaments to treat bacterial infections. The compounds of the present disclosure are further useful in the preparation of medicaments for other treatment methods. The methods and techniques for preparing medicaments of a compound are well-known in the art. Exemplary pharmaceutical formulations and routes of delivery are described below.

One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present disclosure, the compositions are administered alone, while in some other embodiments, the compositions are preferably present in a pharmaceutical formulation comprising at least one active ingredient/agent, as described herein, together with a solid support or alternatively, together with one or more pharmaceutically acceptable carriers and optionally other therapeutic agents. Each carrier should be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In some embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration are optionally formulated as ointments, creams, suspensions, lotions, powders, solutions, pastes, gels, sprays, foams, aerosols or oils. In alternatively embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions are constituted from known ingredients in a known manner. This phase typically comprises a lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. It some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgent and emulsion stabilizers suitable for use include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations can include other agents conventional in the art having regard to the type of formulation in question, for example, those suitable for oral administration may include such further agents as sweeteners, thickeners and flavoring agents. It also is intended that the agents, compositions and methods be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

In some embodiments, compounds are coated on medical devices (e.g., including but not limited to, pacemakers, indwelling catheters, implants, joint replacements, bone repair devices and the like).

C. Exemplary Administration Routes and Dosing Considerations

Various delivery systems are known and can be used to administer a therapeutic agent such as, for example, encapsulation in liposomes, microparticles, microcapsules, nanoparticles, receptor-mediated endocytosis, and the like. Methods of delivery include, but are not limited to, intra-arterial, intra-muscular, intravenous, intranasal, and oral routes. In specific embodiments, it may be desirable to administer the pharmaceutical compositions locally to the area in need of treatment; this may be achieved by, for example, and not by way of limitation, local infusion during surgery, injection, or by means of a catheter.

The compounds disclosed herein as effective for their intended purpose can be administered to subjects or individuals susceptible to or at risk of developing bacterial infections, bacterial biofilm infection and conditions correlated with these infections. When the compound is administered to a subject such as a mouse, a rat or a human patient, the compound can be added to a pharmaceutically acceptable carrier and systemically or topically administered to the subject. To determine patients that can be beneficially treated, a tissue sample is removed from the patient and the cells are assayed for sensitivity to the compound.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the compounds are readily determined by those of skill in the art. Suitably, the compounds are administered at about 0.01 mg/kg to about 200 mg/kg, more preferably at about 0.1 mg/kg to about 100 mg/kg, even more preferably at about 0.5 mg/kg to about 50 mg/kg. Topical applications can administered at about 0.03% to about 3%. Dosage formulations can be administered in a single dose and in multiple doses. Dosage formulations can be administered in a single dose and in multiple doses on a single day and in a single dose and in multiple doses over multiple days. When the compounds described herein are co-administered with another agent (e.g., as sensitizing agents for antibiotics), the effective amount may be less than when the compound and/or agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to a compound, the pharmaceutical compositions can also contain other pharmaceutically active compounds or a plurality of compounds.

More particularly, a compound also referred to herein as the active ingredient, can be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the compound should be administered to achieve peak concentrations of the active compound at sites of disease. This may be achieved, for example, by the intravenous injection of the compound, optionally in saline, or orally administered, for example, as a tablet, capsule or syrup containing the active ingredient.

Desirable blood levels of the compound may be maintained by a continuous infusion to provide a therapeutic amount of the active ingredient within disease tissue. The use of operative combinations is contemplated to provide therapeutic combinations requiring a lower total dosage of each component than may be required when each individual therapeutic compound or drug is used alone, thereby reducing adverse effects.

D. Exemplary Co-Administration Routes and Dosing Considerations

The present disclosure also includes methods involving co-administration of the compounds described herein with one or more additional active agents. Indeed, it is a further aspect of this disclosure to provide methods for enhancing prior art therapies and/or pharmaceutical compositions by co-administering a compound of this disclosure. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or other treatments may each be administered using different modes or different formulations.

The agent or agents to be co-administered depends on the type of condition being treated. For example, when the condition being treated is bacterial infection, the additional agent can be a known antibiotic. The additional agents to be co-administered, such as antibacterial, immunosuppressant, immunostimulant, anti-inflammatory, and can be any of the well-known agents in the art, including, but not limited to, those that are currently in clinical use.

E. Biofilm Targeting Formulations

In some embodiments, formulations (e.g., pharmaceutical compositions) are formulated to treat biofilms of bacteria. Example formulations are described below.

Figure 10:
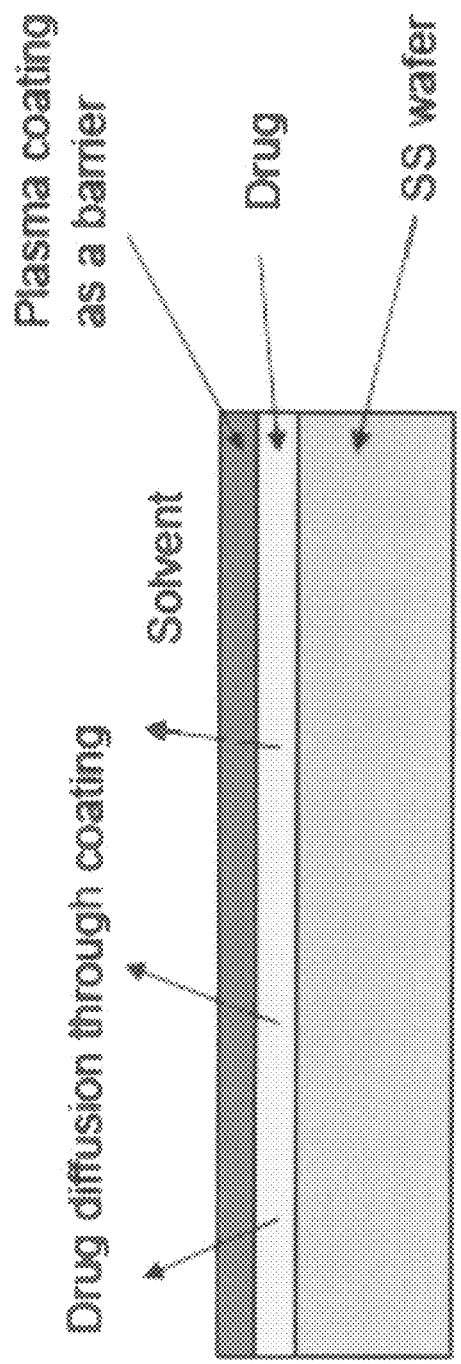
FIG. 10 shows Plasma coating on dip-coated stainless steel (SS) wafer.

The low temperature plasma coating technology offers a simple and cost-effective approach to control drug release as compared to the multi-step processes currently employed by many researchers or in commercial products, which frequently involve complex procedures. In some embodiments, plasma coating is tailored by optimizing the relevant coating process parameters, such as, for example, deposition time, plasma power, mass flow rate of monomer and working pressure inside the plasma reactor, to achieve a desired drug release rate for different drugs in clinical applications. Combining biofilm inhibitors with plasma coating increases the chance of obtaining broad spectrum anti-biofilm activity. FIG. 10 schematically illustrates drug diffusion through plasma coating on stainless steel as an example. The plasma generated coating on top of the drug (biofilm inhibitors) functions as permeation barrier between the drug molecules and the solvent. In some embodiments, plasma polymer coatings are optimized to generate an appropriate cross-linked structure and coating thickness, thus permitting diffusion of solvent and water molecules through the coating barrier with eventual dissolution of the drug molecules at desirable release rates.

In some embodiments, covalent attachment of the biofilm inhibitor to the surface of biomaterials is utilized, for example, to inhibit biofilm formation on implantable cardiovascular devices.

III. Drug Screens

In some embodiments, the compounds disclosed herein, and other potentially useful compounds, are screened for their biological activity (e.g., ability to block *Enterococcus faecalis*, *Staphylococcus aureus*, *Staphylococcus epidermidis*, *Streptococcus viridans*, *Escherichia coli*, *Klebsiella pneumoniae*, *Proteus mirabilis*, and *Pseudomonas aeruginosa*, other gram positive and gram negative bacteria in biofilms and in virulence factor production).

In some embodiments, structure-based virtual screening methodologies are contemplated for identifying bacterial inhibitors. For example, in some embodiments, molecular modeling is used to identify inhibitors.

In some embodiments, compounds are screened in cell culture or in vivo (e.g., non-human or human mammals) for their ability to inhibit biofilm formation by *S. aureus* or *S. epidermidis* and/or bacterial virulence. In some embodiments, screens detecting expression or inhibition of expression of downstream signaling molecules.

In some embodiments, the screening methods described in the experimental section below are utilized. For example, in some embodiments, high throughput screens in bacteria are performed. In one embodiment, high throughput screening is performed in *E. coli* utilizing an antibiotic resistance or other marker. In other embodiments, a high throughput assay is utilized. Compounds are screened for their ability to inhibit the growth of bacteria. In some embodiments, compounds are screened for their ability in kill or inhibit the growth or formation of biofilms and virulence factor production by bacteria. In some embodiments, dose response assays are performed.

In some embodiments, compounds identified in the bacterial screening assays above are further screened in animals. For example, in some embodiments, a mouse model of *S. epidermidis* in biofilm infection is used in screening assays.

IV. Methods

A. Methods for Treating Pneumonia in a Subject in Need Thereof.

In another embodiment, the present disclosure is directed to methods for treating pneumonia in a subject in need thereof. The method includes administering a composition comprising a compound having the structure of Formula V

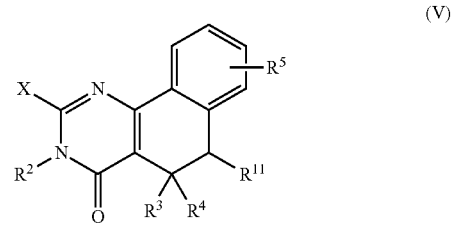

wherein X is $SR^1$, $NH_2$, $NHR^1$, $NR^1R$, OH, $OR^1$, or Cl; wherein R, $R^1$ and $R^2$ are, independently, H, a C1-C8 alkyl or alkenyl or cycloalkyl, optionally substituted with F, CN, $OR^6$, $NR^6{}_2$, $COR^6$, $CO_2R^6$, $CONHR^6$, aryl or heteroaryl, wherein one or more alkyl carbons may be replaced by O; $R^3$ and $R^4$ are, independently, a C1-C8 alkyl; $R^5$ is H, C1-C6 alkyl, CN, $OR^6$, $NR^6{}_2$, $COR^6$, $CO_2R^6$, $CONHR^6$, aryl, heteroaryl, $SO_2R^6$, $NHCOR^6$, $SO_2NHR^6$, or $OCOR^6$; $R^6$ is H, C1-C6 alkyl, C0-C3 alkyl-aryl, or C0-C3 alkyl-heteroaryl, all optionally substituted; and $R^{11}$ is H or a C1 alkyl.

Suitable exemplary compounds include:

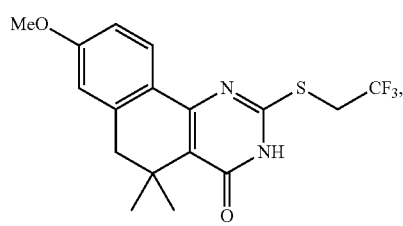

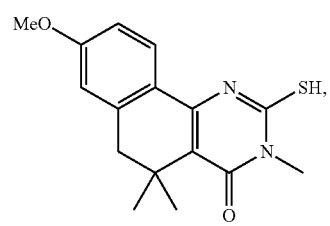

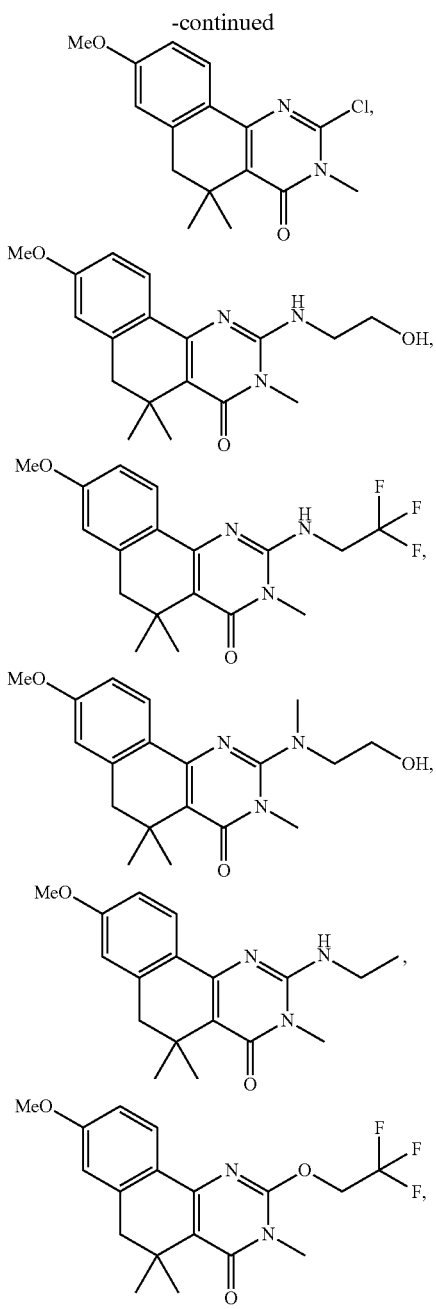

and combinations thereof.

The composition is suitably administered orally, rectally, nasally, topically (including transdermal, buccal and sublingual), vaginally, parenterally (including subcutaneous, intramuscular, intravenous and intradermal) and pulmonary administration.

The method can further include administering an antibiotic. Suitable antibiotics include a cell wall synthesis inhibitor, a bacterial DNA synthesis inhibitor, a bacterial RNA synthesis inhibitor, a bacterial lipid synthesis inhibitor, a bacterial protein synthesis inhibitor, and combinations thereof. The cell wall synthesis inhibitor is selected from the group consisting of The cell wall synthesis inhibitor is selected from β-Lactam antibiotics and glycopeptide antibiotics such as, for example, penicillin derivatives, cephalosporins (cephems), monobactams, and carbapenems, vancomycin, teicoplanin, telavancin, bleomycin, ramoplanin, and decaplanin, for example. The bacterial DNA synthesis inhibitor is selected from Quinolones and Metronidazole such as Nalidixic acid, ciprofloxacin, levofloxacin, gemifloxacin and Co-trimoxazole, for example. The bacterial RNA synthesis inhibitor is selected from Bacitracin, Rifamycins, rifampin and rifapentine, for example. The bacterial lipid synthesis inhibitor is selected from Daptomycin and polymixin B, for example. The bacterial protein synthesis inhibitor is selected from tetracyclines, chloramphenicol, aminoglycosides, macrolides, such as erythromycin, Clindamycin, Puromycin, Mupirocin, Linezolid, Telithromycin, Streptogramins, Retapamulin, for example. Suitable antibiotics include, for example, amoxicillin, clindamycin, erythromycin, tetracycline, vancomycin, and combinations thereof.

The agents mechanism of action is based upon curtailing the pathogen's ability to elicit toxins and evasion mechanisms against the host's immune system. An unimpaired immune system may be able to fight off the infection on its own. Alternatively, a boost in the form of a low-dose conventional antibiotic in combination with an antivirulence agent may become a successful strategy against more invasive infections. Antivirulence therapy offers the attractive prospect of bringing back conventional and affordable antibiotics into the clinic.

Antivirulence compounds can be administered in combination with the compounds disclosed herein. Exemplary antibacterial therapeutics include, but are not limited to, colloidal silver, penicillin, penicillin G, erythromycin, polymyxin B, viomycin, Chloromycetin, streptomycins, cefazolin, ampicillin, methicillin, oxacillin, nafcillin, cloxacillin, dicloxacillin, telavancin azactam, tobramycin, cephalosporins (including cephalothin, cefazolin, cephalexin, cephradine, cefamandole, ceftaroline, cefoxitin, and 3rd-generation cephalosporins), carbapenems (including imipenem, meropenem, Biapenem), bacitracin, tetracycline, doxycycline, gentamycin, quinolines, neomycin, clindamycin, kanamycin, Plazomicin, metronidazole, treptogramins (including Quinupristin/dalfopristun (SYNERCID™) Streptomycin, Ceftriaxone, Cefotaxime, Rifampin, glycopeptides (including vancomycin, teicoplanin, Ortivancin, dalbavancin, macrolides (including erythromycin, clarithromycin, azithromycin, lincomycin, and clindamycin), ketolides (including Telithromycin, Cethromycin), novel tetracyclines, such as Omadacycline, Eravacycline; glycylcyclines (including Terbutyl-minocyclinetigecycline; aminoglyco sides, chloramphenicol, Imipenem-cilastatin, fluoroquinolones (including ofloxacin, sparfioxacin, gemifloxacin, avarofloxacin, cinafloxacun, sitafloxacin and other topoisomerase inhibitors, DNA gyrase inhibitors including Avarofloxacin, Nemonoxacin, Zabofloxacin, Delafloxacin; Trimethoprim-sulfamethoxazole (TMP-SMX), Ciprofloxacin, topical mupirocin, Oxazolidinones (including Posizolid, Linezolid (ZYVOX™)), Lipopeptides (including Daptomycin, Ramoplanin), Telavancin, isoniazid (INN), rifampin (RIF), pyrazinamide (PZA), Ethambutol (EMB), Capreomycin, cycloserine, ethionamide (ETH), kanamycun, and p-aminosalicylic acid (PAS).

The combination of an antivirulence agent with one or more of the compounds disclosed herein in a method and/or composition of the present invention may reduce the amount of either pharmaceutical compound needed as a therapeutically effective dosage, and thereby reduce any negative side effects the agents may induce in vivo. In addition, the combination of an antivirulence agent with one or more of the compounds disclosed herein in a method and/or composition described herein may reduce the MIC (minimum inhibitory concentration) of the antibacterial therapeutic, which in turn reduces the opportunity for microbial resistance to specific antibacterial therapeutics. Combination therapies may involve co-administration or sequential administration of the pharmaceutically active components.

B. Methods for Reducing Bacterial Virulence in a Subject in Need Thereof.

In another embodiment, the present disclosure is directed to methods for reducing bacterial virulence in a subject in need thereof. The method includes administering a composition comprising a compound having the structure of Formula V, as described herein. Suitable exemplary compounds include those described herein.

The composition is suitably administered using administration methods described herein.

The method can further include administering an antibiotic. Suitable antibiotics include a cell wall synthesis inhibitor, a bacterial DNA synthesis inhibitor, a bacterial RNA synthesis inhibitor, a bacterial lipid synthesis inhibitor, a bacterial protein synthesis inhibitor, and combinations thereof, as described herein.

C. Methods for Treating a Bacterial Wound Infection in a Subject in Need Thereof.

In another embodiment, the present disclosure is directed to methods for treating a bacterial wound infection in a subject in need thereof. The method includes administering a composition comprising a compound having the structure of Formula V, as described herein. Suitable exemplary compounds include those described herein.

The composition is suitably administered using administration methods described herein.

The method can further include administering an antibiotic. Suitable antibiotics include a cell wall synthesis inhibitor, a bacterial DNA synthesis inhibitor, a bacterial RNA synthesis inhibitor, a bacterial lipid synthesis inhibitor, a bacterial protein synthesis inhibitor, and combinations thereof, as described herein.

D. Methods for Treating a Urinary Tract Infection in a Subject in Need Thereof.

In another embodiment, the present disclosure is directed to methods for treating a urinary tract infection in a subject in need thereof. The method includes administering a composition comprising a compound having the structure of Formula V, as described herein. Suitable exemplary compounds include those described herein.

The composition is suitably administered using administration methods described herein.

The method can further include administering an antibiotic. Suitable antibiotics include a cell wall synthesis inhibitor, a bacterial DNA synthesis inhibitor, a bacterial RNA synthesis inhibitor, a bacterial lipid synthesis inhibitor, a bacterial protein synthesis inhibitor, and combinations thereof, as described herein.

E. Methods for Treating a Bacterial Infection, Wherein the Bacterial Infection has or is Suspected of Having an Antibiotic-Resistant Bacteria.

In another embodiment, the present disclosure is directed to methods for treating a bacterial infection, wherein the bacterial infection has or is suspected of having an antibiotic-resistant bacteria. The method includes administering a composition comprising a compound having the structure of Formula V, as described herein. Suitable exemplary compounds include those described herein.

The composition is suitably administered using administration methods described herein.

The method can further include administering an antibiotic. Suitable antibiotics include a cell wall synthesis inhibitor, a bacterial DNA synthesis inhibitor, a bacterial RNA synthesis inhibitor, a bacterial lipid synthesis inhibitor, a bacterial protein synthesis inhibitor, and combinations thereof, as described herein.

V. Coated Surfaces

In another embodiment, the present disclosure is directed to a surface coated with a composition comprising a compound of Formula V. Suitable exemplary compounds include those described herein. Suitable surfaces include a surface of a medical device.

VI. Topical Formulations

In another aspect, the present disclosure is directed to a topical formulation for treating a bacterial infection. The topical formulation can be formulated as an ointment, a cream (oil-in-water emulsion), and a lotion. The composition includes: a compound having the structure of Formula V

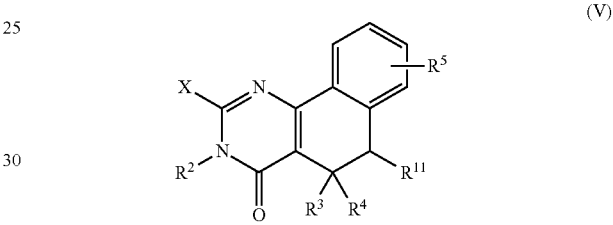

wherein X is $SR^1$, $NH_2$, $NHR^1$, $NR^1R$, OH, $OR^1$, or Cl; wherein R, $R^1$ and $R^2$ are, independently, H, a C1-C8 alkyl or alkenyl or cycloalkyl, optionally substituted with F, CN, $OR^6$, $NR^6_2$, $COR^6$, $CO_2R^6$, $CONHR^6$, aryl or heteroaryl, wherein one or more alkyl carbons may be replaced by O; $R^3$ and $R^4$ are, independently, a C1-C8 alkyl; $R^5$ is H, C1-C6 alkyl, CN, $OR^6$, $NR^6_2$, $COR^6$, $CO_2R^6$, $CONHR^6$, aryl, heteroaryl, $SO_2R^6$, $NHCOR^6$, $SO_2NHR^6$, or $OCOR^6$; $R^6$ is H, C1-C6 alkyl, C0-C3 alkyl-aryl, or C0-C3 alkyl-heteroaryl, all optionally substituted; and $R^{11}$ is H or a C1 alkyl; and a base.

Suitable compounds for the composition include

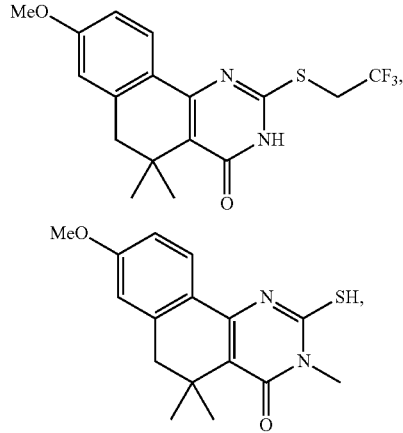

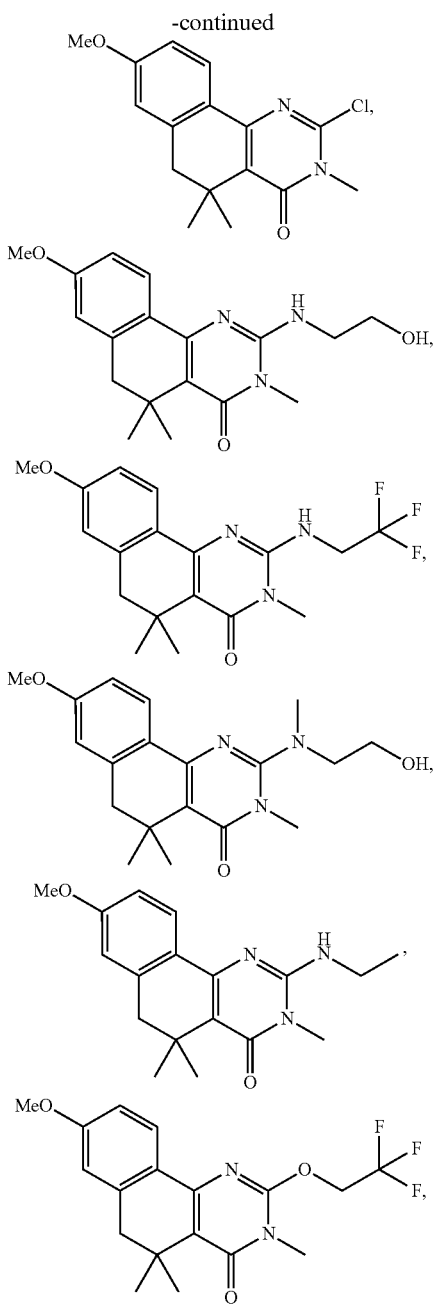

and combinations thereof.

The topical composition includes about 0.05 wt. % to about 5.0 wt. % of the compound having the structure of Formula V.

The topical composition further includes a base. Suitable bases include hydrocarbon bases. Suitable hydrocarbon bases include liquid paraffin, white petrolatum, waxes, esters of fatty alcohols, saturated fatty acids, oleic acid, olive oil, starch glycerin, purified lanolin, cetyl alcohol, glyceryl monostearate, methylparaben, propylparaben, glycol ethers, gelation hydrocarbon, polyethylene glycol, polyoxyl 40 stearate, polysorbates, hydrophilic ointment base, ceresine, white ointment base, absorptive ointment base, Macrogol ointment base, simple ointment base, beeswax, wool fat and combinations thereof. Suitable bases also include oils. Suitable oils include vegetable oils. Suitable vegetables oils include olive oil, coconut oil, sesame oil, almond oil, peanut oil, and combinations thereof.

The topical composition can further include an excipient. Suitable excipients include antiseptics, surfactants, stabilizers, alcohols, esters, oils, emulsifiers, absorption enhances, solubility enhancers and combinations thereof.

The topical composition can further include a stabilizer. As used herein, the term "stabilizer" refers to compounds such as any antioxidation agents, buffers, acids, preservatives and the like that are compatible with the other components of the topical ointment compositions. Stabilizers include agents that can improve the compatibility of excipients with a container, or a delivery system, including a syringe or a glass bottle, improve the stability of a component of the composition, and improve formulation stability. Vegetable oils can also be used to solubilize the compounds (olive oil, coconut oil, sesame oil, almond oil, and peanut oil for example).

The topical composition can further include a penetration enhancer. Penetration enhancers serve to improve the absorption of the compound having the structure of Formula V across the skin of the subject.

The topical composition may further include a preservative to prevent bacterial and fungal growth in the product.

VII. Methods of Treating Bacterial Infections

In another aspect, the present disclosure is directed to a method of treating a bacterial infection in a subject in need thereof. The method includes applying to the subject in need thereof a topical formulation including: a compound having the structure of Formula V

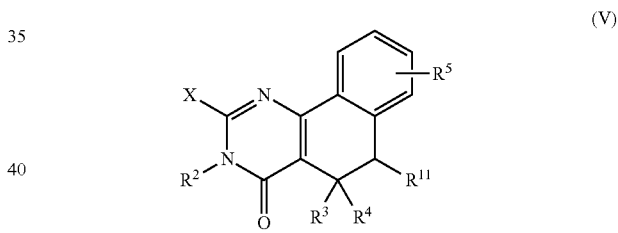

wherein X is $SR^1$, $NH_2$, $NHR^1$, $NR^1R$, OH, $OR^1$, or Cl; wherein R, $R^1$ and $R^2$ are, independently, H, a C1-C8 alkyl or alkenyl or cycloalkyl, optionally substituted with F, CN, $OR^6$, $NR^6_2$, $COR^6$, $CO_2R^6$, $CONHR^6$, aryl or heteroaryl, wherein one or more alkyl carbons may be replaced by O; $R^3$ and $R^4$ are, independently, a C1-C8 alkyl; $R^5$ is H, C1-C6 alkyl, CN, $OR^6$, $NR^6_2$, $COR^6$, $CO_2R^6$, $CONHR^6$, aryl, heteroaryl, $SO_2R^6$, $NHCOR^6$, $SO_2NHR^6$, or $OCOR^6$; $R^6$ is H, C1-C6 alkyl, C0-C3 alkyl-aryl, or C0-C3 alkyl-heteroaryl, all optionally substituted; and $R^{11}$ is H or a C1 alkyl; and a base.

Suitable compounds include

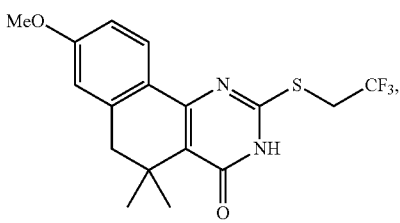

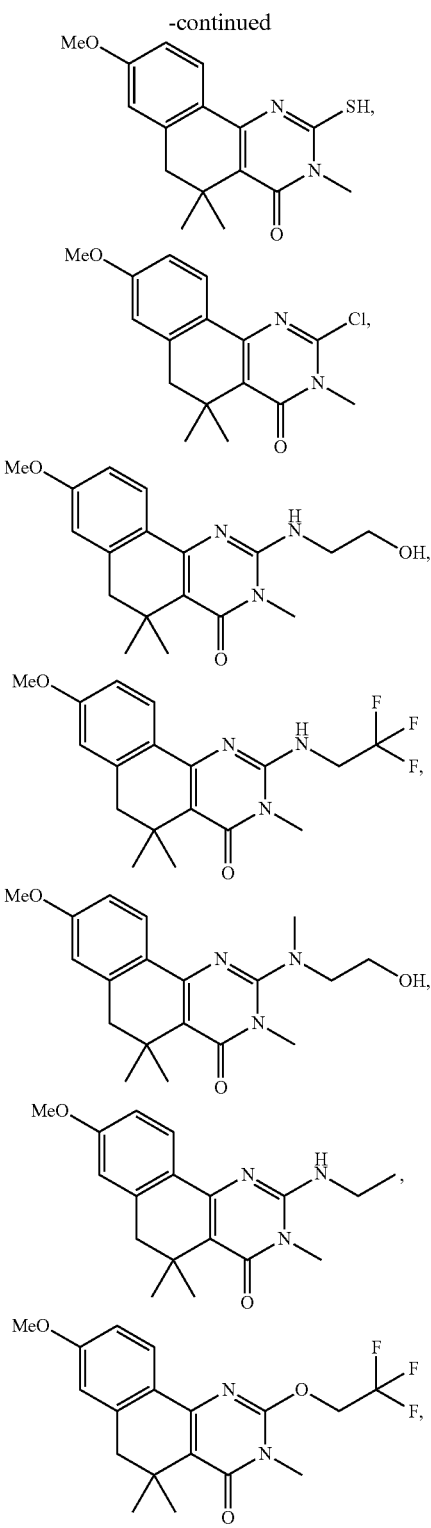

and combinations thereof.

The topical formulation includes about 0.05 wt. % to about 5.0 wt. % of the compound having the structure of Formula V.

The topical formulation can be applied to a subject's epidermis layer, dermis layer, subcutaneous tissue layer, muscle, bone, and combinations thereof.

The topical formulation can be applied one or more times per day.

The topical formulation provides a therapeutically effective amount of the compound having the structure of Formula V. The terms "effective amount" and "therapeutically effective amount," as used herein, refer to a sufficient amount of the compound having the structure of Formula V being delivered that would be expected to relieve to some extent one or more of the symptoms of the disease or condition being treated. For example, the result of administration of the compound having the structure of Formula V disclosed herein is reduction and/or alleviation of the signs, symptoms, or causes of a bacterial infection. For example, an "effective amount" for therapeutic uses is the amount of the compound having the structure of Formula V, including a formulation as disclosed herein required to provide a decrease or amelioration in disease symptoms without undue adverse side effects. The term "therapeutically effective amount" includes, for example, a prophylactically effective amount. An "effective amount" of the compound having the structure of Formula V disclosed herein is an amount effective to achieve a desired pharmacologic effect or therapeutic improvement without undue adverse side effects. It is understood that "an effective amount" or "a therapeutically effective amount" varies, in some embodiments, from subject to subject, due to variation in metabolism of the compound administered, age, weight, general condition of the subject, the condition being treated, the severity of the condition being treated, and the judgment of the prescribing physician. It is also understood that "an effective amount" in an extended-release dosing format may differ from "an effective amount" in an immediate release dosing format based upon pharmacokinetic and pharmacodynamic considerations.

The bacterial infection can be impetigo, ecthyma, Staphylococcal scalded skin syndrome (SSSS), erysipelas, cellulitis, abscess, necrotizing fasciitis, folliculitis, furunculosis, carbunculosis, secondary skin infection, surgical wounds, traumatic wounds, diabetic ulcers, venous ulcers, and combinations thereof.

The bacterial infection can be caused by or complicated by Gram positive bacteria. Gram positive bacteria include *Enterococcus faecalis, Staphylococcus aureus, Staphylococcus epidermidis*, methicillin-resistant *Staphylococcus aureus* (MRSA), methicillin-resistant *Staphylococcus epidermidis* (MRSE), *Streptococcus pyogenes, Streptococcus agalactiae*, and combinations thereof.

The bacterial infection can be caused by or complicated by a Gram negative bacteria. Gram negative bacteria include *Escherichia coli, Klebsiella pneumoniae, Proteus mirabilis*, and *Pseudomonas aeruginosa, Acinetobacter baumannii* and combinations thereof.

The method can further include administering to the subject an antibiotic. Suitable antibiotics include a cell wall synthesis inhibitor, a bacterial DNA synthesis inhibitor, a bacterial RNA synthesis inhibitor, a bacterial lipid synthesis inhibitor, a bacterial protein synthesis inhibitor, and combinations thereof. The cell wall synthesis inhibitor is selected from β-Lactam antibiotics and glycopeptide antibiotics such as, for example, penicillin derivatives, cephalosporins (cephems), monobactams, and carbapenems, vancomycin, teicoplanin, telavancin, bleomycin, ramoplanin, and decaplanin, for example. The bacterial DNA synthesis inhibitor is selected from Quinolones and Metronidazole such as Nalidixic acid, ciprofloxacin, levofloxacin, gemifloxacin and Co-trimoxazole, for example. The bacterial RNA synthesis inhibitor is selected from Bacitracin, Rifamycins, rifampin and rifapentine, for example. The bacterial lipid synthesis inhibitor is selected from Daptomycin and polymixin B, for example. The bacterial protein synthesis inhibitor is selected from tetracyclines, chloramphenicol, aminoglycosides, macrolides, such as erythromycin, Clindamycin, Puromycin, Mupirocin, Linezolid, Telithromycin, Streptogramins, Retapamulin, for example. Suitable antibiotics include, for example, amoxicillin, clindamycin, erythromycin, tetracycline, vancomycin, and combinations thereof.

EXAMPLES

The following examples are provided to demonstrate and further illustrate certain embodiments of the present disclosure and are not to be construed as limiting the scope thereof.

Example 1

A chemical series of small molecular weight chemical compounds that are capable of inhibiting biofilm formation by S. aureus and S. epidermidis on different biomaterial surfaces were identified (Tables 1-4). These compounds are different from existing antibiotics or compounds under development by others in that they do not kill bacteria or inhibit bacterial growth but instead alter patterns of gene expression leading to reduced virulence.

Additional non-bactericidal anti-staphylococcus reagents for application to the surface of biomaterials used for making implantable medical devices, especially artificial heart valves, pacemakers, and catheters, to prevent or treat biofilm formation without resistance development are developed. These compounds can also be used to treat infections caused by S. aureus and/or S. epidermidis since they inhibit the gene expression of a number of important virulence factors.

Figure 1B:
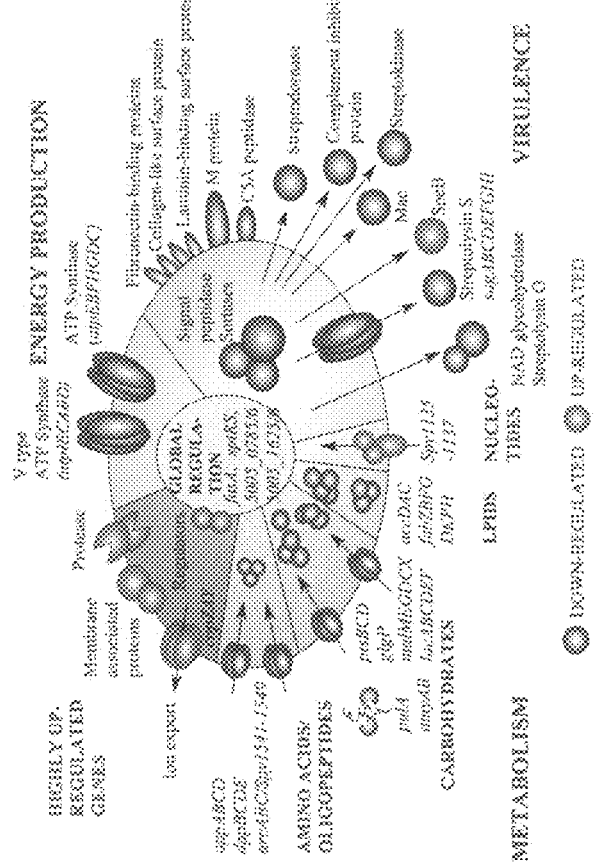

An antivirulence approach was used to screen for small molecules that can inhibit streptokinase (SK) expression with low toxicity to Group A Streptococcus (GAS), based on previous work demonstrating that SK is a key virulence factor for GAS infection. A number of small molecules that can inhibit SK expression without impeding bacterial growth were evaluated. Furthermore, these compounds can inhibit gene expression of a broad spectrum of streptococcal virulence factors (FIG. 1A). One compound (CCG-2979) is capable of protecting mice against group A streptococcal infection (FIG. 1B).

Figure 2A:
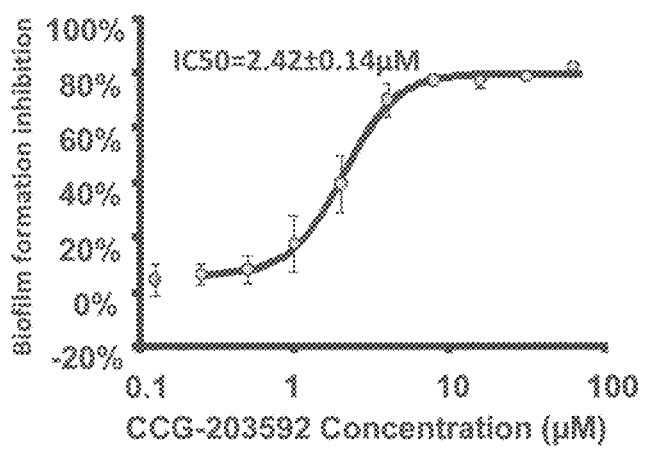
FIGS. 2A-2E show compounds that inhibit *staphylococcus* virulence.
Figure 2B:
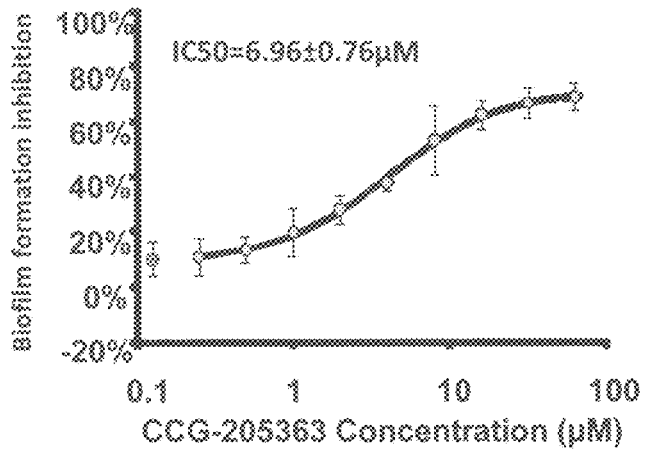
Figure 4:
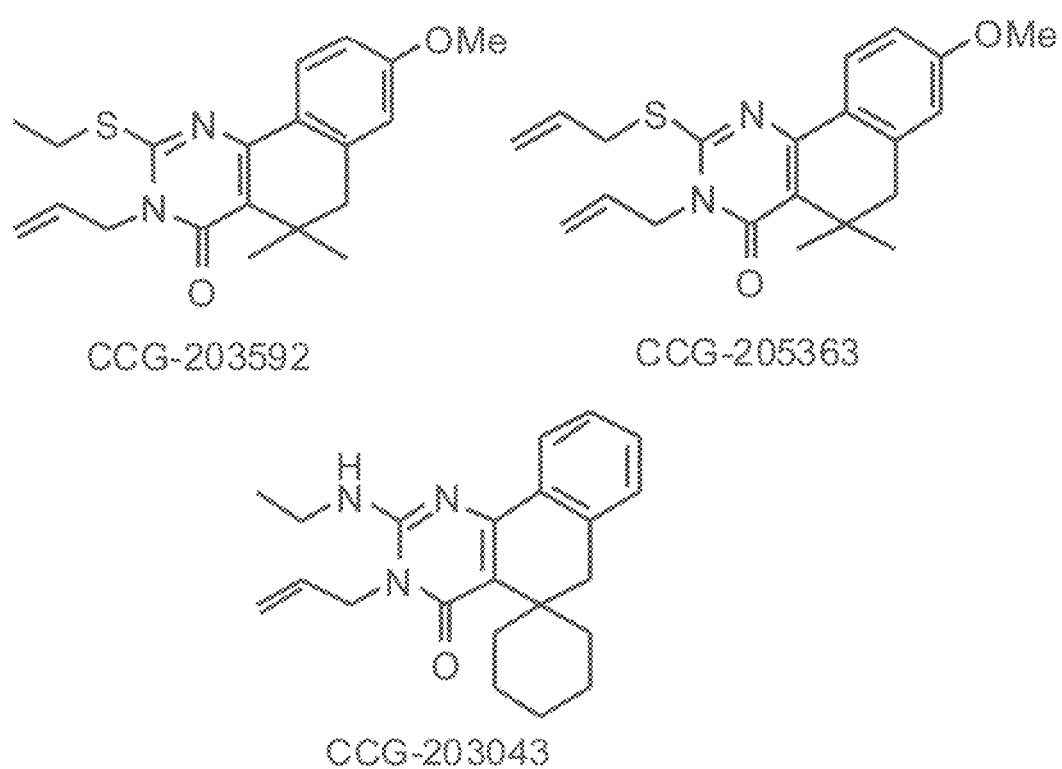
FIG. 4 shows structures of exemplary biofilm inhibitors.
Figure 5A:
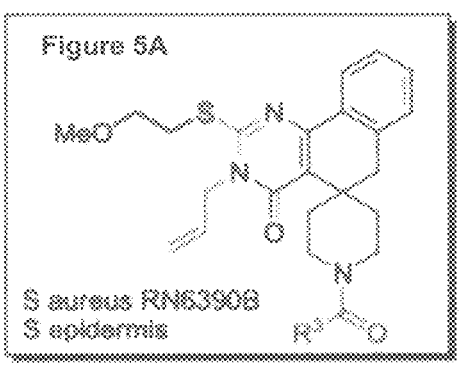
FIGS. 5A-5D show structures of exemplary biofilm inhibitors.
Figure 5B:
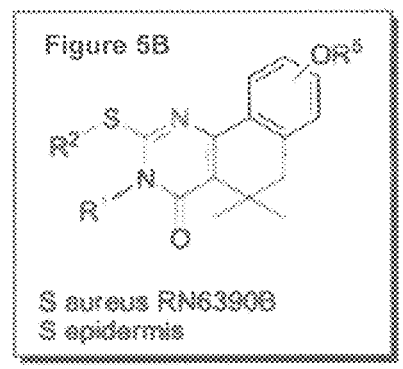
Figure 5C:
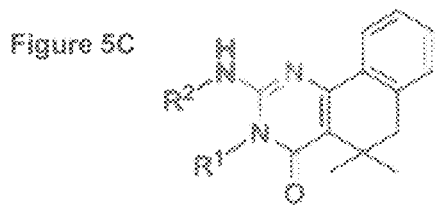
Figure 5D:
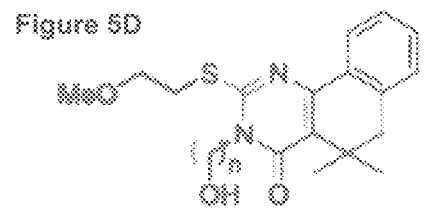

These compounds were then tested on staphylococcus biofilm formation. Out of 68 analogs tested for their effects on S. aureus Newman biofilm formation in microtiter plates, two demonstrated consistent inhibition without significantly bacteria inhibiting growth. The two compounds (CCG-203592 and CCG-205363) were tested on S. aurues strain RN6390, which is reported to be more prone to biofilm formation than Newman strain. Both compounds demonstrated strong inhibition of RN6390 biofilm formation in microtiter plate (1050=2.42±0.14 µM for CCG-203592, IC50=6.96±0.76 µM for CCG-205363) (FIGS. 2A and B) without inhibiting bacteria growth at 20 µM. Structures of these inhibitors are shown in FIG. 4.

Figure 2C:
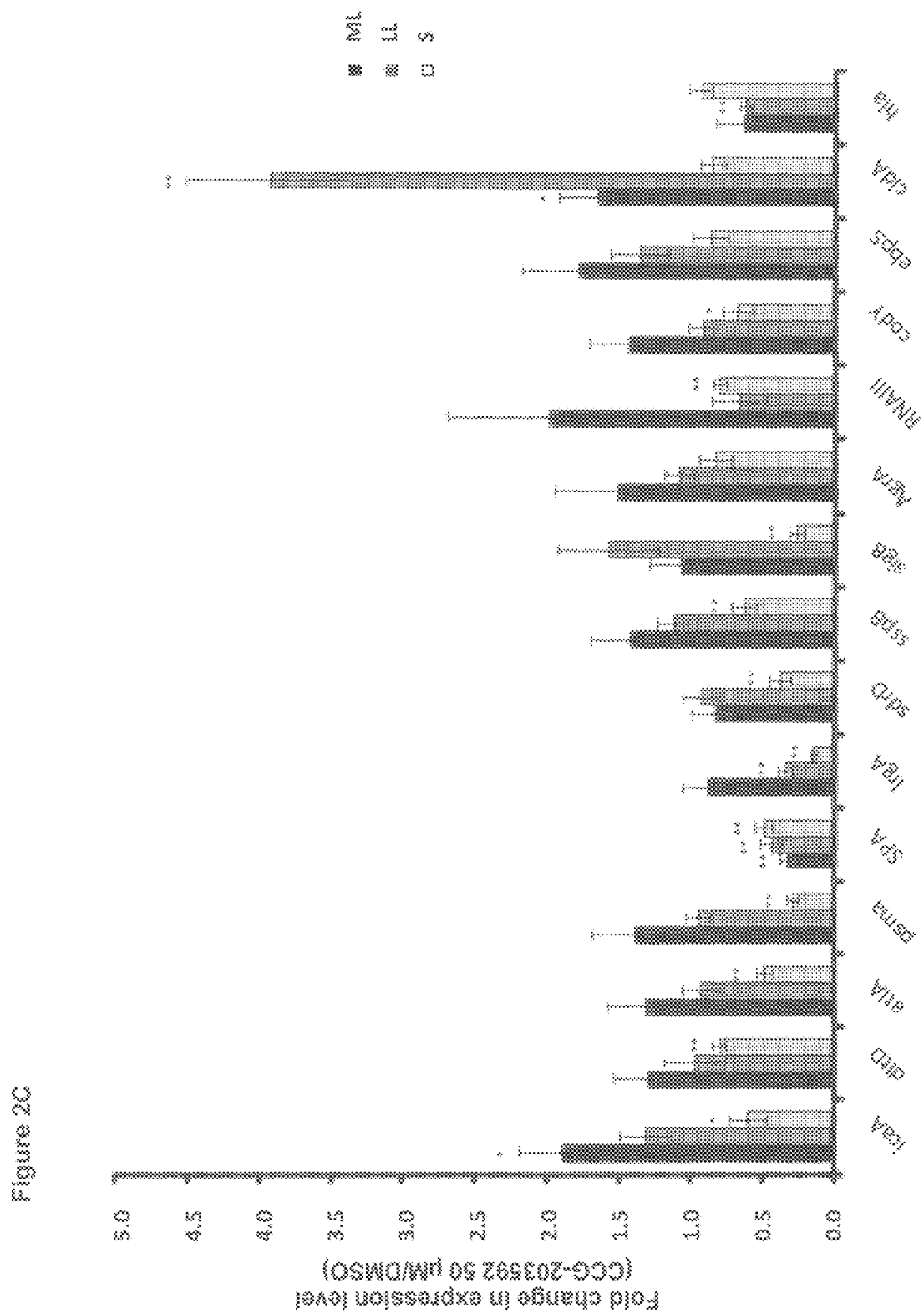
Figure 2D:
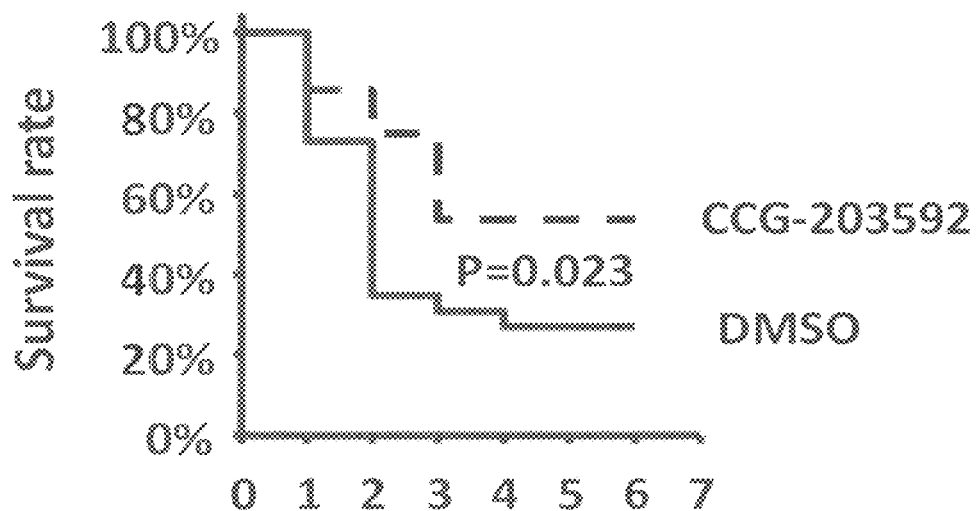
Figure 2E:
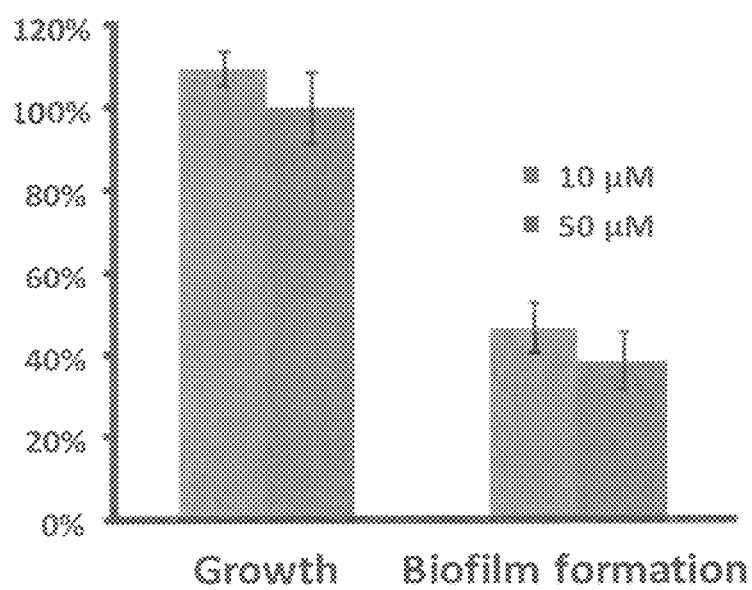

A group of S. aureus virulence factor genes were tested for their response to CCG-203592 treatment by real time RT-PCR. Several virulence factor genes were down regulated by CCG-203592 (FIG. 2C), including genes (atl and psm) that are important for S. aureus biofilm formation and structuring. Protein A (SPA) which is an important virulence factor was also inhibited, suggesting potential of the small compound as an anti-virulence reagent. The broad impact of CCG-203592 on S. aureus gene expression indicated that it could also protect a host against S. aureus infection, which was supported by its in vivo efficacy in protecting mice in a S. aureus lung infection model (FIG. 2D). An analog from the same chemical series (CCG-203043) exhibited strong inhibition of S. epidermidis biofilm formation without inhibition of bacterial growth (FIG. 2E).

Figure 3:
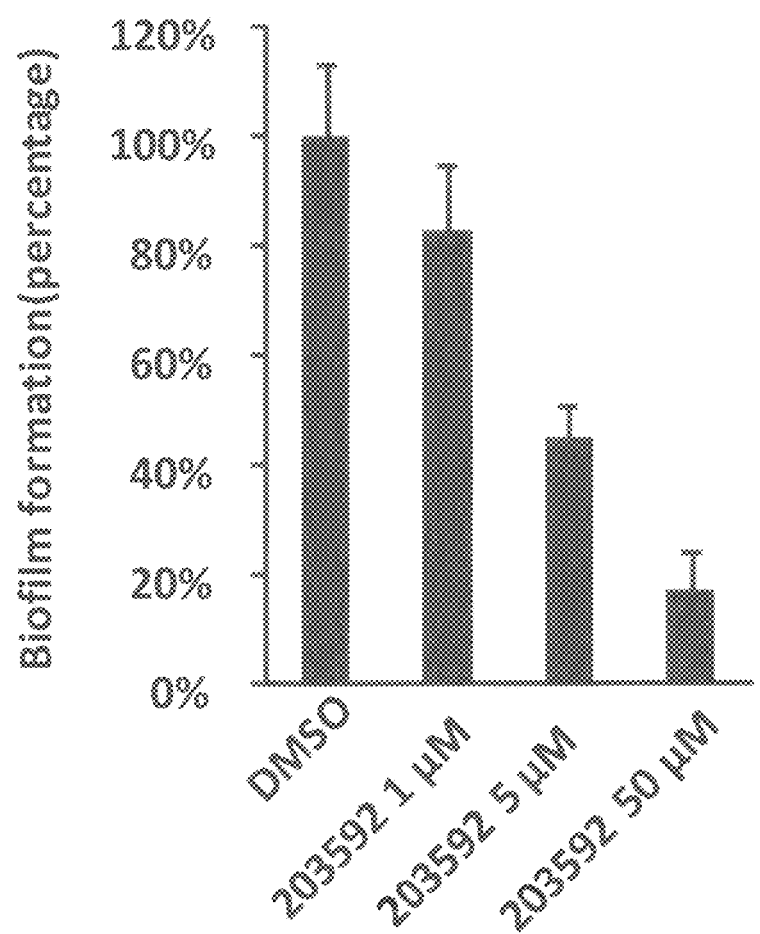
FIG. 3 shows compound CCG-203592 in inhibited *S. aureus* RN6390 strain biofilm formation on medical grade silicone sheet.

CCG-203592 also decreased biofilm formation on the surface of silicone sheet (FIG. 3) which is widely used in medical devices.

Several compounds from the CCG-2979 series can inhibit either S. aureus or S. epidermidis biofilm formation while also inhibiting group A streptococcus SK gene expression.

Structure activity relationship (SAR) studies are carried out on 200-300 new analogs to identify the most effective inhibitors of biofilm formation.

Over 110 new analogs related to CCG-2979 were synthesized. All of these were assayed for biofilm inhibition at 100 µM, and only a small subset was active at inhibiting biofilm formation without inhibiting bacterial growth: S. aureus (14 analogs); S. epidermis (7 analogs). Three of the most potent analogs are depicted in FIG. 4. All 21 of the active analogs could be grouped into four clusters represented by templates A-D (FIG. 5), and only two of these (A and B, boxed in FIG. 5) represent analogs active against both strains.

Analogs of these two series are synthesized. An exemplary synthesis of analogs of A is presented in FIG. 6. Commercially available acrylate 1 is converted to tricyclic amino ester 2 with 2-methylbenzonitrile under basic conditions (32), which can then be further cyclized to thiourea 3 with various isothiocyanates under a variety of conditions (33).

Alkylation of the sulfur with diverse alkylating agents and subsequent removal of the N-Boc group under acidic conditions affords the intermediate secondary amine 4. Finally, the amine can be acylated, sulfonylated or reductively alkylated under standard conditions.

Preparation of new analogs based on template B follows the same general route, starting with dimethylacrylate 6 and various alkoxy-2-methylbenzonitriles 7 (FIG. 7). Hybrid analogs bearing key elements of templates A and B (e.g. E in FIG. 7) are also prepared. The synthetic route to these compounds is identical to that used for template A (FIG. 6), replacing 2-methylbenzonitrile with alkoxy-2-methylbenzonitriles 7.

The new analogs in FIGS. 6 and 7 are integrated into a multi-layer coating on biomaterials for controlled release to inhibit biofilm formation. An alternative method for delivery is covalent linkage of biofilm inhibitors to the biomaterial surface, which would be expected to result in a much longer duration of protection. It has previously been shown that vancomycin, covalently bound to a titanium surface, is effective at killing S. aureus and preventing biofilm formation by S. epidermis (21;34). This is possible because vancomycin works at the surface of the cell wall rather than needing to penetrate into the bacteria.

Figure 8:
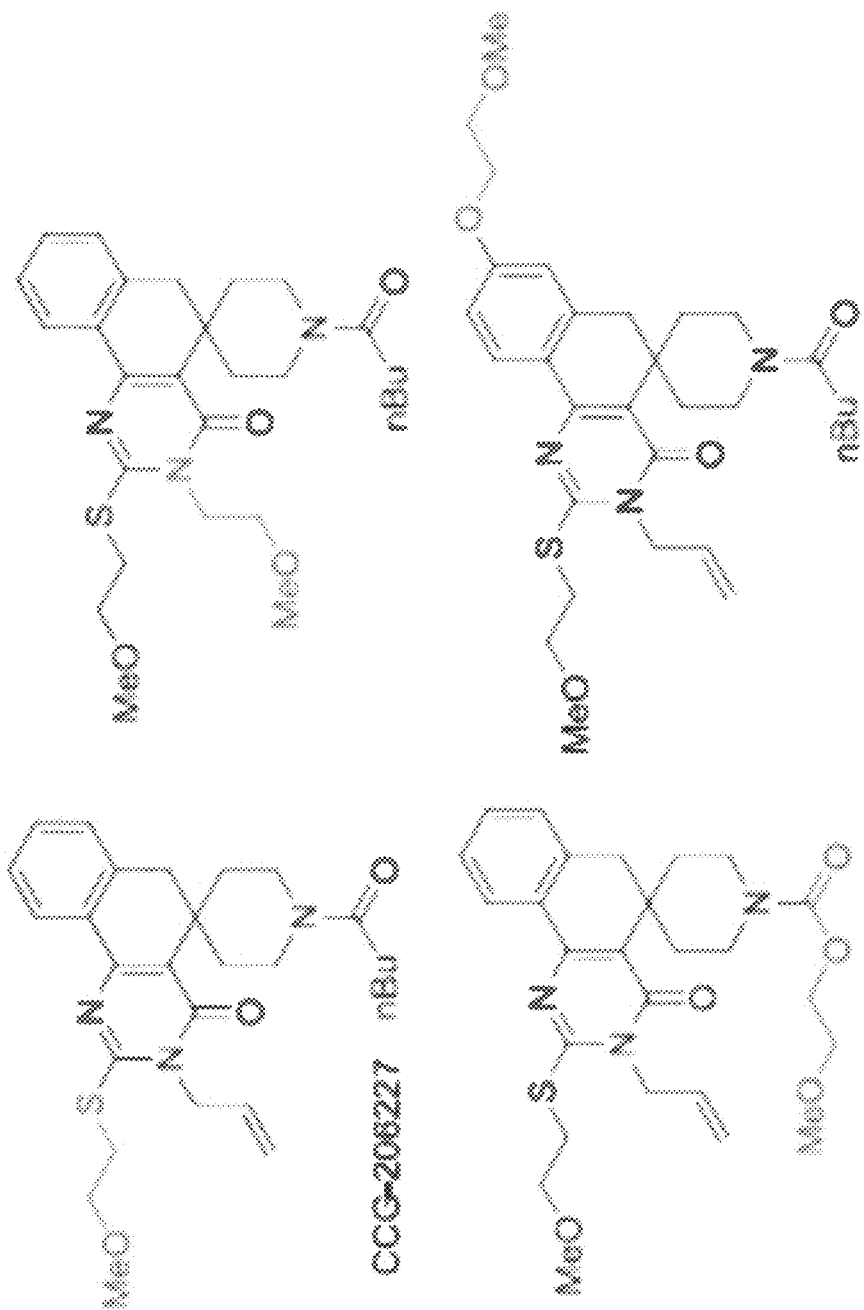
FIG. 8 shows structures of exemplary biofilm inhibitors.
Figure 9:
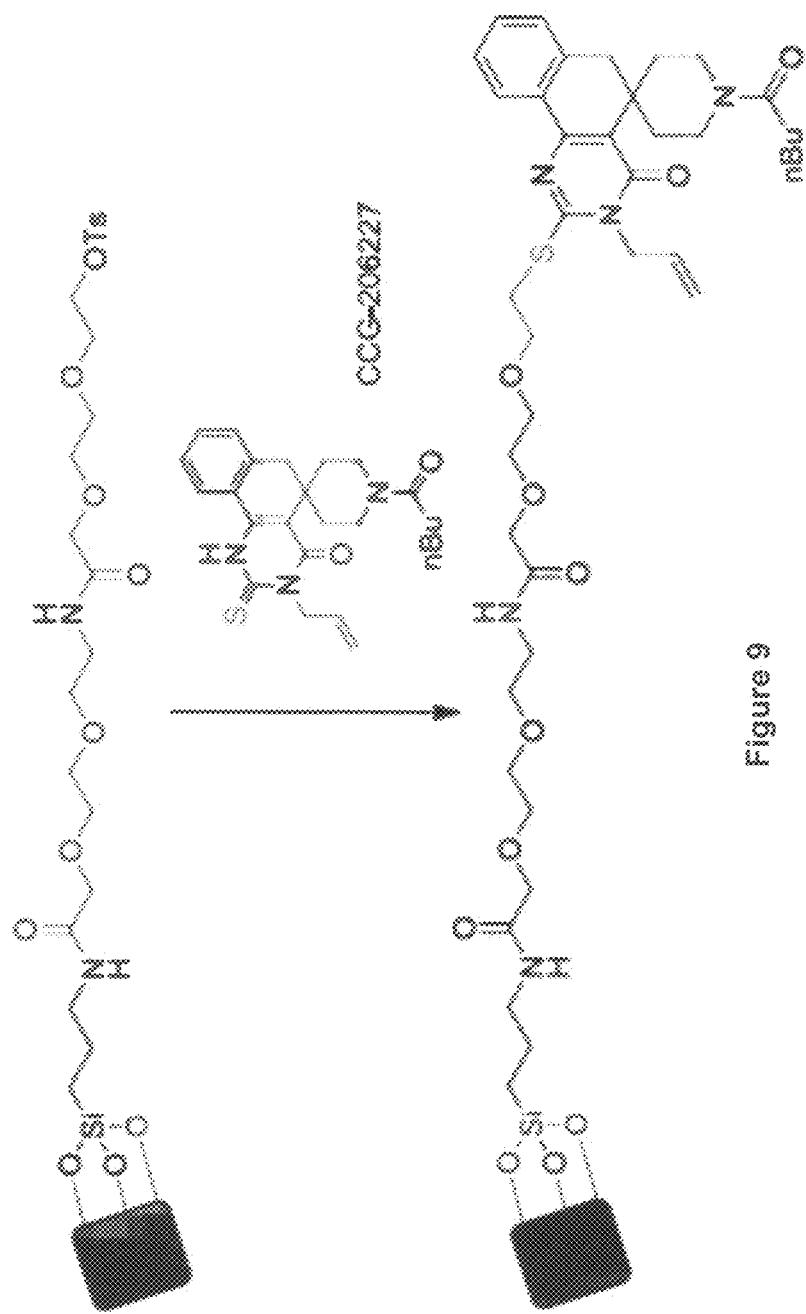
FIG. 9 shows synthesis of exemplary biofilm inhibitors.

Analogs of CCG-206227, which have been shown to inhibit biofilm formation by both S. aureus and S. epidermis, that move the S-methoxyethyl group to other points on the template (shown in FIG. 8) are prepared. Those analogs retaining activity indicate where covalent linking to the biomaterial through a PEG linker would most likely be possible without loss of anti-biofilm activity. The active analogs are attached to biomaterial through longer PEG tethers. For example, attachment of active analog CCG-206227 to a biomaterial is accomplished as shown in FIG. 9.

Example 2

Biofilm Inhibitors

The compounds described in Tables 1-4 find use in the inhibition of biofilm formation by a variety of organisms.

Table 1 shows inhibition of *S. epidermis* biofilm. Table 2 shows inhibition of *S. aureus* biofilm. Table 3 shows compounds with >20% inhibition of *S. aureus* biofilm at 100 or 50 µM. Table 4 shows compounds with >20% inhibition of *S. epidermis* biofilm at 100 or 50 µM.

TABLE 1

*S. epidermis* Biofilm inhibition

| CCG-No. | 5 µM vs. (−) Control | 10 µM vs. (−) Control | 50 µM vs. (−) Control | 100 µM vs. (−) Control | Growth inhibition 100 µM vs. (−) Control |
|---|---|---|---|---|---|
| 102483 | | | | 0.786 | 1.286 |
| 203043 | | | | 0.402 | 1.183 |
| 203043 | | | | 0.437 | 0.890 |
| 203043 | | 0.169 | | 0.45 | 1.03 |
| 203804 | | | | 0.079 | 1.034 |
| 203804 | | 0.858 | | 0.15 | 0.90 |
| 203804 | | | | 0.252 | 1.006 |
| 204030 | | | | 0.739 | 1.108 |
| 204033 | | | | 0.756 | 1.026 |
| 205381 | | | | 0.111 | 0.843 |
| 205381 | | | | 0.756 | 0.553 |
| 205384 | | | | 0.058 | 1.001 |
| 205384 | | 1.095 | | 0.20 | 0.92 |
| 205384 | | | | 0.234 | 1.014 |
| 205390 | | | | 0.082 | 1.350 |
| 205390 | | 0.921 | | 0.16 | 1.09 |
| 205390 | | | | 0.295 | 1.069 |
| 205396 | | | | 0.037 | 0.130 |
| 205427 | | | | 0.766 | 0.980 |
| 205447 | | 0.936 | | 0.18 | 1.04 |
| 205447 | | | | 0.281 | 0.935 |
| 205447 | | | | 0.447 | 1.006 |
| 206227 | | 0.943 | | 0.30 | 1.41 |
| 206227 | | | | 0.498 | 1.432 |
| 206227 | | | | 0.599 | 1.314 |
| 206239 | | | | 0.232 | 1.111 |
| 206239 | | | | 0.795 | 1.070 |
| 206353 | | | | 0.347 | 1.079 |
| 206353 | | 1.053 | | 0.39 | 0.83 |
| 206353 | | | | 0.428 | 0.964 |
| 206660 | 0.715 | | 0.643 | | |
| 206660 | 0.778 | | 0.727 | | |
| 206661 | 0.987 | | 0.128 | | |
| 206661 | | | 0.163 | | |
| 206661 | 1.068 | | 0.163 | | |
| 206661 | | | 0.260 | | |
| 206663 | | | 0.761 | | |
| 206663 | 0.734 | | 0.775 | | |
| 206663 | 0.672 | | 0.781 | | |
| 206664 | 0.877 | | 0.032 | | |
| 206664 | 0.869 | | 0.040 | | |
| 206664 | | | 0.094 | | |
| 206664 | | | 0.124 | | |
| 208860 | 0.850 | | 0.798 | | |
| 208982 | 0.987 | | 0.660 | | |
| 211970 | 0.79 | | 0.67 | | |
| 211971 | 1.25 | | 0.69 | | |
| 212014 | 1.05 | | 0.63 | | |
| 212015 | 0.93 | | 0.48 | | |

*Data reported as growth of biofilm or bacteria in presence of drug vs absence of drug (test/control) as measured by optical density

TABLE 2

*S. aureus* Biofilm Inhibition*

| CCG-No. | 5 µM vs. (−) Control | 10 µM vs. (−) Control | 50 µM vs. (−) Control | 100 µM vs. (−) Control | Growth Inhibition* 100 µM vs. (−) Control |
|---|---|---|---|---|---|
| 102485 | | | | 0.495 | 1.143 |
| 102491 | | | | 0.750 | 0.848 |
| 102493 | | | | 0.660 | 0.721 |
| 102495 | | | | 0.789 | 0.930 |
| 102620 | | | | 0.765 | 0.953 |
| 102622 | | | | 0.686 | 0.777 |
| 203037 | | | | 0.375 | 0.765 |
| 203039 | | | | 0.710 | 0.959 |
| 203041 | | | | 0.477 | 0.897 |
| 203043 | | | | 0.435 | 0.700 |
| 203574 | | | | 0.465 | 0.738 |
| 203592 | | | | 0.230 | 1.104 |
| 203592 | | 0.402 | | 0.35 | 0.91 |
| 203592 | | | | 0.357 | 1.014 |
| 203598 | | | | 0.610 | 0.855 |
| 203625 | | | | 0.255 | 0.949 |
| 203625 | | | | 0.383 | 0.708 |
| 203625 | | 0.513 | | 0.43 | 1.24 |
| 203625 | | | | 0.574 | 0.985 |
| 203627 | | | | 0.496 | 0.806 |
| 203629 | | | | 0.351 | 0.667 |
| 203631 | | | | 0.311 | 0.767 |
| 203633 | | | | 0.540 | 0.762 |
| 203802 | | | | 0.557 | 0.677 |
| 203803 | | | | 0.768 | 0.819 |
| 203804 | | | | 0.103 | 0.662 |
| 204027 | | | | 0.748 | 1.076 |
| 204028 | | | | 0.700 | 1.128 |
| 204029 | | | | 0.636 | 0.943 |
| 204030 | | | | 0.589 | 0.919 |
| 204031 | | | | 0.592 | 0.985 |
| 204033 | | | | 0.599 | 0.838 |
| 204036 | | | | 0.765 | 1.122 |
| 204037 | | | | 0.657 | 1.101 |
| 204040 | | | | 0.659 | 1.186 |
| 204041 | | | | 0.757 | 0.902 |
| 204060 | | | | 0.790 | 0.912 |
| 204080 | | | | 0.734 | 1.098 |
| 205353 | | | | 0.779 | 1.105 |
| 205360 | | | | 0.764 | 0.884 |
| 205361 | | | | 0.677 | 0.890 |
| 205363 | | 0.631 | | 0.44 | 0.95 |
| 205382 | | | | 0.552 | 0.934 |
| 205384 | | | | 0.160 | 0.935 |
| 205387 | | | | 0.723 | 1.151 |
| 205390 | | | | 0.525 | 0.891 |
| 205396 | | | | 0.062 | 0.111 |
| 205396 | | | | 0.073 | 0.136 |
| 205396 | | 0.684 | | 0.07 | 0.26 |
| 205426 | | | | 0.778 | 1.136 |
| 205427 | | | | 0.193 | 0.928 |
| 205427 | | 0.734 | | 0.34 | 0.97 |
| 205427 | | | | 0.537 | 0.997 |
| 205434 | | | | 0.325 | 0.622 |
| 205434 | | | | 0.355 | 0.960 |
| 205435 | | 0.293 | | 0.38 | 1.26 |
| 205435 | | | | 0.651 | 1.148 |
| 205435 | | | | 0.751 | 1.158 |
| 205444 | | | | 0.662 | 1.037 |
| 205445 | | | | 0.711 | 1.072 |
| 205447 | | | | 0.395 | 0.900 |
| 205447 | | 1.105 | | 0.50 | 1.06 |
| 205447 | | | | 0.665 | 0.980 |
| 205453 | | | | 0.796 | 1.022 |
| 205480 | | | | 0.441 | 1.149 |
| 205480 | | | | 0.622 | 1.029 |
| 205480 | | 0.523 | | 0.65 | 1.16 |
| 206176 | | | | 0.795 | 1.004 |
| 206178 | | 0.565 | | 0.43 | 1.04 |
| 206178 | | | | 0.583 | 0.977 |
| 206178 | | | | 0.794 | 1.049 |
| 206227 | | | | 0.270 | 0.785 |
| 206227 | | 0.528 | | 0.38 | 1.08 |
| 206227 | | | | 0.469 | 1.177 |

TABLE 2-continued

S. aureus Biofilm Inhibition*

| CCG-No. | 5 µM vs. (−) Control | 10 µM vs. (−) Control | 50 µM vs. (−) Control | 100 µM vs. (−) Control | Growth Inhibition* 100 µM vs. (−) Control |
|---|---|---|---|---|---|
| 206230 | | | | 0.430 | 0.970 |
| 206230 | | 0.855 | | 0.68 | 1.04 |
| 206230 | | | | 0.745 | 1.081 |
| 206231 | | 0.525 | | 0.53 | 1.11 |
| 206231 | | | | 0.529 | 1.097 |
| 206231 | | | | 0.651 | 1.101 |
| 206233 | | | .594 | | |
| 206234 | | 1.012 | | 0.65 | 0.99 |
| 206234 | | | | 0.653 | 1.038 |
| 206234 | | | | 0.773 | 0.993 |
| 206235 | | | | 0.776 | 1.063 |
| 206239 | | | | 0.327 | 0.557 |
| 206239 | | | | 0.485 | 0.974 |
| 206352 | | 0.604 | | 0.47 | 1.01 |
| 206352 | | | | 0.535 | 1.082 |
| 206352 | | | | 0.623 | 1.085 |
| 206353 | | | | 0.323 | 0.921 |
| 206353 | | | | 0.368 | 0.985 |
| 206353 | | 0.494 | | 0.40 | 1.05 |
| 206355 | | | | 0.747 | 0.960 |
| 206356 | | | | 0.591 | 1.096 |
| 206358 | | 0.557 | | 0.70 | 0.95 |
| 206358 | | | | 0.708 | 1.173 |
| 206358 | | | | 0.728 | 1.167 |
| 206660 | | | 0.601 | | |
| 206660 | 0.460 | | 0.604 | | |
| 206660 | | | 0.746 | | |
| 206661 | | | 0.262 | | |
| 206661 | 0.869 | | 0.269 | | |
| 206661 | | | 0.312 | | |
| 206661 | 0.985 | | 0.468 | | |
| 206663 | | | 0.476 | | |
| 206663 | | | 0.588 | | |
| 206663 | 0.499 | | 0.589 | | |
| 206663 | 0.608 | | 0.708 | | |
| 206664 | 0.890 | | 0.028 | | |
| 206664 | | | 0.036 | | |
| 206664 | | | 0.039 | | |
| 206664 | 1.056 | | 0.042 | | |
| 208860 | 0.704 | | 0.464 | | |
| 208863 | 0.721 | | 0.686 | | |
| 208864 | 0.495 | | 0.491 | | |
| 208865 | 0.803 | | 0.652 | | |
| 208981 | 0.885 | | 0.706 | | |
| 208982 | 0.765 | | 0.319 | | |
| 211790 | 0.381 | | 0.326 | | |
| 211793 | 1.220 | | 0.722 | | |
| 211810 | 0.682 | | 0.750 | | |
| 211811 | 0.678 | | 0.702 | | |
| 211812 | 0.752 | | 0.750 | | |
| 211970 | 0.69 | | 0.58 | | |
| 211972 | 1.25 | | 0.68 | | |
| 212010 | 0.55 | | 0.35 | | |
| 212011 | 0.48 | | 0.29 | | |
| 212012 | 0.55 | | 0.27 | | |
| 212014 | 0.77 | | 0.52 | | |
| 212015 | 0.94 | | 0.33 | | |

*Data reported as growth of biofilm or bacteria in presence of drug vs absence of drug (test/control) as measured by optical density

TABLE 3

>20% inhibition of S. aureus biofilm at 100 or 50 µM

| STRUCTURE | ID |
|---|---|
| 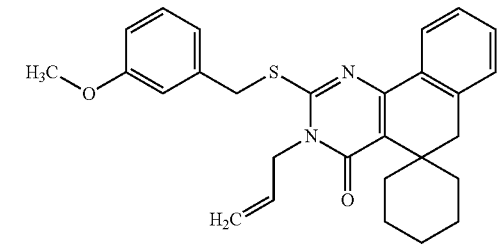 [SMILES: C=CCn1c(SCc2cccc(OC)c2)nc2c(c1=O)C1(CCCCC1)Cc1ccccc1-2] | 102485 |
| 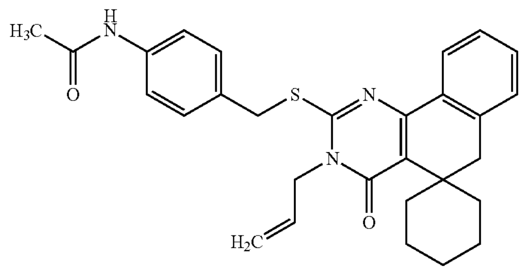 [SMILES: C=CCn1c(SCc2ccc(NC(C)=O)cc2)nc2c(c1=O)C1(CCCCC1)Cc1ccccc1-2] | 102491 |
| 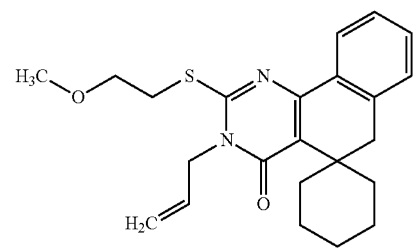 [SMILES: C=CCn1c(SCCOC)nc2c(c1=O)C1(CCCCC1)Cc1ccccc1-2] | 102493 |
| 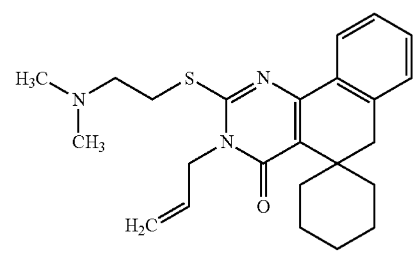 [SMILES: C=CCn1c(SCCN(C)C)nc2c(c1=O)C1(CCCCC1)Cc1ccccc1-2] | 102495 |
| 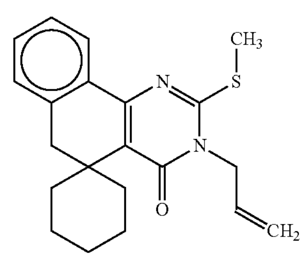 | 102620 |
| 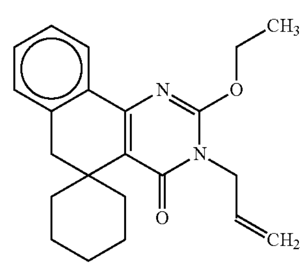 | 102622 |

TABLE 3-continued

>20% inhibition of *S. aureus* biofilm at 100 or 50 μM

| STRUCTURE | ID |
|---|---|
| | 203037 |
| 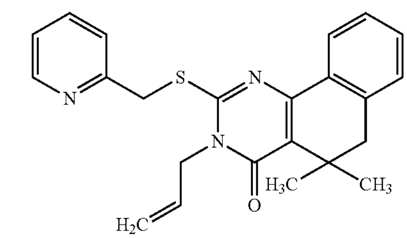 [SMILES: C=CCn1c(SCc2ccccn2)nc2c(c1=O)C(C)(C)Cc1ccccc1-2] | 203039 |
| 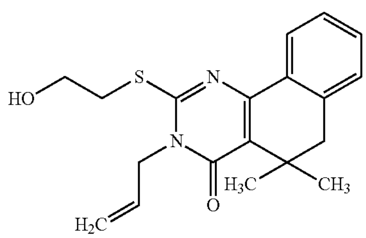 [SMILES: C=CCn1c(SCCO)nc2c(c1=O)C(C)(C)Cc1ccccc1-2] | 203041 |
| 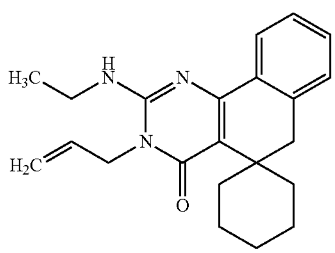 [SMILES: C=CCn1c(NCC)nc2c(c1=O)C1(CCCCC1)Cc1ccccc1-2] | 203043 |
| 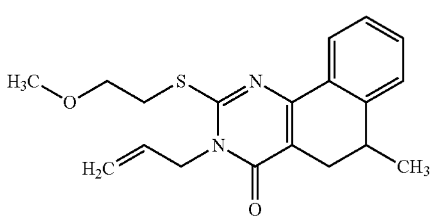 | 203574 |
| 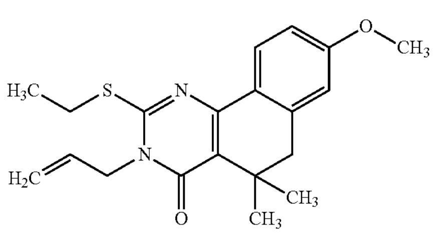 [SMILES: C=CCn1c(SCC)nc2c(c1=O)C(C)(C)Cc1cc(OC)ccc1-2] | 203592 |
| 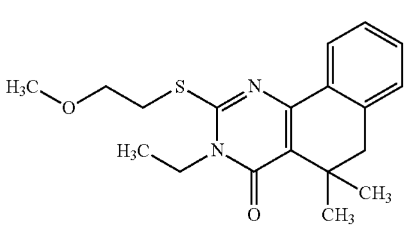 [SMILES: CCn1c(SCCOC)nc2c(c1=O)C(C)(C)Cc1ccccc1-2] | 203598 |

TABLE 3-continued

>20% inhibition of *S. aureus* biofilm at 100 or 50 μM

| STRUCTURE | ID |
|---|---|
| 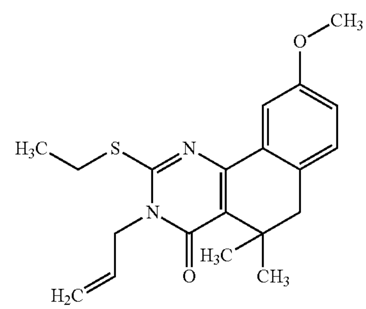 [SMILES: C=CCn1c(SCC)nc2c(c1=O)C(C)(C)Cc1ccc(OC)cc1-2] | 203625 |
| 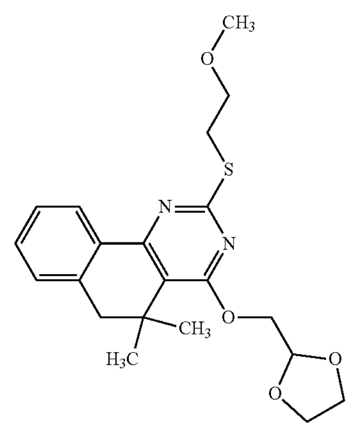 [SMILES: COCCSc1nc(OCC2OCCO2)c2c(n1)-c1ccccc1CC2(C)C] | 203627 |
| 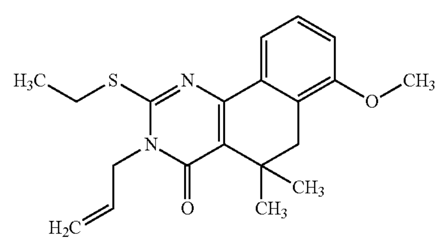 [SMILES: C=CCn1c(SCC)nc2c(c1=O)C(C)(C)Cc1c(OC)cccc1-2] | 203629 |
| 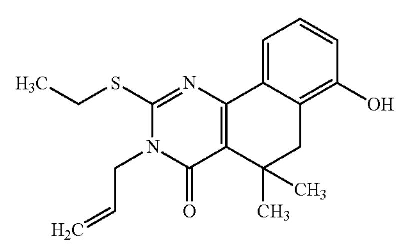 [SMILES: C=CCn1c(SCC)nc2c(c1=O)C(C)(C)Cc1c(O)cccc1-2] | 203631 |
| 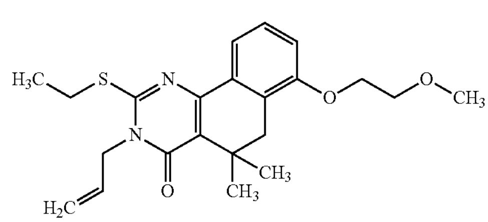 [SMILES: C=CCn1c(SCC)nc2c(c1=O)C(C)(C)Cc1c(OCCOC)cccc1-2] | 203633 |

TABLE 3-continued

>20% inhibition of *S. aureus* biofilm at 100 or 50 μM

| STRUCTURE | ID |
|---|---|
| (structure) | 203802 |
| (structure) | 203803 |
| (structure) | 203804 |
| (structure) | 204027 |
| (structure) | 204028 |
| (structure) | 204029 |
| (structure) | 204030 |
| (structure) | 204031 |

TABLE 3-continued
>20% inhibition of S. aureus biofilm at 100 or 50 μM
| STRUCTURE | ID |
|---|---|
| 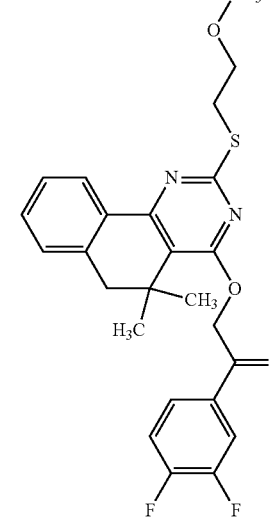 | 204033 |
| | 204036 |
| | 204037 |
| 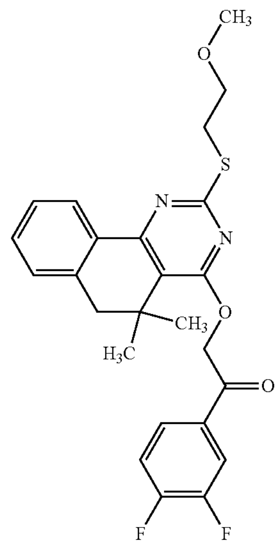 [SMILES: COCCSc1nc(OCC(=O)c2ccc(F)c(F)c2)c2c(n1)-c1ccccc1CC2(C)C] | 204040 |
| 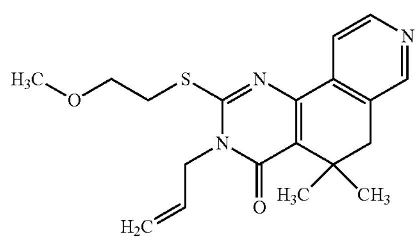 [SMILES: C=CCn1c(SCCOC)nc2c(c1=O)C(C)(C)Cc1cnccc1-2] | 204041 |
| 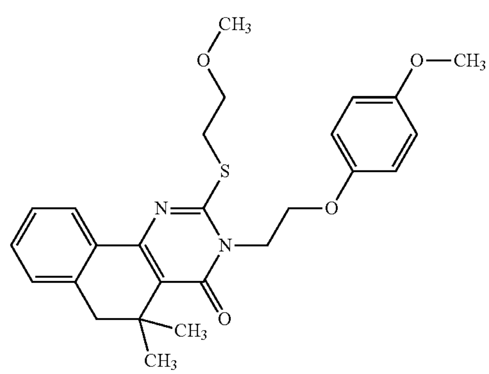 [SMILES: COCCSc1nc2c(c(=O)n1CCOc1ccc(OC)cc1)C(C)(C)Cc1ccccc1-2] | 204060 |
| 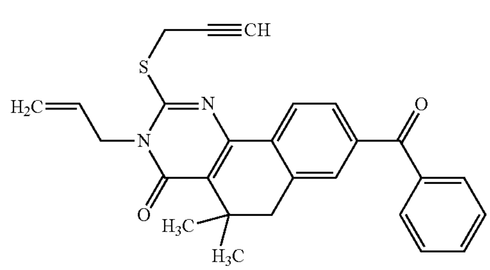 [SMILES: C#CCSc1nc2c(c(=O)n1CC=C)C(C)(C)Cc1cc(C(=O)c3ccccc3)ccc1-2] | 204080 |

TABLE 3-continued

>20% inhibition of *S. aureus* biofilm at 100 or 50 μM

| STRUCTURE | ID |
|---|---|
| 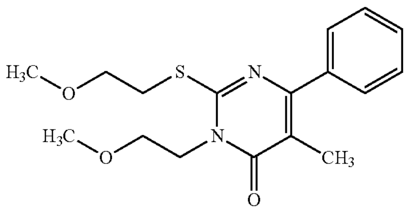 [SMILES: COCCSc1nc(-c2ccccc2)c(C)c(=O)n1CCOC] | 205360 |
| 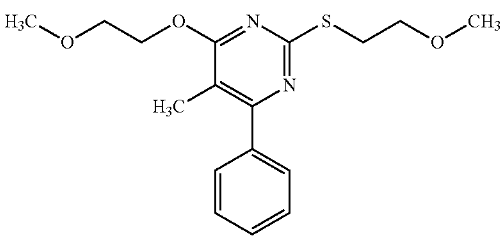 | 205361 |
| 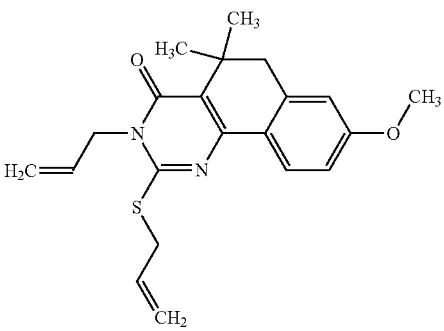 [SMILES: C=CCSc1nc2c(c(=O)n1CC=C)C(C)(C)Cc1cc(OC)ccc1-2] | 205363 |
| 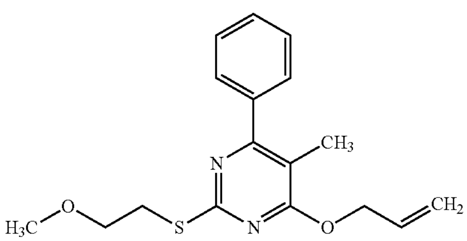 [SMILES: C=CCOc1nc(SCCOC)nc(-c2ccccc2)c1C] | 205382 |
| 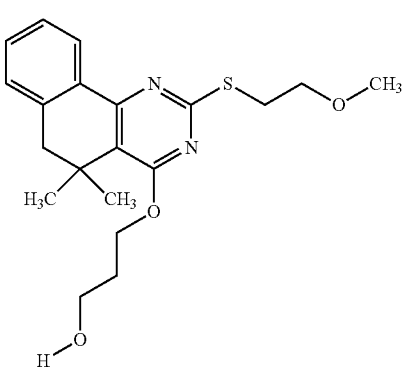 [SMILES: COCCSc1nc(OCCCO)c2c(n1)-c1ccccc1CC2(C)C] | 205384 |
| | 205387 |
| | 205390 |
| | 205396 |
| | 205426 |
| | 205427 |

TABLE 3-continued

>20% inhibition of *S. aureus* biofilm at 100 or 50 μM

| STRUCTURE | ID |
|---|---|
| (structure) | 205434 |
| (structure) | 205435 |
| (structure) | 205444 |
| (structure) | 205445 |
| (structure) | 205447 |
| (structure) | 205453 |
| (structure) | 205480 |
| (structure) | 206176 |

TABLE 3-continued

>20% inhibition of S. aureus biofilm at 100 or 50 µM

| STRUCTURE | ID |
|---|---|
| (structure) | 206178 |
| (structure) | 206227 |
| (structure) | 206230 |
| (structure) | 206231 |
| (structure) | 206233 |
| (structure) | 206234 |

TABLE 3-continued
>20% inhibition of S. aureus biofilm at 100 or 50 μM
| STRUCTURE | ID |
|---|---|
| 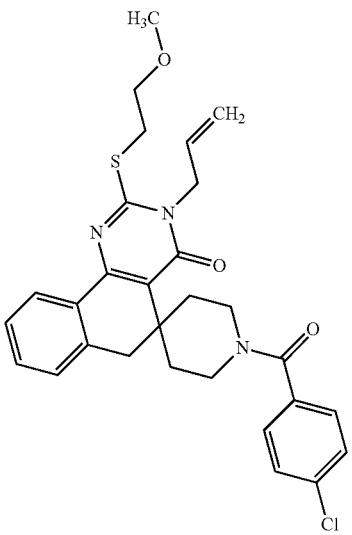 [SMILES: C=CCn1c(SCCOC)nc2c(c1=O)C1(CCN(C(=O)c3ccc(Cl)cc3)CC1)Cc1ccccc1-2] | 206235 |
| 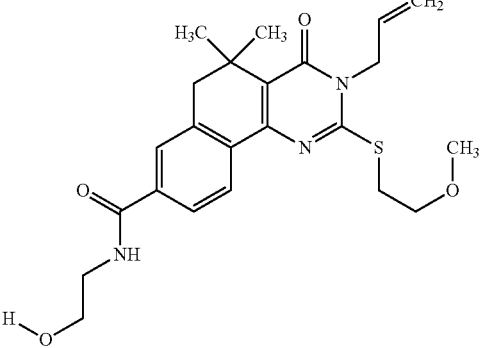 | 206239 |
| 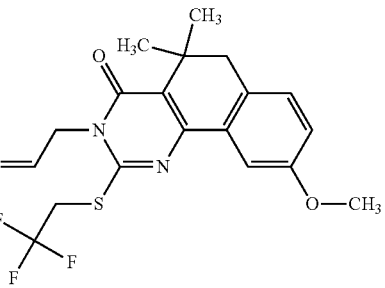 | 206352 |
| 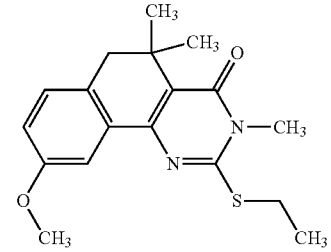 [SMILES: CCSc1nc2c(c(=O)n1C)C(C)(C)Cc1ccc(OC)cc1-2] | 206353 |
| 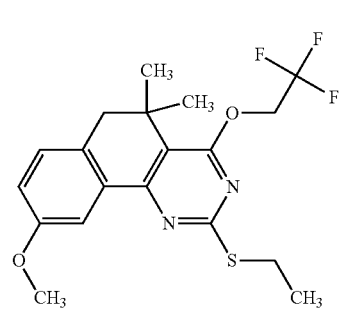 | 206355 |
| 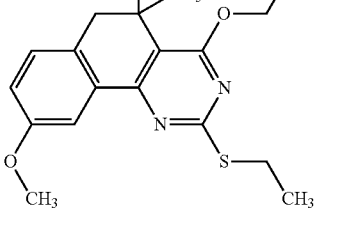 | 206356 |
| 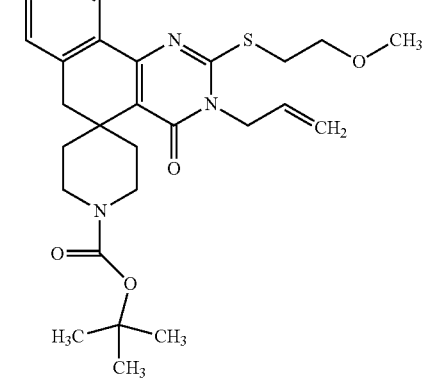 | 206358 |
| 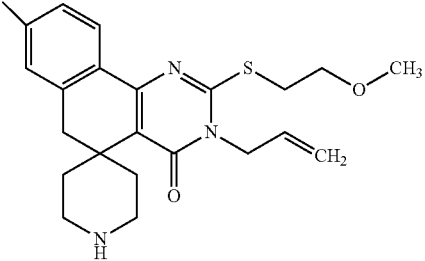 | 206660 |
| 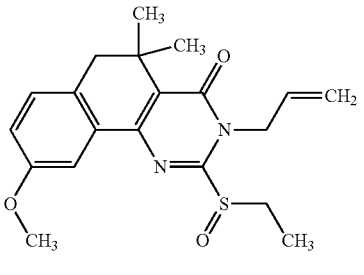 [SMILES: C=CCn1c(S(=O)CC)nc2c(c1=O)C(C)(C)Cc1ccc(OC)cc1-2] | 206661 |

TABLE 3-continued
>20% inhibition of S. aureus biofilm at 100 or 50 µM
| STRUCTURE | ID |
|---|---|
| 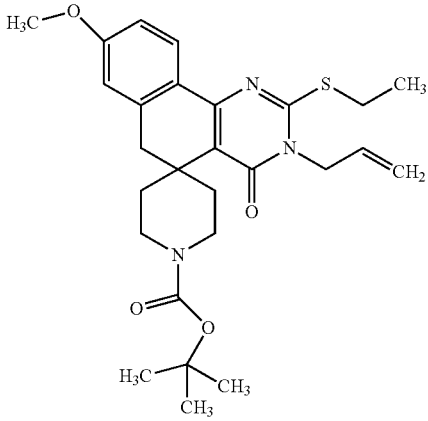 [SMILES: C=CCn1c(SCC)nc2c(c1=O)C1(CCN(C(=O)OC(C)(C)C)CC1)Cc1cc(OC)ccc1-2] | 206663 |
| 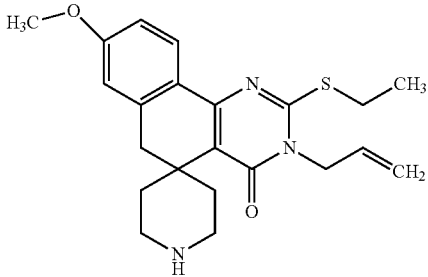 [SMILES: C=CCn1c(SCC)nc2c(c1=O)C1(CCNCC1)Cc1cc(OC)ccc1-2] | 206664 |
TABLE 4
| STRUCTURE | ID |
|---|---|
| 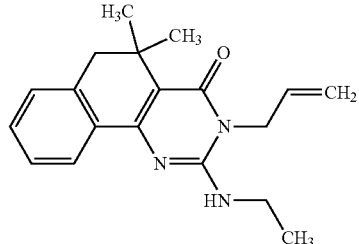 | 102483 |
| 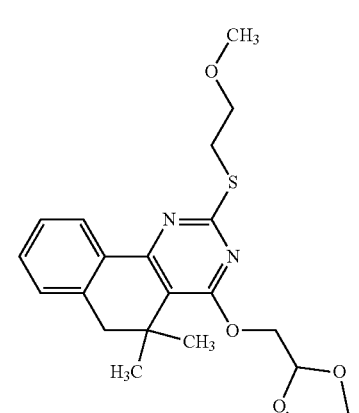 | 203043 |
| 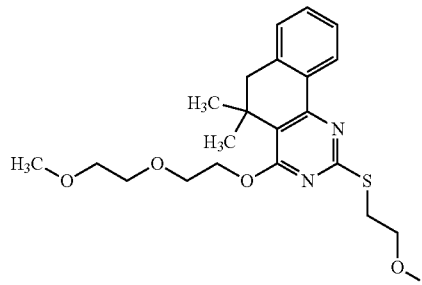 | 203804 |
| 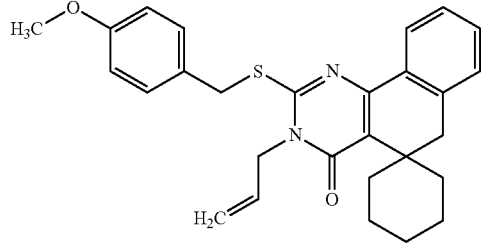 [SMILES: C=CCn1c(SCc2ccc(OC)cc2)nc2c(c1=O)C1(CCCCC1)Cc1ccccc1-2] | 204030 |
| 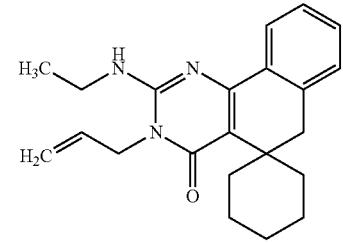 [SMILES: C=CCn1c(NCC)nc2c(c1=O)C1(CCCCC1)Cc1ccccc1-2] | 204033 |
| 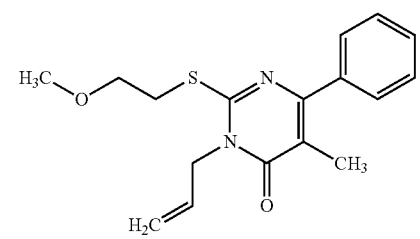 [SMILES: C=CCn1c(SCCOC)nc(-c2ccccc2)c(C)c1=O] | 205381 |
| 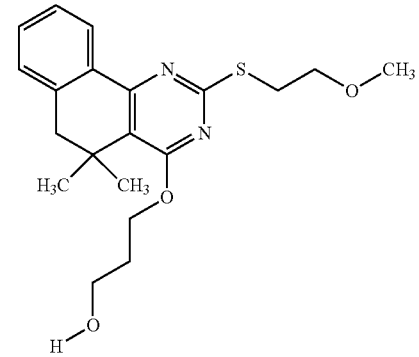 [SMILES: COCCSc1nc(OCCCO)c2c(n1)-c1ccccc1CC2(C)C] | 205384 |

TABLE 4-continued

| STRUCTURE | ID |
|---|---|
| (structure) | 205390 |
| (structure) | 205396 |
| (structure) | 205427 |
| (structure) | 205447 |
| (structure) | 206227 |

TABLE 4-continued

| STRUCTURE | ID |
|---|---|
| (structure) | 20639 |
| (structure) | 206353 |
| (structure) | 206660 |
| (structure) | 206661 |

TABLE 4-continued
| STRUCTURE | ID |
|---|---|
| 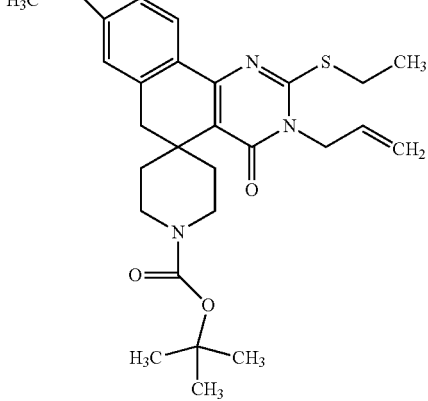 | 206663 |
| 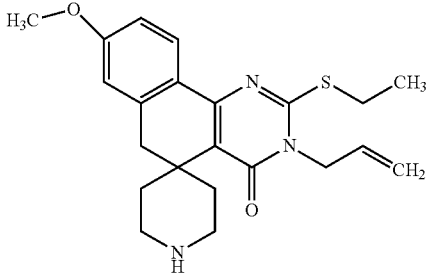 [SMILES: C=CCn1c(SCC)nc2c(c1=O)C1(CCNCC1)Cc1cc(OC)ccc1-2] | 206664 |
| 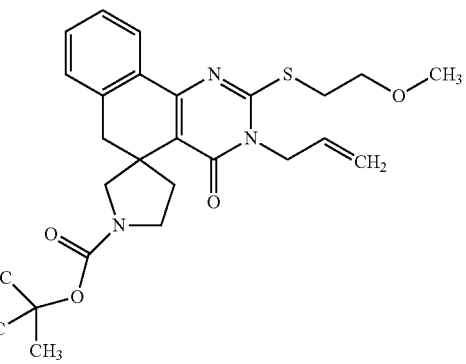 | 208860 |
| 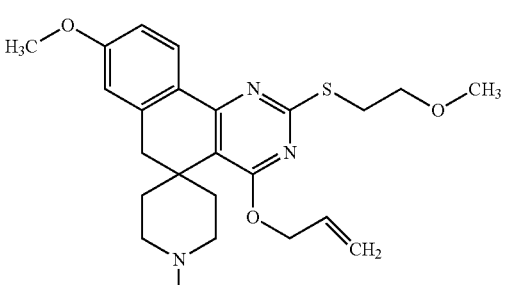 | 208863 |
| 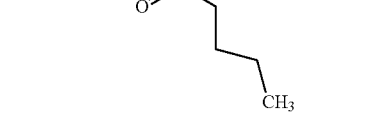 | 208864 |
| 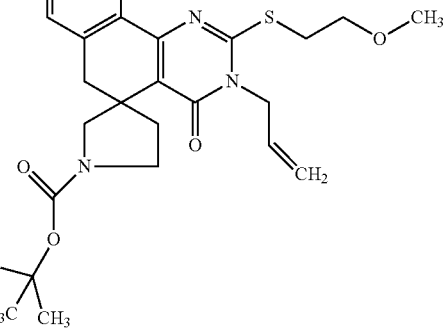 | 208865 |
| 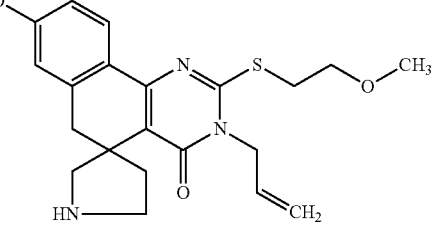 | 208981 |
| 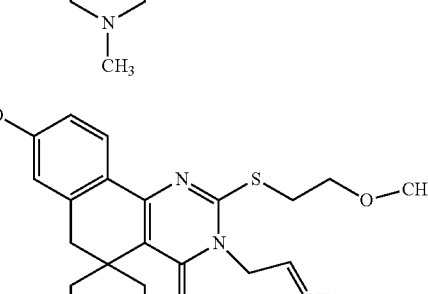 | 208982 |
| 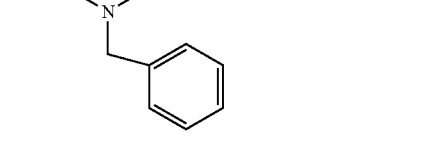 | 211790 |

TABLE 4-continued

| STRUCTURE | ID |
|---|---|
| (structure) | 211793 |
| (structure) | 211810 |
| (structure) | 211811 |
| (structure) | 211812 |
| (structure) | 211970 |

TABLE 4-continued

| STRUCTURE | ID |
|---|---|
| (structure) | 211971 |
| (structure) | 211972 |
| (structure) | 212010 |
| (structure) | 212011 |

TABLE 4-continued

| STRUCTURE | ID |
|---|---|
| 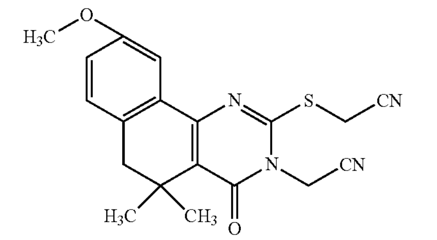 [SMILES: COc1ccc2c(c1)-c1nc(SCC#N)n(CC#N)c(=O)c1C(C)(C)C2] | 212012 |
| 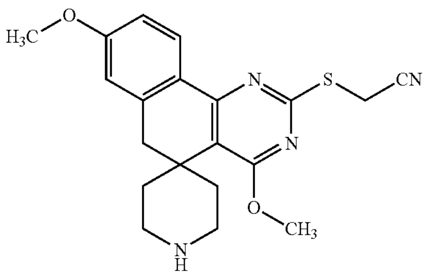 [SMILES: COc1ccc2c(c1)CC1(CCNCC1)c1c(OC)nc(SCC#N)nc1-2] | 212014 |
| 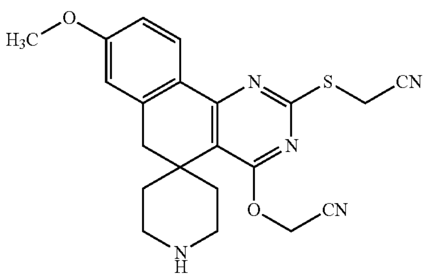 [SMILES: COc1ccc2c(c1)CC1(CCNCC1)c1c(OCC#N)nc(SCC#N)nc1-2] | 212015 |

Example 3

This example describes the synthesis of compounds of embodiments of the present disclosure. Synthesis of compounds with CCG designations 102483, 102485, 102491, 102493, 102495, 102620, 102622, 203037, 203039, 203041, 203043, and 203574 have been previously described in patent US20100331351; herein incorporated by reference in its entirety. The synthesis of compounds with CCG designations 203592, 203598, 203625, 203627, 203629, 203631, 203633, 203803, 203804, 204060, 205363, 205427, 205434, 205435, 205480, 206178, 206352, 206353, 206355, 206356, and 206358 are fully described and spectrally characterized by Yestrepsky et al. Bioorganic Medicinal Chemistry 2013, 21, 1887-1897; herein incorporated by reference in its entirety. The synthesis of the remaining compounds is described below.

Experimental and Spectroscopic Data of the Compounds
  Chemistry.

Chemical names follow CAS nomenclature. Starting materials were purchased from Fisher, Sigma-Aldrich Lancaster, Fluka or TCI-America and were used without purification. All reaction solvents were purchased from Fisher and used as received. Reactions were monitored by TLC using precoated silica gel 60 F254 plates. Silica gel chromatography was performed with silica gel (220-240 mesh) obtained from Silicycle.

Instrumentation.

NMR spectra were recorded on a Bruker 300 MHz, Bruker 400 MHz, Varian 400 MHz, or Varian 500 MHz spectrometer. Chemical shifts are reported in δ (parts per million), by reference to the hydrogenated residues of deuterated solvent as internal standard $CDCL_3$: δ=7.28 ($^1$H NMR) or as referenced to the hydrogenated residues of tetramethylsilane, δ=0.00 ($^1$H NMR). Mass spectra were recorded on a Micromass LCT time-of-flight instrument utilizing the electrospray ionization mode. Melting points were measured on a MEL-TEMP melting point apparatus and are uncorrected.

Scheme A.

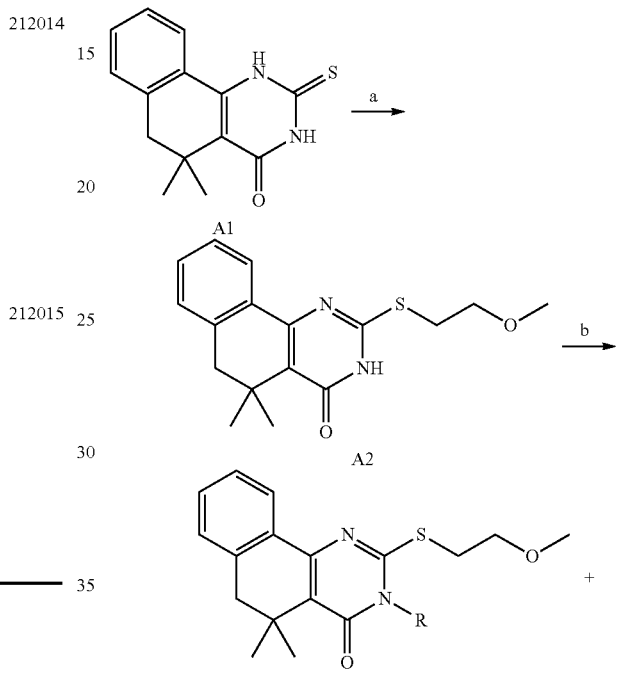

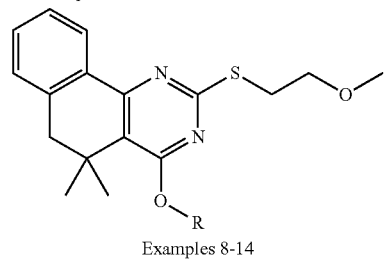

Preparation of Entry A1 (Scheme A)

5,5-Dimethyl-2-thioxo-2,3,5,6-tetrahydrobenzo[h]quinazolin-4(1H)-one was synthesized as described in Yestrepsky et al. *Bioorg Med Chem* 2013, 21, 1880-1897. $^1$H NMR (400 MHz, $CDCl_3$): δ (ppm) 9.95 (s, 1H, NH), 9.75 (s, 1H, NH), 7.57 (d, 1H, J=7.7 Hz), 7.46 (t, 1H, J=7.4 Hz), 7.39 (t, 1H, J=7.5 Hz), 7.28 (d, 1H, J=7.5 Hz), 2.78 (s, 2H), 1.33 (s, 6H).

Preparation of Entry A2 (Scheme A)

2-((2-Methoxyethyl)thio)-5,5-dimethyl-5,6-dihydrobenzo[h]quinazolin-4(3H)-one. A solution of compound A1 (2.7 g) and KOH (0.59 g) in absolute EtOH (60 mL) was refluxed for 30 minutes. A solution of 2-methoxyethyl p-toluenesulfonic ester (2.41 g) in EtOH (3 mL) was then added. The reaction was allowed to reflux for 16 h, then cooled. The crystallized solid was filtered, washed with EtOH (3 mL) and water (75 mL), dried under suction and then under high vacuum overnight, yielding the title compound as a white solid, 2.65 g (80% yield).

Scheme B.

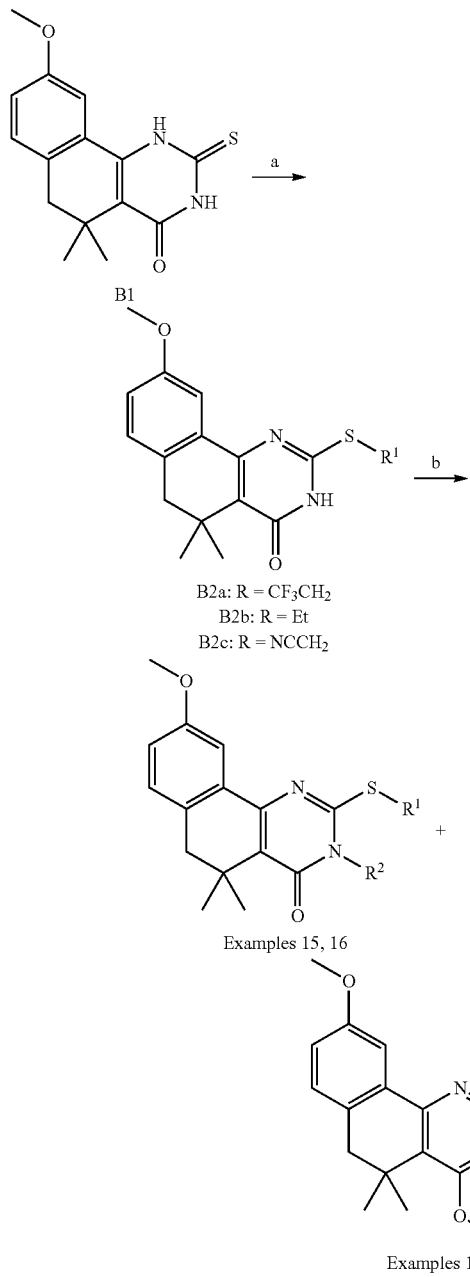

B2a: R = CF₃CH₂
B2b: R = Et
B2c: R = NCCH₂

Examples 15, 16

Examples 17-19

Preparation of Entry B1

9-Methoxy-5,5-dimethyl-2-thioxo-2,3,5,6-tetrahydrobenzo[h]quinazolin-4(1H)-one was synthesized as described in Yestrepsky et al. *Bioorg Med Chem* 2013, 21, 1880-1897. Isolated as a white powder, 650 mg, 61% yield over 2 steps. 1H NMR (400 MHz, CDCl₃) δ (ppm) 9.32 (s, 2H), 7.20 (d, J=8.2 Hz, 1H), 7.00 (dd, J=8.2, 2.4 Hz, 1H), 6.97 (d, J=2.4 Hz, 1H), 3.87 (s, 3H), 2.71 (s, 2H), 1.32 (s, 6H).

Preparation of Entry B2a

9-Methoxy-5,5-dimethyl-2-((2,2,2-trifluoroethyl)thio)-5, 6-dihydrobenzo[h]quinazolin-4(3H)-one. Compound B1 (50 mg, 0.173 mmol) was combined with 1,1,1-trifluoro-2-iodoethane (91 mg, 0.433 mmol) and sodium bicarbonate (22 mg, 0.260 mmol) in DMF (1 mL). The reaction was capped and heated to 40° C., and allowed to stir 16h. At this time the reaction was diluted with EtOAc and washed with water and brine. The organic extract was dried over MgSO₄, filtered, and concentrated in vacuo, then purified by flash chromatography (5% EH to 20% EH) to 49 mg of a yellow powder, 76% yield.

Preparation of Entry B2b 2-(Ethylthio)-9-methoxy-5,5-dimethyl-5,6-dihydrobenzo [h]quinazolin-4(3H)-one. The title compound was prepared in a manner similar to compound B2a using iodoethane as the alkylating agent. Isolated 181 mg as a white crystalline material, 82% yield.

Preparation of Entry B2c 2-((9-Methoxy-5,5-dimethyl-4-oxo-3,4,5,6-tetrahydrobenzo[h]quinazolin-2-yl)thio)acetonitrile. The title compound was prepared in a manner similar to compound B2a using a-chloroacetonitrile as the alkylating agent. Isolated 120 mg as a yellow powder, 71% yield.

Scheme C.

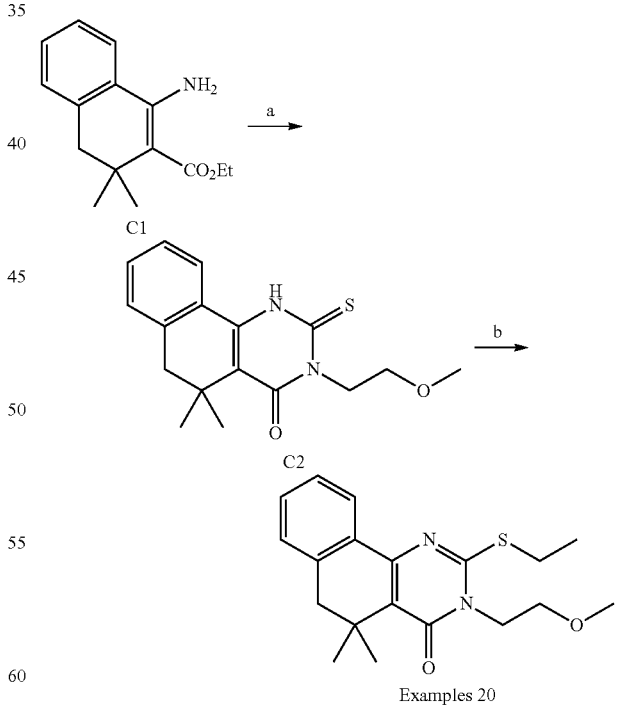

Examples 20

Preparation of Entry C1

Ethyl 1-amino-3,3-dimethyl-3,4-dihydronaphthalene-2-carboxylate was synthesized as described in Yestrepsky et al.

Bioorg Med Chem 2013, 21, 1880-1897. Isolated 860 mg as a yellow oil, 41% yield. TLC Rf=0.30 (10% EtOAc/hex). 1H NMR (500 MHz, CDCl$_3$) δ (ppm) 7.42 (d, J=8.6 Hz, 1H), 7.36-7.29 (m, 2H), 7.20 (d, J=7.3 Hz, 1H), 6.35 (s, 1H), 4.28 (q, J=7.1 Hz, 2H), 2.68 (s, 2H), 1.37 (t, J=7.1 Hz, 3H), 1.22 (s, 6H).

Preparation of Entry C2

3-(2-methoxyethyl)-5,5-dimethyl-2-thioxo-2,3,5,6-tetrahydrobenzo[h]quinazolin-4(1H)-one. Compound C1 (100 mg, 0.408 mmol) was combined with 2-methoxyethyl isothiocyanate (96 mg, 0.815 mmol) and acetic acid (49 mg, 0.815 mmol) in absolute ethanol (0.5 mL), then warmed to 70° C. and capped. Additional 2-methoxyethyl isothiocyanate (143 mg, 1.223 mmol) was added in 3 equal portions over 3 hours, then allowed to stir an additional 16 h at 70° C. At this time the reaction was partitioned between ethyl acetate and water. After extracting the aqueous layer with additional ethyl acetate, the combined organic extract was washed with water and brine, then dried over MgSO$_4$, filtered, and concentrated in vacuo. Further purification by flash chromatography yielded the title compound in 33% yield (43 mg).

Scheme D.

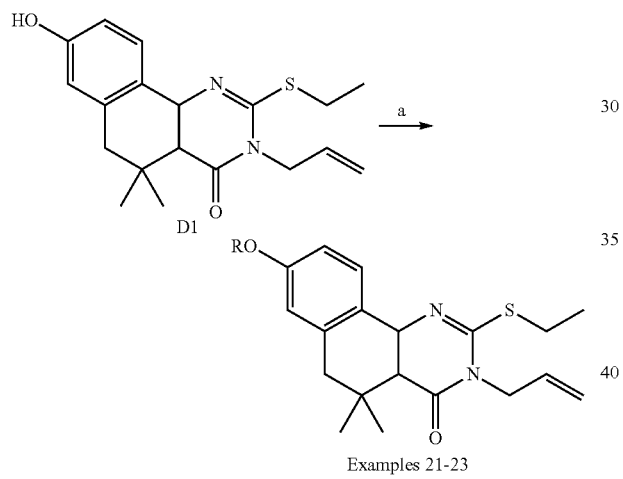

Examples 21-23

Preparation of Entry D1

3-allyl-2-(ethylthio)-8-hydroxy-5,5-dimethyl-4a,5,6,10b-tetrahydrobenzo[h]quinazolin-4(3H)-one was synthesized according to the procedure described in Yestrepsky et al. Bioorg Med Chem 2013, 21, 1880-1897. Isolated 310 mg as a tan solid, 43% yield. $^1$H NMR (500 MHz, CDCl$_3$) δ (ppm) 7.62 (d, J=8.2 Hz, 1H), 6.85-6.79 (m, 2H), 5.88 (ddt, J=16.3, 10.8, 5.9 Hz, 1H), 5.48-5.40 (m, 2H), 4.86 (d, J=5.9 Hz, 2H), 4.22 (q, J=7.3 Hz, 2H), 2.74 (s, 2H), 1.59 (t, J=7.3 Hz, 3H), 1.31 (s, 6H).

Scheme E.

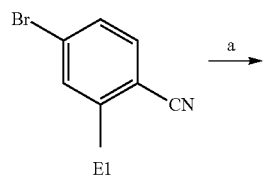

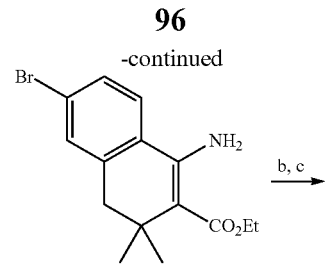

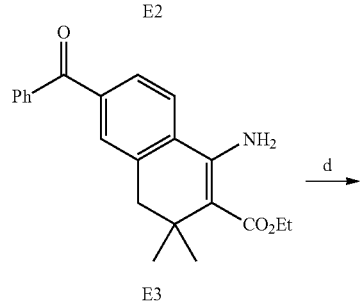

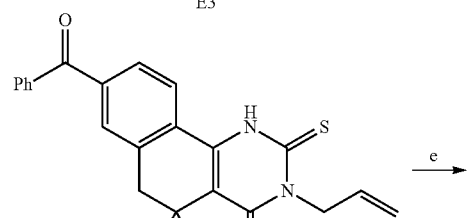

Example 24

Preparation of Entry E2

Ethyl 1-amino-6-bromo-3,3-dimethyl-3,4-dihydronaphthalene-2-carboxylate. Anhydrous diglyme (18 mL) was added to a dry round-bottomed flask and cooled to −78° C. Diisopropylamine (1.45 mL, 10.2 mmol) and n-butyllithium (2.5M in hexanes, 4.1 mL, 10.2 mmol) were added. The reaction was allowed to briefly warm up to 0° C. with stirring before recooling to −78° C. A solution of 4-bromo-2-methylbenzonitrile (1.0 g, 5.1 mmol) in diglyme (3 mL) was added slowly dropwise, causing the reaction to evolve a dark red color, and was allowed to stir for 20 minutes. Ethyl-3,3-dimethyl acrylate (1.06 mL, 7.65 mmol) was then added dropwise. Concurrently, to a separate dry round bottomed flask was added diglyme (6 mL) and zinc dust (834 mg, 12.75 mmol). The reaction was cooled to −78° C., then iodine (2.59 g, 10.2 mmol) was added slowly portionwise. The mixture was removed from the −78° C. bath and gently warmed with a heat gun until all traces of iodine were removed. The mixture was re-cooled to −78° C. and then added to the first reaction vessel. The reaction was allowed to warm to room temperature over the course of 2 hours, then was quenched by the addition of saturated aqueous NH₄Cl. The aqueous solution was extracted 5× with ether, then the combined organic extracts were washed 5× with water and 1× with brine. The organic layer was isolated, dried over MgSO₄, filtered, and concentrated in vacuo. Further purification via flash chromatography (2%-15% EtOAc:hex) furnished 890 mg of the desired product as a yellow solid, 54% yield.

Preparation of Entry E3

Ethyl 1-amino-6-benzoyl-3,3-dimethyl-3,4-dihydronaphthalene-2-carboxylate was prepared according to the methods of Carato et al., *Tetrahedron* 2006, 62, 9054-9058 and Moriello et al., *J Med Chem* 2006, 49, 2320-2332 as follows: Compound E2 (890 mg, 2.75 mmol) was dissolved in anhydrous toluene (27.5 mL). To this solution was added tetrakis(triphenylphosphine)palladium (317 mg, 0.275 mmol) and bis(tributyltin) (2.08 mL, 4.12 mmol). The reaction vessel was heated to reflux under nitrogen and allowed to stir 16h. The solvent was removed under reduced pressure and the aryl tributylstannyl intermediate was isolated via flash chromatography (0-5% EtOAc:hex) in 37% yield (547 mg.) This intermediate was dissolved in anhydrous DMF (4.3 mL), then iodobenzene (132 μL, 1.18 mmol) and bis(triphenylphospine)palladium(II) dichloride (38 mg, 0.054 mmol) were added. A stream of carbon monoxide gas was bubbled through the reaction mixture for 5 minutes, then the reaction tightly capped and affixed with a balloon of CO. The reaction was warmed to 90° C. and allowed to stir for 16 h. At this point the reaction was purged with N₂ for 10 minutes, then diluted with water. The aqueous mixture was extracted 3× with ether, then the combined organic extract was washed with water and brine. The organic layer was dried over MgSO₄, filtered, concentrated in vacuo. Separation via flash chromatography (0-5% EtOAc:hex) delivered 187 mg of the title compound in 50% yield (19% over two steps).

Preparation of Entry E4

3-Allyl-8-benzoyl-5,5-dimethyl-2-thioxo-2,3,5,6-tetrahydrobenzo[h]quinazolin-4(1H)-one. Compound E3 (187 mg, 0.535 mmol) was dissolved in absolute ethanol (0.72 mL), followed by acetic acid (61 μL, 1.07 mmol) and allyl isothiocyanate (104 μL, 1.14 mmol). The reaction was warmed to 70° C. and allowed to stir for 1 hour. Additional allyl isothiocyanate (156 μL, 1.71 mmol) was added in 3 equal portions over the course of 3 hours, then the reaction was allowed to stir 12 additional hours at 70° C. At this time the reaction was quenched by the addition of water. The aqueous layer was extracted 3× with ethyl acetate, then the combined organic extract was washed with water and brine. The organic extract was dried over MgSO₄, filtered, and concentrated in vacuo. Further purification via flash chromatography yielded the title compound as a yellow oil (110 mg, 37% yield).

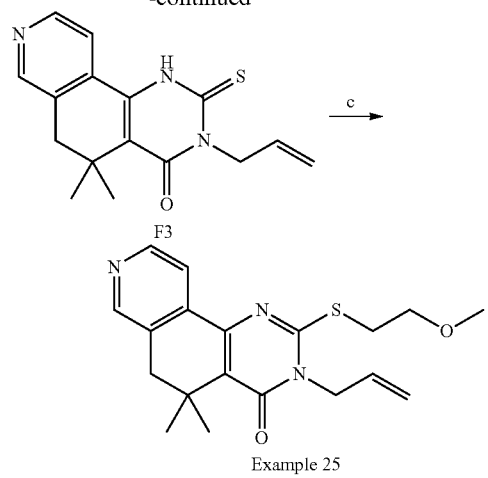

Preparation of Entry F2

Ethyl 5-amino-7,7-dimethyl-7,8-dihydroisoquinoline-6-carboxylate was prepared in a manner similar to that of entry E2 from 3-methylisonicotinonitrile F1. Isolated 500 mg of a pale yellow solid, 48% yield.

Preparation of Entry F3: 3-allyl-5,5-dimethyl-2-thioxo-2,3,5,6-tetrahydropyrido[3,4-h]quinazolin-4(1H)-one To a 0° C. suspension of sodium hydride 60% (0.27 g, 7.15 mmol) in dry DMF (10 mL) was added dropwise a mixture of 3-isothiocyanatoprop-1-ene (0.32 g, 3.25 mmol) and F2 (0.8 g, 3.25 mmol) in dry DMF (10 mL). After the addition was complete the mixture was stirred 3 hours before pouring into ice water. Acidified with NH₄Cl. Extracted with Et₂O 2× and EtOAc (1×). The organic extracts were washed with satd. NaCl and dried over MgSO₄. Flash chromatography provided 3-allyl-5,5-dimethyl-2-thioxo-2,3,5,6-tetrahydropyrido[3,4-h]quinazolin-4(1H)-one (0.19 g, 0.64 mmol, 19.5% yield) as a solid. NMR (400 MHz, CDCl₃) δ 8.6 (d, J=4 Hz, 1H), 8.5 (s, 1H), 7.4 (d, J=4 Hz, 1H), 6.2-6.3 (m, 1H), 6.1-6.2 (m, 2H), 5.3-5.4 (m, 2H), 2.8 (s, 2H), 1.4 (s, 6H). ESI+MS m/z 300.0 (M+H⁺).

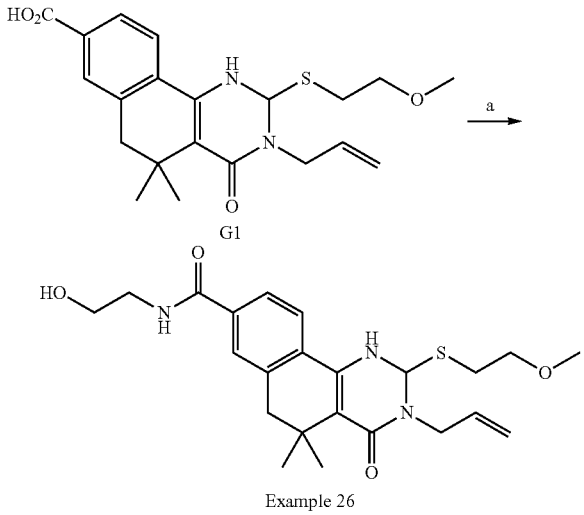

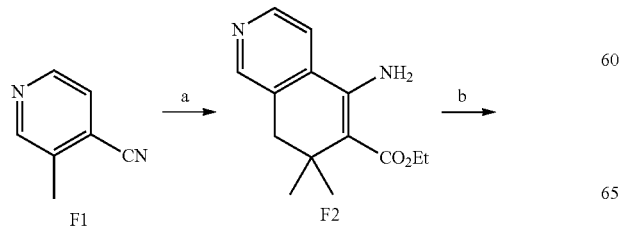

Preparation of Entry G1

3-allyl-2-((2-methoxyethyl)thio)-5,5-dimethyl-4-oxo-3,4,5,6-tetrahydrobenzo[h]quinazoline-8-carboxylic acid. Compound G1 was prepared as previously reported by Yestrepsky et al. *Bioorg Med Chem* 2013, 21, 1880-1897. $^1$H NMR (400 MHz, CDCl3) δ (ppm) 8.18-8.19 (m, 1H), 8.01-8.05 (m, 1H), 7.95 (br s, 1H), 6.20-6.23 (m, 1H), 5.89-5.94 (m, 1H), 5.26-5.31 (m, 2H), 4.58-4.63 (m, 2H), 3.72-3.78 (m, 4H), 3.49-3.52 (m, 2H), 3.42 (s, 3H), 2.94-2.95 (m, 2H), 2.80 (s, 2H), 1.37 (s, 6H). ESI+MS m/z=400.49 (M+H+).

Scheme H.

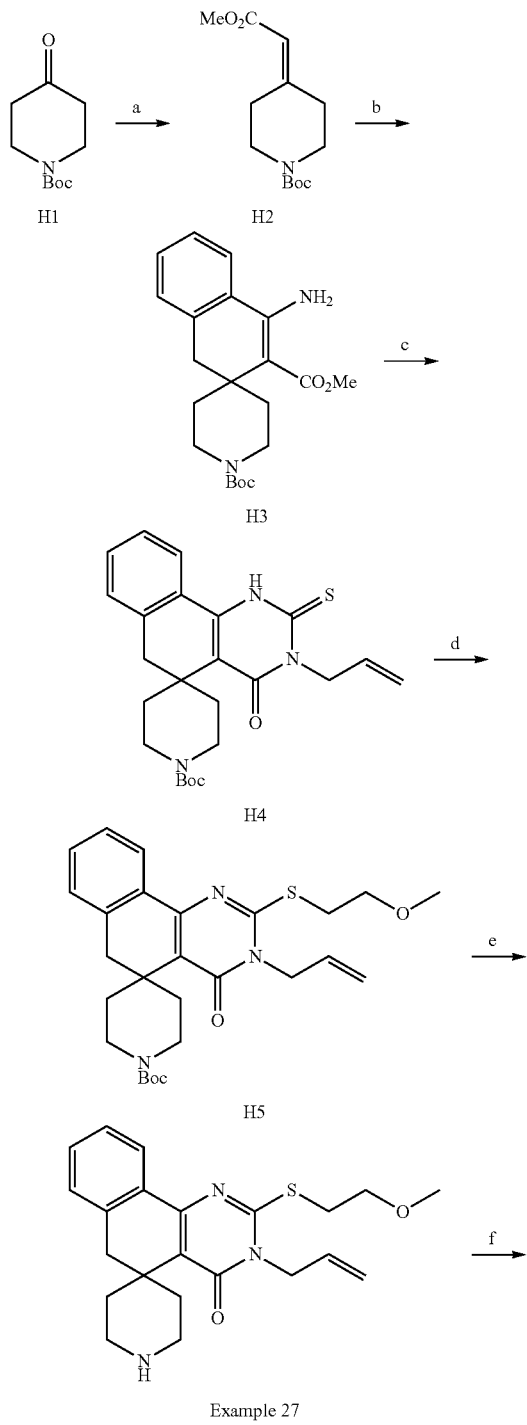

Example 27

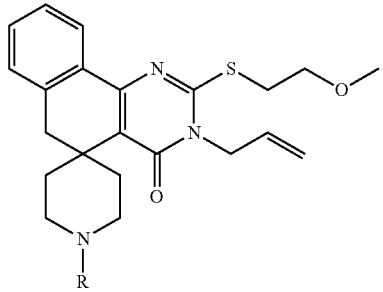

Example 28-32

Preparation of Entry H2 t-Butyl 4-(2-methoxy-2-oxoethylidene)piperidine-1-carboxylate. 60% NaH (3.06 g) was washed with dry hexane (2×20 mL) and the clear solution was syringed out under N$_2$ atmosphere. The washed NaH was suspended in dry DMF (100 mL) and cooled to 0° C. To this suspension was added slowly trimethyl phosphonoacetate (14.1 mL) over a period of 20 minutes. Compound H1 (14.0 g, 78 mmol) in dry DMF (15 mL) was slowly added to the solution. The temperature was maintained at 0° C. over a period of 20 minutes, then allowed to stir while warming to RT for 3 h. At this point the reaction was diluted with Et$_2$O (250 mL) and washed with water (100 mL). The aqueous layer was back extracted with additional diethyl ether (40 mL), then the combined organic extract was washed with water (4×50 mL) and brine (30 mL). The separated organic layer was dried over MgSO$_4$, filtered and the solvent was removed under reduced pressure to yield the product as a crystalline solid. Isolated 16.95 g (94% yield).

Preparation of Entry H3

1'-tert-butyl 3-methyl 4-amino-1H-spiro[naphthalene-2,4'-piperidine]-1',3-dicarboxylate was prepared in a manner similar to that of entry F2. Isolated 5.71 g as a pale yellow solid after flash chromatography, 34% yield.

Preparation of Entry H4 t-Butyl 3-allyl-4-oxo-2-thioxo-2,3,4,6-tetrahydro-1H-spiro[benzo[h]quinazoline-5,4'-piperidine]-1'-carboxylate. To a solution of compound H3 (0.813 g) in EtOH (7 mL) was added allyl isothiocyanate (0.43 mL) and the reaction was heated at 85° C. for 1 h. An additional 0.2 mL of allyl isothiocyanate was added and the reaction was heated at 85° C. for an additional 15 h. The solution was cooled to RT and the precipitated product was filtered, washed with EtOH and dried under air and then in oven for 2 h. Treatment of the filtrate with 200 μL of allyl isothiocyanate and heating for 16 h at 85° C. resulted in the precipitation of additional product, which was collected and purified in an identical manner. Isolated a total of 0.575 g of H4 as an off-white solid (60% yield).

Preparation of Entry H5 t-Butyl 3-allyl-2-((2-methoxyethyl)thio)-4-oxo-4,6-dihydro-3H-spiro[benzo[h]quinazoline-5,4'-piperidine]-1'-carboxylate. To a solution of compound H4 (0.25 g) in DMF (2.5 mL) was added Cs$_2$CO$_3$ (371 mg). The reaction mixture was stirred for 3 minutes, then 2-methoxyethyl p-toluenesulfonate (0.131 g) was added and the reaction was stirred at 70° C. for 2h. The solvent was removed under reduced pressure and the residue was extracted with EtOAc (5 mL) and H$_2$O (4 mL). The separated organic layer was washed with H$_2$O (4×2 mL), dried over Na$_2$SO$_4$ and the solvent was removed under reduced pressure to yield 280 mg of the title compound (100% yield).

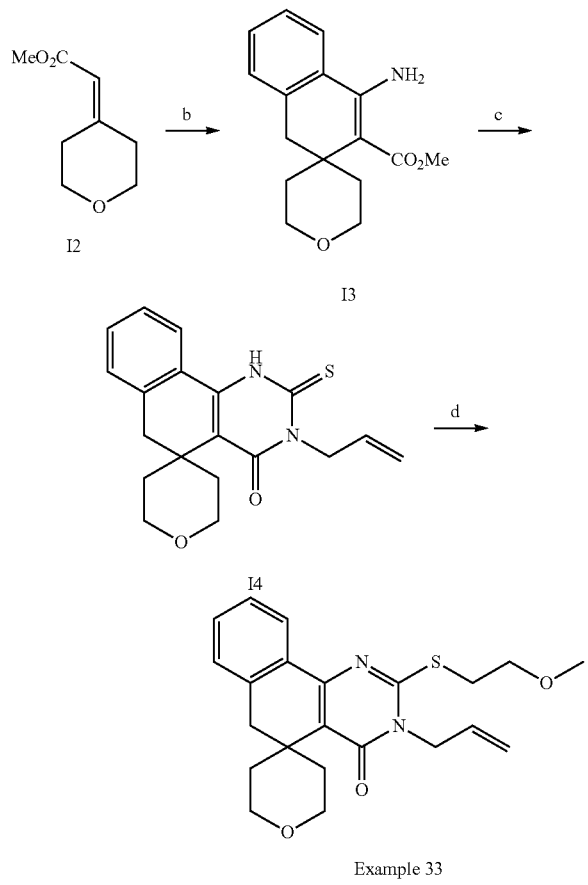

Ethyl 4-amino-2',3',5',6'-tetrahydro-1H-spiro[naphthalene-2,4'-pyran]-3-carboxylate, I3

To a solution of diisopropylamine at −78° C. in anhydrous diglyme (15 mL) was added 2.5 M n-BuLi slowly over a period of 10 minutes. The reaction was stirred at that temperature for 40 minutes more. Then 2-methylbenzonitrile (0.69 g, 5.88 mmole) was added slowly over 15 minutes at −78° C. The reaction was stirred at the same temperature for 15 minutes. Then the ethyl ester I2 (1 g, 5.88 mmole in 4 mL Diglyme) was added slowly over a period of 10 minutes and the reaction was stirred for 30 minutes at −78° C. ZnI$_2$ (1.875 g) was added and the reaction was slowly allowed to warm up to room temperature and stirred for 2 h. The reaction was quenched with a saturated solution of ammonium chloride. Ether (50 mL) was added and extracted in a separatory funnel. The separated aqueous layer was again extracted with ether (2×20 mL). The combined organic layers were washed with water (3×30 mL), dried (MgSO$_4$) and the solvent was removed under reduced pressure. The trace solvent was removed at 70° C. in rotavap for 3 h. The isolated crude product was purified by flash chromatography using prepacked Biotage (80 g) column using Isco-Teldyne flash system. The column was eluted with 10% EtOAc/hexanes. The fractions were combined after checking TLC using 50% EtOAc/hexane as eluent. The compound was further purified by crystallization from EtOAc/hexanes to yield Ethyl 4-amino-2',3',5',6'-tetrahydro-1H-spiro[naphthalene-2,4'-pyran]-3-carboxylate, 13, 0.19 g (11.3%); R$_f$=0.51 (1:1, EtOAc/hexanes).

3-Allyl-2-thioxo-2,2',3,3',5',6'-hexahydro-1H-spiro[benzo[h]quinazoline-5,4'-pyran]-4(6H)-one, I4

To a solution of I3 (174 mg, 1 mmole) in absolute EtOH (7 mL) was added allyl isothiocyanate (180 mg, 3 mmole). The reaction mixture was refluxed, under N$_2$ atm, for 4 h. An additional 0.15 g of allyl isothiocyanate was added and the reaction was continued for further 2 h at reflux. The solvent was removed under reduced pressure via rotary evaporator and the residue was chromatographed using 12 g prepacked Silicycle column. The column was eluted with 25% EtOAc/hexanes to obtain the title compound, 45 mg (22%).

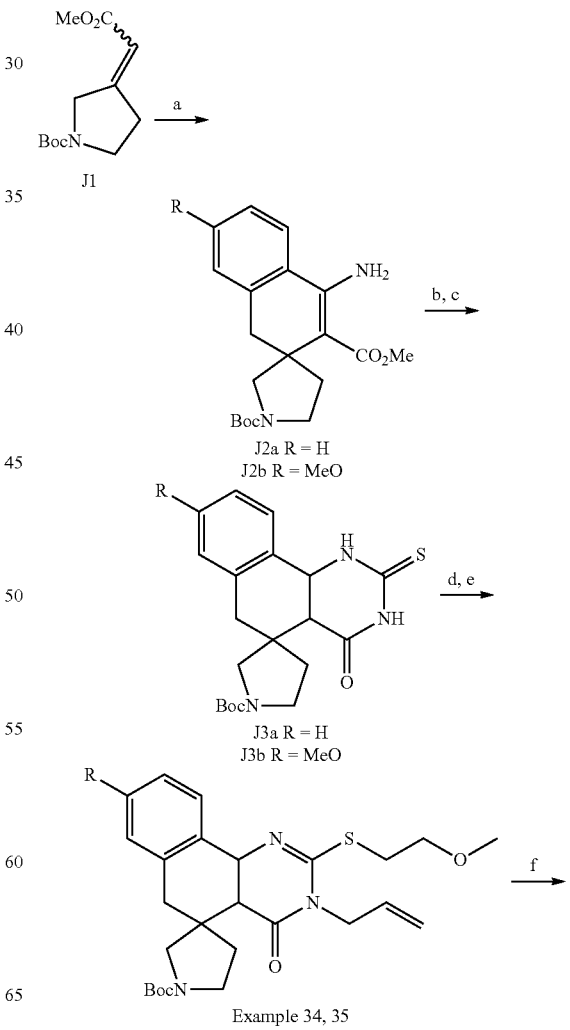

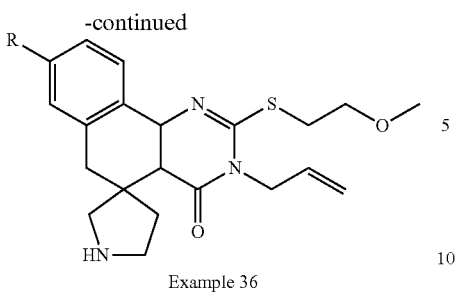

Example 36

Preparation of Entry J2a

1'-tert-butyl 3-methyl 4-amino-1H-spiro[naphthalene-2,3'-pyrrolidine]-1',3-dicarboxylate was prepared in a manner similar to that used to synthesize entry E2. Isolated 195 mg as a sticky yellow solid, 30% yield.

Preparation of Entry J2b

1'-tert-butyl 3-methyl 4-amino-7-methoxy-1H-spiro[naphthalene-2,3'-pyrrolidine]-1',3-dicarboxylate was prepared in a manner similar to that used to synthesize entry E2. Isolated as a sticky yellow solid (220 mg, 25% yield).

Preparation of Entry J3a tert-butyl 4-oxo-2-thioxo-2,3,4,4a,6,10b-hexahydro-1H-spiro[benzo[h]quinazoline-5,3'-pyrrolidine]-1'-carboxylate. Compound J2a (190 mg, 0.530 mmol) was dissolved in absolute ethanol (630 µL), to which benzoyl isothiocyanate (112 mg, 0.689 mmol) was added. The solution was warmed to 75° C. and allowed to stir for 3 hours. At this time additional benzoyl isothiocyanate (43 mg, 0.265 mmol) was added and the solution allowed to stir at 75° C. overnight. The reaction was concentrated in vacuo and redissolved in a solution of ethanol and water (2:1, 1.3 mL). Potassium hydroxide (49 mg, 0.870 mmol) was added, and the reaction was warmed to 75° C. and allowed to stir for 90 minutes. The reaction was halted by the addition of saturated aqueous ammonium chloride solution (5 mL). The aqueous layer was extracted 3× with dichloromethane, then the combined organic extracts were washed with saturated ammonium bicarbonate solution, water, and brine. The organic extract was dried over MgSO$_4$, filtered, and concentrated under reduced pressure. Further purification via flash chromatography (10-30% EtOAc:hex) delivered 114 mg of the title compound (68% yield) as white crystals.

Preparation of Entry J3b tert-butyl 8-methoxy-4-oxo-2-thioxo-2,3,4,4a,6,10b-hexahydro-1H-spiro[benzo[h]quinazoline-5,3'-pyrrolidine]-1'-carboxylate was prepared from J2b in a manner similar to that of entry J3a. Isolated 275 mg of the title compound (49% yield) as white crystals.

Scheme K.

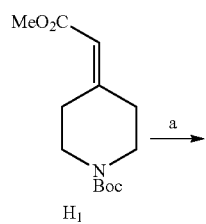

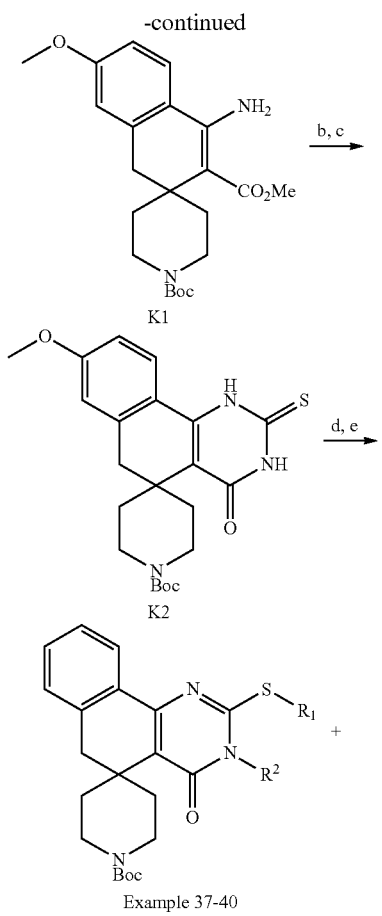

Example 37-40

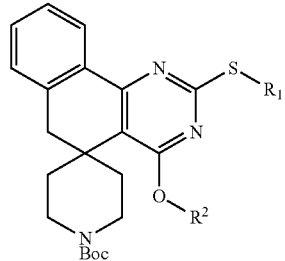

Example 41, K3

Preparation of Entry K1

1'-tert-butyl 3-methyl 4-amino-7-methoxy-1H-spiro[naphthalene-2,4'-piperidine]-1',3-dicarboxylate was prepared from compound H1 and 4-methoxybenzonitrile in a manner similar to the procedure used for entry E2. After purification by column chromatography and trituration with 1:1 diethyl ether:hexanes, the title compound was delivered as a white crystalline solid (1.95 g, 68% yield).

Preparation of Entry K2 tert-butyl 8-methoxy-4-oxo-2-thioxo-2,3,4,6-tetrahydro-1H-spiro[benzo[h]quinazoline-5,4'-piperidine]-1'-carboxylate was prepared from K1 in a manner similar to that employed for the synthesis of J3a. Isolated 950 mg as a white solid, 48% yield.

Preparation of Entry K3 tert-butyl 4-(allyloxy)-2-((2-methoxyethyl)thio)-6H-spiro[benzo[h]quinazoline-5,4'-piperidine]-1'-carboxylate. Intermediate K2 (940 mg, 2.19 mmol) was dissolved in dimethylformamide (13 mL), to which 2-methoxyethyl p-toluenesulfonate (554 mg, 2.407 mmol) and sodium bicarbonate (276 mg, 3.28 mmol) were added. The reaction was warmed to 50° C. and allowed to stir overnight. At this point the reaction was halted by the addition of water, followed by extraction 3× into ethyl acetate. The combined organic layer was washed with water and brine, then concentrated in vacuo to a yellow solid. The solid was triturated with hexanes and collected via filtration, and then washed with 15 mL of 1:1 hexane:diethyl ether solution. The solid was collected and dried under high vacuum to obtain 790 mg (1.62 mmol 74% yield) of the S-alkylated intermediate. This solid was redissolved in methanol (9.5 mL), to which sodium methoxide (175 mg, 3.24 mmol) and allyl bromide (294 mg, 2.43 mmol) were added. The reaction vessel was heated to 50° C. and allowed to stir for 3 hours. The reaction was halted via the addition of water, followed by extraction into ethyl acetate. The organic layer was washed with water and brine, then dried over MgSO₄, filtered, and concentrated to a colorless oil consisting of N- and O-alkylated isomers. Purification via flash chromatography isolated O-allyl isomer K3 as a white crystalline solid (94 mg, 8.2% yield over 2 steps).

Scheme L.

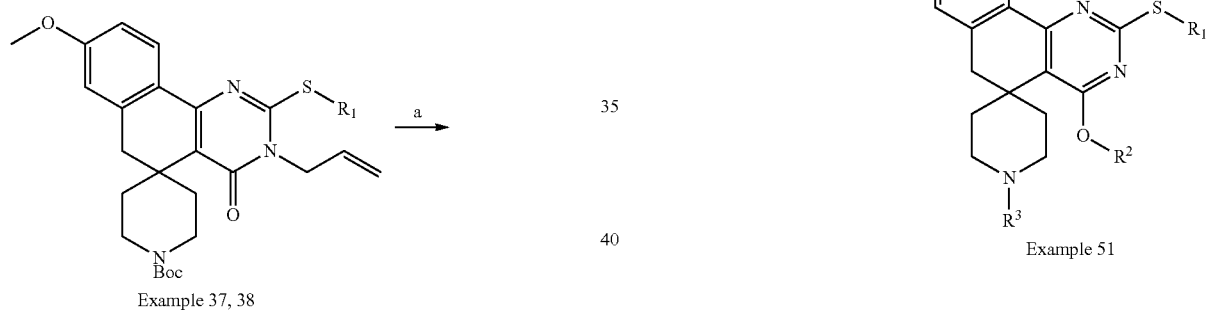

Example 37, 38

Example 42, 43

Example 44-48

Scheme M.

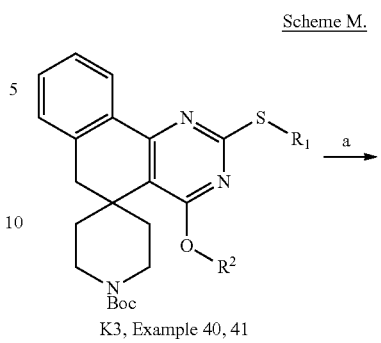

K3, Example 40, 41

Example 49, 50

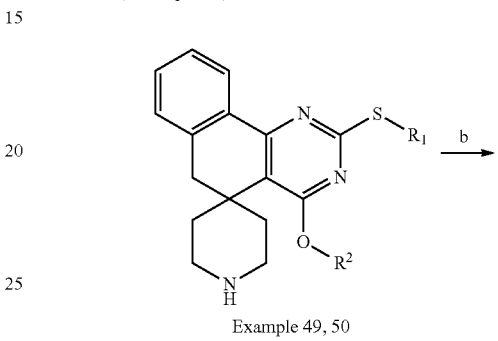

Example 51

Scheme N.

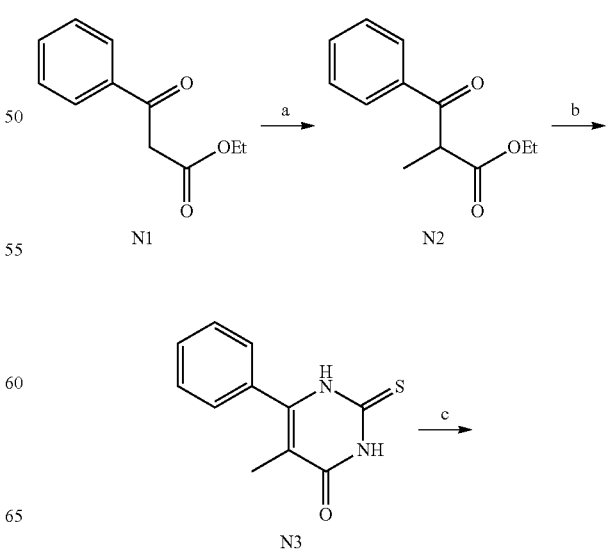

N1

N2

N3

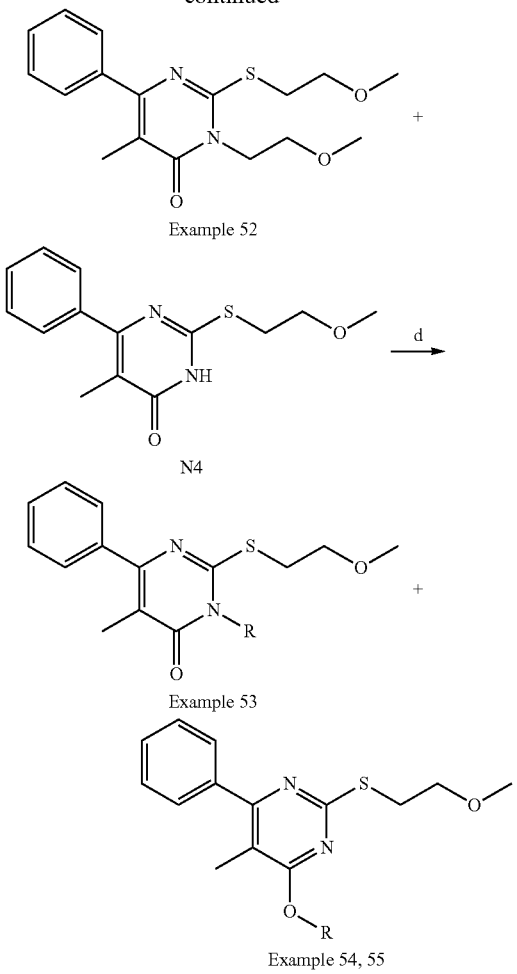

Example 52

N4

Example 53

Example 54, 55

Preparation of Entry N2

Ethyl 2-methyl-3-oxo-3-phenylpropanoate was prepared according to the procedure of Wymann, *Syn Comm* 18(1988) 1379 from ethyl 3-oxo-3-phenylpropanoate (N1).

Preparation of Entry N3

5-Methyl-6-phenyl-2-thioxo-2,3-dihydropyrimidin-4 (1H)-one was prepared from ethyl 2-methyl-3-oxo-3-phenylpropanoate (N2) according to the procedure described in U.S. Pat. No. 2,740,785 as follows: Compound N2 (10.1 g, 49.0 mmol) was added dropwise to a stirred solution of sodium (2.25 g, 98.0 mmol) in ethanol (50 mL) under $N_2$, then thiourea (5.2 g, 68.1 mmol) was added in one portion. The mixture was heated to reflux for 7 hours then allowed to cool. Most of the solvent was removed by rotary evaporator, and the residue was stirred into 450 mL of water. Concentrated HCl was added until the pH was 3-4. After about an hour the precipitate was filtered off, rinsed with water and dried to afford the product (7.5 g) as a white solid; mp 216-227° C.; mass spec ES+ m/z=219, 241 (m+1, m+23).

Preparation of Entry N4

2-((2-methoxyethyl)thio)-5-methyl-6-phenylpyrimidin-4 (3H)-one. Triisopropylamine (0.36 g, 2.8 mmol) was added to a stirred solution of 5-methyl-6-phenyl-2-thioxo-2,3-dihydropyrimidin-4(1H)-one (0.5 g, 2.3 mmol) from Example 5-016B Step 2 in tetrahydrofuran (5 mL) under $N_2$ at room temperature, and followed after 5 minutes by 2-bromoethyl methyl ether (0.35 g, 2.4 mmol) in one portion. After stirring for a short while the mixture was heated to reflux for 18 hours, cooled, and stripped of solvent by rotary evaporator. The residue was stirred in water for an hour, then the solid was filtered off, rinsed with water and dried. The resulting white powder was dissolved in 1.5 mL of hot dimethylformamide, filtered, diluted with an equal volume of ethanol and allowed to cool to afford the pure product (0.4 g). mp 132-134° C. Mass spec ES+ m/z=277, 299 (m+1, m+23); ES− m/z=275 (m−1); $^1$H NMR (500 MHz, dmso) δ 12.72 (bs, 1H), 7.67-7.56 (m, 2H), 7.50-7.43 (m, 3H), 3.58 (t, 2H), 3.30 (m, 2H), 3.25 (s, 3H), 1.96 (s, 3H).

General Procedure for Example Compounds 1-14

To a solution of alkylating agent (0.23 mmol) in DMF (1 mL) were added $K_2CO_3$ (0.57 mmole) and the compound A2 (0.19 mmol). The solution was stirred at RT for 20 h. The solvent was removed under reduced pressure and the residue was extracted with EtOAc (3 mL) and water (1 mL). The separated organic layer was washed with water (1 mL), dried ($MgSO_4$) and the solvent was removed under reduced pressure to yield the crude compound, generally a mixture of N- and O-alkylated isomers. The crude mixture was separated and purified by flash chromatography using EtOAc/hexanes.

Example Compound 1

3-(2-(4-Fluorophenoxy)ethyl)-2-((2-methoxyethyl)thio)-5,5-dimethyl-5,6-dihydrobenzo-[h]quinazolin-4(3H)-one (CCG-204027): 59 mg (69%); $^1$H NMR (CDCl$_3$/TMS) δ 8.03 (d, 1H, J=7.5 Hz), 7.28-7.36 (m, 2H), 7.16 (d, 1H, J=6.6 Hz), 6.90-6.96 (m, 2H), 6.82-6.89 (m, 2H), 4.44 (t, 2H, J=6.2 Hz), 4.25 (t, 2H, J=6.2 Hz), 3.75 (t, 2H, J=6.2 Hz), 3.54 (t, 2H, J=6.2 Hz), 3.40 (s, 3H), 2.8 (s, 2H) and 1.35 (s, 6H); MS (ESI+): M+H, 455.2

Example Compound 2

3-((1,3-Dioxolan-2-yl)methyl)-2-((2-methoxyethyl)thio)-5,5-dimethyl-5,6-dihydrobenzo[h]-quinazolin-4(3H)-one (CCG-204029). 9 mg (12%); $^1$H NMR (CDCl$_3$/TMS) δ 8.05 (d, 1H, J=7.6 Hz), 7.25-7.35 (m, 2H), 7.16 (m, 1H), 5.41 (t, 1H, J=4.9 Hz), 4.2 (d, 2H, J=4.9 Hz), 4.05-4.10 (m, 2H), 3.85-3.95 (m, 2H), 3.75 (t, 2H, J=6.3 Hz), 3.53 (t, 2H, J=6.3 Hz), 2.8 (s, 2H) and 1.3 (s, 6H).

Example Compound 3

4-(2-((2-Methoxyethyl)thio)-5,5-dimethyl-4-oxo-5,6-dihydrobenzo[h]quinazolin-3(4H)-yl)butanenitrile (CCG-204031). 21 mg (29%); $^1$H NMR (CDCl$_3$/TMS) δ 8.03 (d, 1H, J=7.6 Hz), 7.28-7.37 (m, 2H), 7.18 (d, 1H, J=6.97 Hz), 4.16 (d, 2H, J=7.42 Hz), 3.76 (t, 2H, J=6.1 Hz), 3.53 (t, 2H, J=6.2 Hz), 2.78 (s, 2H), 2.46 (t, 2H, J=7.4 Hz), 2.15 (qt, 2H, J=7.4 Hz) and 1.3 (s, 6H).

Example Compound 4

3-(4-Methoxybenzyl)-2-((2-methoxyethyl)thio)-5,5-dimethyl-5,6-dihydrobenzo[h]quin-azolin-4(3H)-one (CCG-204036) 14 mg (34%); $^1$H NMR (CDCl$_3$/TMS) δ 8.04 (d, 1H, J=7.6 Hz), 7.28-7.35 (m, 4H), 7.16 (d, 1H, J=6.9 Hz), 6.83 (d, 2H, J=8.7 Hz), 5.24 (s, 2H), 3.77 (s, 3H), 3.72 (t, 2H, J=6.2 Hz), 3.49 (t, 2H, J=6.2 Hz), 3.39 (s, 3H), 2.8 (s, 2H) and 1.32 (s, 6H); MS (ESI+): M+H, 437.2

Example Compound 5

2-((2-Methoxyethyl)thio)-5,5-dimethyl-3-(4-(5-methyl-1,2,4-oxadiazol-3-yl)benzyl)-5,6-dihydrobenzo[h]quinazolin-4(3H)-one (CCG-205387) 48 mg (44%); $^1$H NMR (CDCl$_3$/TMS) δ 8.08 (dd, 1H, J=7.5 & 1.5 Hz), 8.03 (d, 2H, J=8.5 Hz), 7.44 (d, 2H, J=8.5 Hz), 7.30-7.38 (m, 2H), 7.19 (d, 1H, J=7.1 Hz), 5.36 (s, 2H), 3.73 (t, 2H, J=6.2 Hz), 3.50 (t, 2H, J=6.2 Hz), 3.39 (s, 3H), 2.82 (s, 2H), 2.64 (s, 3H) and 1.41 (s, 6H); MS (ESI+): M+H, 489.2.

Example Compound 6

3-(3-Hydroxypropyl)-2-((2-methoxyethyl)thio)-5,5-dimethyl-5,6-dihydrobenzo[h]quinazolin-4(3H)-one (CCG-205390). 22 mg (27%); $^1$H NMR (CDCl$_3$/TMS) δ 8.06 (d, 1H, J=7.5 Hz), 7.29-7.38 (m, 2H), 7.19 (d, 1H, J=7.2 Hz), 4.28 (t, 2H, J=6.1 Hz), 3.78 (t, 4H, J=6.1 Hz), 3.51-3.57 (m, 5H), 3.43 (s, 3H), 2.78 (s, 2H), 2.0 (m, 3H) and 1.3 (s, 6H).

Example Compound 7

3-(Cyclopropylmethyl)-2-((2-methoxyethyl)thio)-5,5-dimethyl-5,6-dihydrobenzo[h]quinazolin-4(3H)-one (CCG-205444), 10h: 39 mg (48%); $^1$H NMR (CDCl$_3$/TMS) δ 8.07 (d, 1H, J=7.1 Hz), 7.28-7.37 (m, 2H), 7.19 (d, 1H, J=5.8 Hz), 4.00 (d, 2H, J=7.1 Hz), 3.78 (t, 2H, J=6.2 Hz), 3.55 (t, 2H, J=6.2 Hz), 3.42 (s, 3H), 2.8 (s, 2H), 1.3 (s, 7H) and 0.53 (d, 4H, J=6.5 Hz).

Example Compound 8

4-(2-(4-Fluorophenoxy)ethoxy)-2-((2-methoxyethyl)thio)-5,5-dimethyl-5,6-dihydrobenzo[h]-quinazoline (CCG-204028). 26 mg (30%); $^1$H NMR (CDCl$_3$/TMS) δ 8.05 (d, 1H, J=7.42 Hz), 7.28-7.36 (m, 2H), 7.15 (m, 1H), 6.93-7.0 (m, 2H), 6.82-6.89 (m, 2H), 4.73 (t, 2H, J=4.8 Hz), 4.27 (t, 2H, J=4.8 Hz), 3.73 (t, 2H, J=6.8 Hz), 3.38-3.45 (m, 5H), 2.8 (s, 2H) and 1.3 (s, 6H).

Example Compound 9

4-((1,3-dioxolan-2-yl)methoxy)-2-((2-methoxyethyl)thio)-5,5-dimethyl-5,6-dihydrobenzo[h]-quinazoline (CCG-204030). 34 mg (45%); $^1$H NMR (CDCl$_3$/TMS) δ 8.20 (d, 1H, J=7.15 Hz), 7.26-7.37 (m, 2H), 7.15 (m, 1H), 5.29 (t, 1H, J=4.03 Hz), 4.46 (d, 2H, J=4.04 Hz), 3.90-4.05 (m, 4H), 3.72 (t, 2H, J=6.8 Hz), 3.35-3.43 (m, 5H), 2.8 (s, 2H) and 1.3 (s, 6H).

Example Compound 10

4-(2-(2-Methoxyethoxy)ethoxy)-2-((2-methoxyethyl)thio)-5,5-dimethyl-5,6-dihydrobenzo[h]-quinazoline (CCG-204033). 10 mg (24%); $^1$H NMR (CDCl$_3$/TMS) δ 8.20 (d, 1H, J=7.1 Hz), 7.28-7.35 (m, 2H), 7.15 (d, 1H, J=6.6 Hz), 4.57 (t, 2H, J=4.9 Hz), 3.86 (t, 2H, J=4.9 Hz), 3.72 (t, 2H, J=6.9 Hz), 3.65-3.8 (m, 2H), 3.35-3.43 (m, 8H), 2.8 (s, 2H) and 1.3 (s, 6H).

Example Compound 11

4-((4-Methoxybenzyl)oxy)-2-((2-methoxyethyl)thio)-5,5-dimethyl-5,6-dihydrobenzo[h]-quinazoline (CCG-204037). 12 mg (29%); $^1$H NMR (CDCl$_3$/TMS) δ 8.20 (d, 1H, J=7.0 Hz), 7.26-7.4 (m, 5H), 7.15 (d, 1H, J=6.6 Hz), 6.9 (m, 2H), 5.4 (s, 2H), 3.81 (s, 3H), 3.73 (t, 2H, J=6.9 Hz), 3.38-3.43 (m, 5H), 2.8 (s, 2H) and 1.3 (s, 6H).

Example Compound 12

1-(3,4-Difluorophenyl)-2-((2-((2-methoxyethyl)thio)-5,5-dimethyl-5,6-dihydrobenzo[h]-quinazolin-4-yl)oxy)ethanone (CCG-204040). 52 mg (50%); $^1$H NMR (CDCl$_3$/TMS) δ 8.19 (dd, 1H, J=7.5 & 1.3 Hz), 7.73-7.84 (m, 2H), 7.24-7.38 (m, 3H), 7.17 (d, 1H, J=6.4 Hz), 5.6 (s, 2H), 3.61 (t, 2H, J=6.8 Hz), 3.32 (s, 3H), 3.26 (t, 2H, J=6.8 Hz), 2.8 (s, 2H) and 1.3 (s, 6H).

Example Compound 13

3-((2-((2-Methoxyethyl)thio)-5,5-dimethyl-5,6-dihydrobenzo[h]quinazolin-4-yl)oxy)propan-1-ol (CCG-205384). 14 mg (17%); $^1$H NMR (CDCl$_3$/TMS) δ 8.22 (dd, 1H, J=7.2 & 1.7 Hz), 7.3-7.38 (m, 2H), 7.17 (d, 1H, J=5.8 Hz), 4.59 (t, 2H, J=6.2 Hz), 3.7-3.82 (m, 4H), 3.39-3.46 (m, 5H), 2.8 (s, 2H), 2.05 (m, 3H) and 1.3 (s, 6H).

Example Compound 14

4-(Cyclopropylmethoxy)-2-((2-methoxyethyl)thio)-5,5-dimethyl-5,6-dihydrobenzo[h]quin-azoline (CCG-205445) 36 mg (44%); $^1$H NMR (CDCl$_3$/TMS) δ 8.07 (dd, 1H, J=7.1 & 1.9 Hz), 7.29-7.37 (m, 2H), 7.19 (d, 1H, J=6.6 Hz), 4.23 (d, 2H, J=7.2 Hz), 3.74 (t, 2H, J=6.9 Hz), 3.42 (s, 3H), 3.40 (t, 2H, J=6.9 Hz), 2.81 (s, 2H), 1.36 (s, 6H) 1.30 (m, 1H), 0.60 (m, 2H) and 0.35 (m, 2H); MS (ESI+): M+H, 371.2

Example Compound 15

9-methoxy-3,5,5-trimethyl-2-((2,2,2-trifluoroethyl)thio)-5,6-dihydrobenzo[h]quinazolin-4(3H)-one (CCG-211790). Synthesized in a manner consistent with Example 1 from B2a and methyl tosylate. Isolated 32 mg (57% yield). $^1$H NMR (500 MHz, Chloroform-d) δ 7.62 (d, J=2.6 Hz, 1H), 7.10 (d, J=8.2 Hz, 1H), 6.93 (dd, J=8.2, 2.6 Hz, 1H), 4.18 (q, J=9.7 Hz, 2H), 3.85 (s, 3H), 3.56 (s, 3H), 2.73 (s, 2H), 1.37 (s, 6H).

Example Compound 16

2-((3-(cyanomethyl)-9-methoxy-5,5-dimethyl-4-oxo-3,4,5,6-tetrahydrobenzo[h]quinazolin-2-yl)thio)acetonitrile (CCG-212012). Synthesized in a manner consistent with Example 1 from B2c and a-chloroacetonitrile. Isolated 15 mg (22% yield). $^1$H NMR (400 MHz, Chloroform-d) δ 7.76 (d, J=2.6 Hz, 1H), 7.12 (d, J=8.2 Hz, 1H), 6.97 (dd, J=8.2, 2.6 Hz, 1H), 4.96 (s, 2H), 4.10 (s, 2H), 3.88 (s, 3H), 2.75 (s, 2H), 1.37 (s, 6H).

Example Compound 17

2-(ethylthio)-4,9-dimethoxy-5,5-dimethyl-5,6-dihydrobenzo[h]quinazoline (CCG-211793). Synthesized in a manner consistent with Example 1 from B2b and methyl p-toluenesulfonic ester. Isolated 18 mg (31% yield). $^1$H NMR (500 MHz, Chloroform-d) δ 7.81 (d, J=2.7 Hz, 1H), 7.08 (d, J=8.2 Hz, 1H), 6.91 (dd, J=8.2, 2.7 Hz, 1H), 4.00 (s, 3H), 3.87 (s, 3H), 3.21 (q, J=7.3 Hz, 2H), 2.73 (s, 2H), 1.48 (t, J=7.3 Hz, 3H), 1.30 (s, 6H).

Example Compound 18

2-((4-(allyloxy)-9-methoxy-5,5-dimethyl-5,6-dihydrobenzo[h]quinazolin-2-yl)thio)acetonitrile (CCG-212010). Synthesized in a manner consistent with Example 1 from B2c and allyl bromide. Isolated 22 mg (33% yield). $^1$H NMR (400 MHz, Chloroform-d) δ 7.83 (d, J=2.7 Hz, 1H), 7.08 (d, J=8.2 Hz, 1H), 6.93 (dd, J=8.2, 2.7 Hz, 1H), 6.08 (ddt, J=16.7, 10.6, 5.6 Hz, 1H), 5.41 (dd, J=16.7, 1.4 Hz, 1H), 5.29 (dd, J=10.6, 1.1 Hz, 1H), 4.96 (d, J=5.6 Hz, 2H), 3.90-3.85 (m, 5H), 2.74 (s, 2H), 1.34 (s, 6H).

Example Compound 19

2-((4-(cyanomethoxy)-9-methoxy-5,5-dimethyl-5,6-dihydrobenzo[h]quinazolin-2-yl)thio)acetonitrile (CCG-212011). Synthesized in a manner consistent with Example 1 from B2c and a-chloroacetonitrile. Isolated 26 mg (39% yield). $^1$H NMR (400 MHz, Chloroform-d) δ 7.84 (d, J=2.7 Hz, 1H), 7.12 (d, J=8.3 Hz, 1H), 6.98 (dd, J=8.3, 2.7 Hz, 1H), 5.12 (s, 2H), 3.92 (s, 2H), 3.89 (s, 3H), 2.78 (s, 2H), 1.34 (s, 6H).

Example Compound 20

2-(ethylthio)-3-(2-methoxyethyl)-5,5-dimethyl-5,6-dihydrobenzo[h]quinazolin-4(3H)-one (CCG-203802). Prepared from C2 in a manner similar to the preparation of H5 using iodoethane as the alkylating agent (27 mg, 58% yield). $^1$H NMR (500 MHz, cdcl$_3$) δ 8.11 (dd, J=7.5, 1.5, 1H), 7.35 (td, J=7.5, 1.5, 1H), 7.31 (td, J=7.5, 1.5, 1H), 7.18 (d, J=6.9, 1H), 4.26 (t, J=6.4, 2H), 3.71 (t, J=6.4, 2H), 3.40 (s, 3H), 3.32 (q, J=7.4, 2H), 2.79 (s, 2H), 1.48 (t, J=7.4, 3H), 1.38 (s, 6H). TOF ES+ MS: 345.2 (M+H), 367.2 (M+Na).

Example Compound 21

3-Allyl-8-(2-(diethylamino)ethoxy)-2-(ethylthio)-5,5-dimethyl-5,6-dihydrobenzo[h]-quinazolin-4(3H)-one (CCG-205396). Cesium carbonate (0.10 g, 0.32 mmol) was added to a stirred solution of 3-allyl-2-(ethylthio)-8-hydroxy-5,5-dimethyl-5,6-dihydrobenzo[h]quinazolin-4(3H)-one (0.03 g, 0.09 mmol) in dimethylformamide, and after 5 minutes 2-(diethylamino)-ethyl chloride hydrochloride (0.02 g, 0.11 mmol) was added. After 18 hours at room temperature the mixture was diluted with water and stirred for 90 minutes, then extracted with ethyl acetate three times. The combined extracts were washed with water then saturated brine, and dried over MgSO$_4$. The solvent was removed under reduced pressure leaving the product (0.03 g) as a pale yellow gum; mass spec ES+m/z=442 (m+1); $^1$H NMR (500 MHz, dmso) δ 8.00 (d, 1H), 6.91 (dd, 1H), 6.85 (s, 1H), 5.96-5.74 (m, 1H), 5.21 (d, 1H), 5.13 (d, 1H), 4.59 (d, 2H), 4.07 (t, 2H), 3.29 (q, 2H), 2.78 (t, 2H), 2.75 (s, 2H) 2.56 (q, 4H), 1.39 (t, 3H), 1.29 (s, 6H), 0.98 (t, 6H).

Example Compound 22

3-allyl-2-(ethylthio)-8-isobutoxy-5,5-dimethyl-5,6-dihydrobenzo[h]quinazolin-4(3H)-one (CCG-205426). Prepared in a manner similar to that employed for Example 21. Yield: 72% mass spec ES+m/z=399, 421 (m+1, m+23). $^1$H NMR (500 MHz, DMSO) δ 8.05 (d, 1H), 6.96 (d, 1H), 6.90 (s, 1H), 5.92 (m, 1H), 5.27 (d, 1H), 5.18 (d, 1H), 4.64 (d, 2H), 3.87 (d, 2H), 3.34 (q, 2H), 2.80 (s, 2H), 2.09 (h, 1H), 1.44 (t, 3H), 1.34 (s, 6H), 1.05 (d, 6H).

Example Compound 23

2-(2-((3-allyl-2-(ethylthio)-5,5-dimethyl-4-oxo-3,4,5,6-tetrahydrobenzo[h]quinazolin-8-yl)oxy)ethyl)isoindoline-1,3-dione (CCG-206176). Prepared in a manner similar to that employed for Example 21. Yield 28%. $^1$H NMR (500 MHz, DMSO) δ 7.92 (d, 1H), 7.87-7.79 (m, 4H), 6.83 (d, 1H), 6.76 (s, 1H), 5.85-5.75 (m, 1H), 5.17 (d, 1H), 5.08 (d, 1H), 4.52 (d, 2H), 4.23 (t, 2H), 3.95 (t, 2H), 3.23 (q, 2H), 2.65 (d, 2H), 1.33 (t, 3H), 1.21 (s, 6H).

Example Compound 24

3-allyl-8-benzoyl-5,5-dimethyl-2-(prop-2-yn-1-ylthio)-5,6-dihydrobenzo[h]quinazolin-4(3H)-one (CCG-204080). Prepared in a manner similar to Example 20 using propargyl bromide as the alkylating agent. Isolated 23 mg (70% yield). $^1$H NMR (500 MHz, Chloroform-d) δ 8.27 (d, J=8.0 Hz, 1H), 7.83 (d, J=7.6 Hz, 2H), 7.73 (d, J=8.0 Hz, 1H), 7.66 (s, 1H), 7.61 (t, J=7.6 Hz, 1H), 7.51 (t, J=7.6 Hz, 2H), 5.97-5.87 (m, 1H), 5.35-5.27 (m, 2H), 4.68 (d, J=5.5 Hz, 2H), 4.07 (d, J=2.6 Hz, 2H), 2.87 (s, 2H), 2.27 (t, J=2.6 Hz, 1H), 1.41 (s, 6H).

Example Compound 25

3-allyl-2-((2-methoxyethyl)thio)-5,5-dimethyl-5,6-dihydropyrido[3,4-h]quinazolin-4(3H)-one (CCG-204041). To a solution of 3-allyl-5,5-dimethyl-2-thioxo-2,3,5,6-tetrahydropyrido[3,4-h]quinazolin-4(1H)-one (0.1 g, 0.33 mmol) in DMF (10 mL) was added Cesium carbonate (0.22 g, 0.67 mmol) followed by 2-methoxyethyl 4-methylbenzenesulfonate (0.09 g, 0.40 mmol). The resulting mixture was stirred at 40° C. for 3 hours. Cooled and concentrated. Partitioned between 2M HCl and EtOAc. Separated layers and extracted aqueous phase again with EtOAc. Dried with MgSO$_4$. Filtered and concentrated. Purified by flash chromatogaphy (EtOAc/hexane). Concentration provided the title compound (0.01 g, 0.03 mmol, 8.5% yield). NMR (400 MHz, CDCl$_3$) δ 8.62 (d, J=4 Hz, 1H), 8.51 (s, 1H), 7.87 (d, J=4 Hz, 1H), 5.90-5.97 (m, 1H), 5.30-5.34 (m, 2H), 4.72 (d, J=4.5 Hz, 2H), 3.77 (t, 2H), 3.57 (t, 2H), 3.46 (s, 3H), 2.82 (s, 2H), 1.44 (s, 6H). ESI+MS m/z 358.1 (M+H$^+$).

Example Compound 26

3-allyl-N-(2-hydroxyethyl)-2-((2-methoxyethyl)thio)-5,5-dimethyl-4-oxo-1,2,3,4,5,6-hexahydrobenzo[h]quinazoline-8-carboxamide (CCG-206239) To a solution of 3-allyl-2-((2-methoxyethyl)thio)-5,5-dimethyl-4-oxo-3,4,5,6-tetrahydrobenzo[h]quinazoline-8-carboxylic acid (0.05 g, 0.13 mmol), EDC (0.03 g, 0.15 mmol), HOBT (0.02 g, 0.15 mmol) in dry THF was added ethanolamine (0.009 g, 0.15 mmol). Allowed to stir overnight at RT. Reaction quenched via the addition of water, then extracted into ethyl acetate. Washed with saturated sodium carbonate solution, water, and brine, then the organic layer was dried over MgSO$_4$, filtered, and concentrated in vacuo. Purification via flash chromatography (20-70% EtOAc:hex) isolated the title compound. (36% yield) NMR (400 MHz, CDCl$_3$) δ 8.18-8.19 (m, 1H), 8.01-8.05 (m, 1H), 7.95 (br s, 1H), 6.20-6.23 (m, 1H), 5.89-5.94 (m, 1H), 5.26-5.31 (m, 2H), 4.58-4.63

(m, 2H), 3.72-3.78 (4H, M), 3.49-3.52 (m 2H), 3.42 (s, 3H), 2.94-2.95 (m, 2H), 2.80 (s, 2H), 1.37 (s, 6H). ESI-MS m/z 443.2 (M+H$^+$).

Example Compound 27

3-Allyl-2-((2-methoxyethyl)thio)-3H-spiro[benzo[h]quinazoline-5,4'-piperidin]-4(6H)-one, (CCG-205447): To a solution of the compound (50 mg) in DCM (2.5 mL) was added TFA (0.25 mL). The reaction mixture was stirred at RT for 1 h. TLC indicated complete disappearance of the starting material. The reaction mixture was washed with saturated NaHCO$_3$ (2×1 mL) solution and water (2×1 mL), dried over Na$_2$SO$_4$, filtered and the solvent was removed under reduced pressure to yield the product. 3-Allyl-2-((2-methoxyethyl)thio)-3H-spiro[benzo[h]quinazoline-5,4'-piperidin]-4(6H)-one, 17: 0.20 g (91%). $^1$H NMR (CDCl$_3$/TMS) δ 8.07 (d, 1H, J=7.5 Hz), 7.30-7.39 (m, 2H), 7.23 (d, 1H, J=7.1 Hz), 5.94 (m, 1H), 5.28 (m, 2H), 4.69 (d, 2H, J=5.6 Hz), 3.76 (t, 2H, J=6.2 Hz), 3.53 (t, 2H, J=6.2 Hz), 3.4 (s, 3H), 3.12 (s, 2H), 2.96 (m, 4H), 2.75 (m, 2H), 2.17 (s, 1H) and 1.35 (d, 2H, J=13.3 Hz).

General Acylation Procedure for Example Compounds 28-31

To a solution of the compound 17 (0.09-0.126 mmole) in DCM 0.7 mL were added the acid chloride (1 equivalent, 7 equivalents in the case of AcCl) and TEA (1.2-3 equivalents) and the reaction mixture was stirred at RT for 2h. TLC indicated formation of product. The reaction was diluted by adding 1 mL of DCM. The organic layer was washed with 1N HCl (1 mL) followed by H$_2$O (2×1 mL), dried (Na$_2$SO$_4$), decanted and the solvent was removed under reduced pressure to yield the crude compound. The crude compound was purified by flash chromatography using EtOAc/hexane.

Example Compound 28

3-Allyl-2-((2-methoxyethyl)thio)-1'-pentanoyl-3H-spiro[benzo[h]quinazoline-5,4'-piperidin]-4(6H)-one (CCG-206227): 36 mg (59%); $^1$H NMR (CDCl$_3$/TMS) δ 8.07 (d, 1H, J=7.5 Hz), 7.32-7.39 (m, 2H), 7.22 (d, 1H, J=7.0 Hz), 5.91 (m, 1H), 5.28 (m, 2H), 4.69 (d, 2H, J=5.5 Hz), 4.38 (d, 1H, J=13.2 Hz), 3.74-3.84 (m, 3H), 3.54 (t, 2H, J=6.2 Hz), 3.33-3.44 (m, 4H), 3.17 (d, 1H, J=17.6 Hz), 2.98-3.06 (m, 2H), 2.88-2.97 (m, 1H), 2.48 (td, 1H, J=13.2 & 4.8 Hz), 2.33 (t, 2H, J=7.1 Hz), 1.58-1.7 (m, 2H), 1.32-1.48 (m, 4H) and 0.93 (t, 3H, J=7.3 Hz).

Example Compound 29

1'-Acetyl-3-allyl-2-((2-methoxyethyl)thio)-3H-spiro[benzo[h]quinazoline-5,4'-piperidin]-4(6H)-one (CCG-206230): 28 mg (66%); $^1$H NMR (CDCl$_3$/TMS) δ 8.08 (d, 1H, J=7.5 Hz), 7.33-7.41 (m, 2H), 7.22 (d, 1H, J=7.0 Hz), 5.91 (m, 1H), 5.28 (m, 2H), 4.68 (m, 2H), 4.38 (d, 1H, J=13.6 Hz), 3.76 (m, 3H), 3.54 (t, 2H, J=6.2 Hz), 3.35-3.44 (m, 4H), 3.16 (d, 1H, J=15.7 Hz), 2.98-3.06 (m, 2H), 2.88-2.97 (m, 1H), 2.48 (td, 1H, J=13.2 & 5.0 Hz), 2.10 (s, 3H) and 1.43 (m, 2H).

Example Compound 30

3-Allyl-1'-benzoyl-2-((2-methoxyethyl)thio)-3H-spiro[benzo[h]quinazoline-5,4'-piperidin]-4(6H)-one (CCG-206231): 16 mg (33%); $^1$H NMR (CDCl$_3$/TMS) δ 8.08 (d, 1H, J=7.3 Hz), 7.44-7.48 (m, 2H), 7.33-7.41 (m, 5H), 7.22 (d, 1H, J=6.6 Hz), 5.93 (m, 1H), 5.29 (m, 2H), 4.70 (d, 2H, J=15.5 Hz), 4.46-4.56 (m, 1H), 3.76 (t, 3H, 6.2 Hz), 3.55 (t, 2H, J=6.2 Hz), 3.42 (s, 3H), 3.28-3.38 (m, 1H), 2.96-3.25 (m, 4H), 2.58-2.69 (m, 1H) and 1.32-1.56 (m, 2H).

Example Compound 31

3-Allyl-1'-(4-chlorobenzoyl)-2-((2-methoxyethyl)thio)-3H-spiro[benzo[h]quinazoline-5,4'-piperidin]-4(6H)-one (CCG-206235) 33 mg (75%); $^1$H NMR (CDCl$_3$/TMS) δ 8.08 (dd, 1H, J=7.5 & 1.5 Hz), 7.34-7.43 (m, 6H), 7.23 (d, 1H, J=6.9 Hz), 5.92 (m, 1H), 5.30 (m, 2H), 4.70 (d, 2H, J=5.5 Hz), 4.47-4.52 (m, 1H), 3.77 (t, 3H, 6.2 Hz), 3.70 (m, 1H), 3.55 (t, 2H, J=6.2 Hz), 3.42 (s, 3H), 2.98-3.40 (m, 4H), 2.6 (m, 1H) and 1.32-1.55 (m, 2H); MS (ESI+): M+H, 536.2 & 538.2.

Example Compound 32

3-Allyl-2-((2-methoxyethyl)thio)-4-oxo-4,6-dihydro-3H-spiro[benzo[h]quinazoline-5,4'-piperidine]-1'-carbaldehyde (CCG-206234): To a solution of the compound 17 (0.043) in toluene (0.2 mL) at RT was added DBU (0.01 mL) and the reaction mixture was stirred at RT for 2 h. TLC indicated formation of product as well as the presence of the starting material. It was allowed to stir at RT for a further 15 h. Powdered KHSO$_4$ (50 mg) was added and the mixture was stirred for an hour. The reaction mixture was filtered and the solvent was removed. The residue was applied on a column of silica gel (4 g) and eluted with a gradient of 16-90% EtOAc/hexane over 120 mL at 12 mL/minute. Isolated 13 mg (28% yield); $^1$H NMR (CDCl$_3$/TMS) δ 8.09 (dd, 1H, J=7.3 & 1.4 Hz), 8.04 (s, 1H), 7.33-7.42 (m, 2H), 7.24 (d, 1H, J=7.0 Hz), 5.91 (m, 1H), 5.29 (m, 2H), 4.68 (m, 2H), 4.27 (dd, 1H, J=13.7 & 5 Hz), 3.76 (t, 2H, 6.2 Hz), 3.54 (t, 3H, J=6.2 Hz), 3.43 (s, 3H), 3.35-3.41 (m, 1H), 3.18 (d, 1H, J=15.7 Hz), 3.07 (d, 1H, J=15.6 Hz), 3.00 (td, 1H, J=12.9 & 5.2 Hz), 2.92 (td, 1H, J=13.4 & 3.3 Hz), 2.59 (td, 1H, J=13.4 & 5.3 Hz) and 1.40-1.50 (m, 2H).

Example Compound 33

3-Allyl-2-((2-methoxyethyl)thio)-2',3',5',6'-tetrahydro-3H-spiro[benzo[h]quinazoline-5,4'-pyran]-4(6H)-one, (CCG-205453) To a solution of the compound (40 mg, 0.12 mmole) in DMF (0.7 mL) was added Cs$_2$CO$_3$ (77 mg, 0.24 mmole). The reaction mixture was stirred for 3 minutes. Then the 2-methoxyethyl p-toluenesulfonic ester (30 mg, 0.12 mmole) was added and the reaction was stirred at 70° C. for 3 h. TLC indicated completion of reaction. The solvent was removed under reduced pressure and the residue was extracted with EtOAc (2 mL) and H$_2$O (2 mL), the separated organic layer was washed with H$_2$O (2×1 mL), dried (Na$_2$SO$_4$) and the solvent was removed under reduced pressure to yield the crude product. It was purified by flash chromatography using 4 g Silicycle column. The column was eluted first with 4% EtOAc/DCM for 2 min at 12 mL/minute and followed by a gradient from 4-20% gradient over 60 mL. The desired fractions were pooled, after TLC, and the solvent was removed under reduced pressure to yield the purified product. Yield: 39 mg (83%); R$_f$=0.59 (1:1, EtOAc/hexanes). $^1$H NMR (CDCl$_3$/TMS) δ 8.09 (d, 1H, J=7.4 Hz), 7.3-7.4 (m, 2H), 7.24 (d, 1H, J=7.1 Hz), 5.94 (m, 1H), 5.29 (m, 2H), 4.70 (d, 2H, J=6.6 Hz), 3.7-3.88 (m, 6H), 3.54 (t, 2H, 6.2 Hz), 3.41 (s, 3H), 3.18 (s, 2H), 3.01 (td, 2H, J=13 & 6.3 Hz) and 1.27 (d, 2H, J=13.5 Hz); MS (ESI+): M+H, 399.2 & M+Na, 421.2

Example Compound 34 tert-butyl 3-allyl-2-((2-methoxyethyl)thio)-4-oxo-4,6-dihydro-3H-spiro[benzo[h]quinazoline-5,3'-pyrrolidine]-1'-carboxylate (CCG-208860). Compound was prepared in a manner similar to the synthesis of entry K3 using J3a as starting material and 2-methoxyethyl p-toluenesulfonic ester and allyl bromide as the first and second alkylating agents. Isolated 40 mg (30% yield). $^1$H NMR (400 MHz, Chloroform-d) δ 8.10 (t, J=7.2 Hz, 1H), 7.41-7.30 (m, 2H), 7.19 (d, J=7.2 Hz, 1H), 5.92 (d, J=5.6 Hz, 1H), 5.30 (d, J=18.7 Hz, 2H), 4.69 (d, J=4.9 Hz, 2H), 3.99 (dd, J=32.9, 10.8 Hz, 1H), 3.76 (t, J=6.1 Hz, 2H), 3.63-3.45 (m, 4H), 3.42 (s, 3H), 3.27 (dd, J=39.4, 10.4 Hz, 1H), 2.96 (q, J=15.9 Hz, 3H), 1.70-1.62 (m, 1H), 1.45 (d, J=15.7 Hz, 9H).

Example Compound 35 tert-butyl 3-allyl-8-methoxy-2-((2-methoxyethyl)thio)-4-oxo-4,6-dihydro-3H-spiro[benzo[h]quinazoline-5,3'-pyrrolidine]-1'-carboxylate (CCG-208864). Compound was prepared in a manner similar to the synthesis of entry K3 using J3b as starting material and 2-methoxyethyl p-toluenesulfonic ester and allyl bromide as the first and second alkylating agents. Isolated 68 mg (20% yield). $^1$H NMR (400 MHz, Chloroform-d) δ 8.03 (d, J=8.4 Hz, 1H), 6.85 (d, J=8.7 Hz, 1H), 6.70 (s, 1H), 5.89 (s, 1H), 5.28 (d, J=19.5 Hz, 2H), 4.67 (d, J=4.9 Hz, 2H), 3.97 (dd, J=43.4, 10.2 Hz, 1H), 3.85 (s, 3H), 3.74 (t, J=6.1 Hz, 2H), 3.62-3.43 (m, 4H), 3.41 (s, 3H), 3.25 (dd, J=40.4, 10.6 Hz, 1H), 3.15-2.83 (m, 3H), 1.70-1.59 (m, 1H), 1.44 (d, J=14.0 Hz, 9H).

Example Compound 36

3-allyl-8-methoxy-2-((2-methoxyethyl)thio)-3H-spiro[benzo[h]quinazoline-5,3'-pyrrolidine]-4(6H)-one hydrochloride (CCG-208865). Example 35 (30 mg, 0.058 mmol) was dissolved in 4M HCl-dioxane and the mixture allowed to stir for 1 hour, causing the precipitation of a white solid. Solid collected via filtration and washed with cold diethyl ether, then dried under vacuum. Isolated 20 mg (76% yield). $^1$H NMR (400 MHz, Chloroform-d) δ 11.62 (s, 1H), 8.16 (s, 1H), 8.03 (d, J=8.4 Hz, 1H), 6.90 (d, J=8.4 Hz, 1H), 6.81 (s, 1H), 5.97-5.80 (m, 1H), 5.38-5.20 (m, 2H), 4.78-4.59 (m, 2H), 4.05-3.92 (m, 1H), 3.88 (s, 3H), 3.75 (t, J=6.0 Hz, 3H), 3.65-3.51 (m, 3H), 3.42 (s, 3H), 3.38-3.16 (m, 2H), 2.87 (s, 1H), 2.26-1.99 (m, 2H).

Example Compound 37 tert-butyl 3-allyl-8-methoxy-2-((2-methoxyethyl)thio)-4-oxo-4,6-dihydro-3H-spiro[benzo[h]quinazoline-5,4'-piperidine]-1'-carboxylate (CCG-206660). Compound was prepared in a manner similar to the synthesis of entry K3 using 2-methoxyethyl p-toluenesulfonic ester and allyl bromide as the first and second alkylating agents. Isolated 49 mg (40% yield). $^1$H NMR (400 MHz, Chloroform-d) δ 9.97 (s, 1H), 8.74 (s, 1H), 8.01 (d, J=8.6 Hz, 1H), 6.87 (d, J=8.6 Hz, 1H), 6.79 (s, 1H), 5.95-5.83 (m, 1H), 5.28-5.19 (m, 2H), 4.68 (d, J=4.2 Hz, 2H), 3.87 (s, 3H), 3.75 (t, J=6.1 Hz, 2H), 3.53 (t, J=6.1 Hz, 2H), 3.50-3.43 (m, 2H), 3.42 (s, 3H), 3.36-3.21 (m, 2H), 3.02 (s, 2H), 2.99-2.84 (m, 2H), 1.69 (d, J=13.7 Hz, 2H).

Example Compound 38 tert-butyl 3-allyl-2-(ethylthio)-8-methoxy-4-oxo-4,6-dihydro-3H-spiro[benzo[h]quinazoline-5,4'-piperidine]-1'-carboxylate (CCG-206663). Synthesized in a manner similar to entry K3 using iodoethane then allyl bromide as the alkylating agents. Isolated 30 mg (52% yield). $^1$H NMR (400 MHz, Chloroform-d) δ 8.05 (d, J=8.6 Hz, 1H), 6.86 (dd, J=8.6, 2.4 Hz, 1H), 6.74 (d, J=2.4 Hz, 1H), 5.92 (ddt, J=15.9, 10.8, 5.5 Hz, 1H), 5.30-5.22 (m, 2H), 4.65 (d, J=5.5 Hz, 2H), 4.07-3.89 (m, 2H), 3.86 (s, 3H), 3.30 (q, J=7.3 Hz, 2H), 3.19-2.86 (m, 5H), 2.69-2.52 (m, 1H), 1.51-1.42 (m, 12H), 1.42-1.32 (m, 2H).

Example Compound 39 tert-butyl 2-((cyanomethyl)thio)-8-methoxy-3-methyl-4-oxo-4,6-dihydro-3H-spiro[benzo[h]quinazoline-5,4'-piperidine]-1'-carboxylate (CCG-211811). Compound K2 (500 mg, 1.16 mmol) was dissolved in DMF (7 mL), to which sodium bicarbonate (108 mg, 1.28 mmol) and a-chloroacetonitrile (78 µL, 1.222 mmol) were added. The solution was allowed to stir at RT for 3 hours, at which time the reaction was diluted with water (30 mL), precipitating a yellow solid. This solid was collected via vacuum filtration, and washed with water and hexanes. Drying on high vacuum yielded an S-alkylated intermediate (490 mg, 90% yield). A portion of this solid (170 mg, 0.36 mmol) was redissolved in DMF (2 mL). To this solution was added cesium carbonate (142 mg, 0.44 mmol) and methyl tosylate (74 mg, 0.40 mmol). The reaction was warmed to 50° C. and allowed to stir overnight. The reaction was halted by the addition of water, and the aqueous mixture was extracted 2× with ethyl acetate. The combined organic extract was washed with water and brine, then dried over MgSO$_4$, filtered, and concentrated to a crude mixture of N- and O-alkylated products. Further purification via flash chromatography (10-40% EtOAc:hex) yielded the N-alkylated product as a white solid (26 mg, 15% yield). $^1$H NMR (500 MHz, Chloroform-d) δ 8.11 (d, J=8.6 Hz, 1H), 6.89 (dd, J=8.6, 2.5 Hz, 1H), 6.74 (d, J=2.5 Hz, 1H), 4.06 (s, 2H), 4.04-3.90 (m, 2H), 3.87 (s, 3H), 3.49 (s, 3H), 3.17-2.93 (m, 4H), 2.93-2.75 (m, 1H), 2.72-2.52 (m, 1H), 1.47 (s, 9H), 1.43-1.33 (m, 2H).

Example Compound 40 tert-butyl 2-((cyanomethyl)thio)-4,8-dimethoxy-6H-spiro[benzo[h]quinazoline-5,4'-piperidine]-1'-carboxylate (CCG-211810). Compound was isolated from the crude reaction mixture to generate Example 39 via flash chromatography. Isolated 29 mg (17% yield). $^1$H NMR (500 MHz, Chloroform-d) δ 8.19 (d, J=8.6 Hz, 1H), 6.89 (dd, J=8.6, 2.6 Hz, 1H), 6.73 (d, J=2.6 Hz, 1H), 4.10-3.85 (bm, 2H), 4.03 (s, 3H), 3.92 (s, 2H), 3.86 (s, 3H), 3.13-3.00 (m, 4H), 2.46 (s, 2H), 1.49 (s, 9H), 1.46 (s, 2H).

Example Compound 41 tert-butyl 4-(cyanomethoxy)-2-((cyanomethyl)thio)-8-methoxy-6H-spiro[benzo[h]quinazoline-5,4'-piperidine]-1'-carboxylate (CCG-211812). Synthesized in a manner similar to Example 39 using a-chloracetonitrile as the first and second alkylating agents. Isolated 49 mg (24% yield). $^1$H NMR (500 MHz, Chloroform-d) δ 8.21 (d, J=8.6 Hz, 1H), 6.90 (dd, J=8.6, 2.5 Hz, 1H), 6.75 (d, J=2.5 Hz, 1H), 5.11 (s, 2H), 4.09-3.96 (m, 2H), 3.93 (s, 2H), 3.88 (s, 3H), 3.15-3.01 (m, 4H), 2.46-2.27 (m, 2H), 1.56-1.45 (m, 11H).

Example Compound 42

3-allyl-8-methoxy-2-((2-methoxyethyl)thio)-3H-spiro[benzo[h]quinazoline-5,4'-piperidin]-4(6H)-one hydrochloride (CCG-206661). Compound was synthesized in a manner similar to Example 36, using example compound 37 as starting material. Isolated 16 mg (82% yield). $^1$H NMR (400 MHz, Chloroform-d) δ 9.97 (s, 1H), 8.74 (s, 1H), 8.01 (d, J=8.6 Hz, 1H), 6.87 (d, J=8.6 Hz, 1H), 6.79 (s, 1H), 5.95-5.83 (m, 1H), 5.28-5.19 (m, 2H), 4.68 (d, J=4.2 Hz, 2H), 3.87 (s, 3H), 3.75 (t, J=6.1 Hz, 2H), 3.53 (t, J=6.1 Hz, 2H), 3.50-3.43 (m, 2H), 3.42 (s, 3H), 3.36-3.21 (m, 2H), 3.02 (s, 2H), 2.99-2.84 (m, 2H), 1.69 (d, J=13.7 Hz, 2H).

Example Compound 43

3-allyl-2-(ethylthio)-8-methoxy-3H-spiro[benzo[h]quinazoline-5,4'-piperidin]-4(6H)-one hydrochloride (CCG-206664). Compound was synthesized in a manner similar to Example 36, using example compound 38 as starting material. Isolated 17 mg (89% yield). $^1$H NMR (400 MHz, Chloroform-d) δ 9.98 (s, 1H), 8.77 (s, 1H), 8.05 (d, J=8.6 Hz, 1H), 6.87 (dd, J=8.6, 1.9 Hz, 1H), 6.78 (s, 1H), 6.01-5.79 (m, 1H), 5.32-5.13 (m, 2H), 4.66 (d, J=4.7 Hz, 2H), 3.87 (s, 3H), 3.55-3.41 (m, 2H), 3.35-3.22 (m, 4H), 3.02 (s, 2H), 2.98-2.85 (m, 2H), 1.69 (d, J=14.2 Hz, 2H), 1.47 (t, J=7.3 Hz, 3H).

Example Compound 44

3-allyl-8-methoxy-2-((2-methoxyethyl)thio)-1'-methyl-3H-spiro[benzo[h]quinazoline-5,4'-piperidin]-4(6H)-one (CCG-208981). Example compound 42 (30 mg, 0.065 mmol) was dissolved in 1,2-dichloroethane (400 μL), then acetic acid (5 μL, 0.080 mmol), paraformaldehyde (10 mg, 0.33 mmol), and sodium triacetoxyborohydride (21 mg, 0.100 mmol) were added. The solution was allowed to stir for 12 hours at room temperature, then was quenched by the addition of saturated aqueous sodium carbonate. The reaction was extracted with DCM twice, then the combined organic extracts were washed with water and brine, dried over MgSO4, filtered, and concentrated. Further purification via flash chromatography (0-20% methanol:DCM) furnished the title compound as a sticky yellow oil (22 mg, 77% yield). $^1$H NMR (400 MHz, Chloroform-d) δ 8.01 (d, J=8.6 Hz, 1H), 6.84 (dd, J=8.6, 2.3 Hz, 1H), 6.74 (d, J=2.3 Hz, 1H), 5.91 (ddt, J=16.2, 11.0, 5.7 Hz, 1H), 5.33-5.21 (m, 2H), 4.67 (d, J=5.7 Hz, 2H), 3.86 (s, 3H), 3.75 (t, J=6.3 Hz, 2H), 3.51 (t, J=6.3 Hz, 2H), 3.42 (s, 3H), 3.00 (s, 2H), 2.98-2.89 (m, 2H), 2.74 (d, J=11.6 Hz, 2H), 2.64 (s, 2H), 2.34 (s, 3H), 1.36 (d, J=13.5 Hz, 2H).

Example Compound 45

3-allyl-1'-benzyl-8-methoxy-2-((2-methoxyethyl)thio)-3H-spiro[benzo[h]quinazoline-5,4'-piperidin]-4(6H)-one (CCG-208982). Synthesized in a manner similar to compound 44 using benzaldehyde as the coupling partner. Isolated 23 mg (57% yield). $^1$H NMR (400 MHz, Chloroform-d) δ 7.99 (d, J=8.8 Hz, 1H), 7.64-7.51 (m, 2H), 7.44-7.29 (m, 3H), 6.88-6.81 (m, 2H), 5.98-5.85 (m, 1H), 5.34-5.24 (m, 2H), 4.71 (d, J=5.0 Hz, 2H), 3.85 (s, 3H), 3.75 (t, J=6.2 Hz, 2H), 3.53 (t, J=6.2 Hz, 2H), 3.42 (s, 3H), 3.31-3.04 (m, 4H), 3.06-2.93 (m, 3H), 1.90-1.61 (m, 5H).

Example Compound 46

3-allyl-8-methoxy-2-((2-methoxyethyl)thio)-N-methyl-4-oxo-4,6-dihydro-3H-spiro[benzo[h]quinazoline-5,4'-piperidine]-1'-carboxamide (CCG-211970). Example compound 42 (30 mg, 0.070 mmol) was dissolved in DCM (350 μL), then 0-succinimidyl methyl carbamate (24 mg, 0.140 mmol) and DIPEA (18 μL, 0.105 mmol) were added. The solution was allowed to stir 6 hours at room temperature. The reaction was halted by the addition of water, followed by extraction into DCM. The organic extract was washed with water and brine, then dried over MgSO$_4$, filtered, and concentrated in vacuo. Purification via flash chromatography (20-70% EtOAc:hex) isolated the desired compound as a white powder (22 mg, 65% yield). $^1$H NMR (500 MHz, Chloroform-d) δ 8.02 (d, J=8.6 Hz, 1H), 6.86 (dd, J=8.6, 2.5 Hz, 1H), 6.74 (d, J=2.5 Hz, 1H), 5.91 (ddt, J=15.9, 10.7, 5.6 Hz, 1H), 5.31-5.23 (m, 2H), 4.67 (d, J=5.6 Hz, 2H), 4.42 (d, J=4.6 Hz, 1H), 3.86 (s, 3H), 3.82-3.72 (m, 4H), 3.52 (t, J=6.3 Hz, 2H), 3.42 (s, 3H), 3.17 (td, J=12.7, 3.0 Hz, 2H), 3.01 (s, 2H), 2.81 (d, J=4.6 Hz, 3H), 2.74 (td, J=13.2, 4.9 Hz, 2H), 1.43 (d, J=13.6 Hz, 2H).

Example Compound 47

3-allyl-8-methoxy-2-((2-methoxyethyl)thio)-4-oxo-N-phenyl-4,6-dihydro-3H-spiro[benzo[h]quinazoline-5,4'-piperidine]-1'-carboxamide (CCG-211971). Synthesized in a manner similar to example compound 46 using phenyl isocyanate as the acylating agent. Isolated 32 mg (83% yield). $^1$H NMR (500 MHz, Chloroform-d) δ 8.04 (d, J=8.6 Hz, 1H), 7.37 (d, J=7.7 Hz, 2H), 7.32-7.25 (m, 2H), 7.02 (t, J=7.3 Hz, 1H), 6.88 (dd, J=8.6, 2.5 Hz, 1H), 6.76 (d, J=2.5 Hz, 1H), 6.39 (s, 1H), 5.92 (ddt, J=15.9, 10.8, 5.6 Hz, 1H), 5.33-5.25 (m, 2H), 4.69 (d, J=5.6 Hz, 2H), 3.94 (dt, J=13.0, 4.1 Hz, 2H), 3.88 (s, 3H), 3.76 (t, J=6.3 Hz, 2H), 3.54 (t, J=6.3 Hz, 2H), 3.43 (s, 3H), 3.31 (td, J=12.8, 3.0 Hz, 2H), 3.04 (s, 2H), 2.78 (td, J=13.6, 4.7 Hz, 2H), 1.52 (d, J=13.8 Hz, 2H).

Example Compound 48 ethyl (3-allyl-8-methoxy-2-((2-methoxyethyl)thio)-4-oxo-4,6-dihydro-3H-spiro[benzo[h]quinazoline-5,4'-piperidine]-1'-carbonyl)glycinate (CCG-211972). Synthesized in a manner similar to example compound 46, using ethyl 2-isocyanatoacetate as the acylating agent. Isolated 26 mg (67% yield). $^1$H NMR (500 MHz, Chloroform-d) δ 8.02 (d, J=8.6 Hz, 1H), 6.86 (dd, J=8.6, 2.5 Hz, 1H), 6.74 (d, J=2.5 Hz, 1H), 5.91 (ddt, J=15.9, 10.8, 5.6 Hz, 1H), 5.32-5.23 (m, 2H), 4.94 (t, J=5.0 Hz, 1H), 4.67 (d, J=5.6 Hz, 2H), 4.22 (q, J=7.1 Hz, 2H), 4.02 (d, J=5.0 Hz, 2H), 3.87 (s, 3H), 3.82 (dt, J=12.9, 4.0 Hz, 2H), 3.75 (t, J=6.3 Hz, 2H), 3.52 (t, J=6.3 Hz, 2H), 3.42 (s, 3H), 3.23 (td, J=12.7, 3.0 Hz, 2H), 3.01 (s, 2H), 2.75 (td, J=13.3, 4.8 Hz, 2H), 1.45 (d, J=13.6 Hz, 2H), 1.29 (t, J=7.1 Hz, 3H).

Example Compound 49

2((4,8-dimethoxy-6H-spiro[benzo[h]quinazoline-5,4'-piperidin]-2-yl)thio)acetonitrile (CCG-212014). Synthesized in a manner similar to that of Example compound 27 from example compound 40. Isolated 16 mg (100% yield). $^1$H NMR (400 MHz, Methanol-d$_4$) δ 8.18 (d, J=9.3 Hz, 1H), 6.98-6.91 (m, 2H), 4.12 (s, 2H), 4.10 (s, 3H), 3.86 (s, 3H), 3.43-3.25 (m, 4H), 3.20 (s, 2H), 2.75 (td, J=14.2, 5.0 Hz, 2H), 1.72 (d, J=15.2 Hz, 2H).

Example Compound 50

2-((4-(cyanomethoxy)-8-methoxy-6H-spiro[benzo[h]quinazoline-5,4'-piperidin]-2-yl)thio)acetonitrile (CCG-212015). Synthesized in a manner similar to example compound 27 using example compound 41 as substrate. Isolated 9 mg (56% yield). $^1$H NMR (400 MHz, Methanol-d$_4$) δ 8.24 (d, J=8.7 Hz, 1H), 7.02-6.89 (m, 2H), 5.28 (s, 2H), 4.16 (s, 2H), 3.87 (s, 3H), 3.43-3.33 (m, 2H), 3.33-3.26 (m, 2H), 3.24 (s, 2H), 2.67 (td, J=14.3, 13.8, 5.1 Hz, 2H), 1.80 (d, J=15.1 Hz, 2H).

Example Compound 51

1-(4-(allyloxy)-8-methoxy-2-((2-methoxyethyl)thio)-6H-spiro[benzo[h]quinazoline-5,4'-piperidin]-1'-yl)pentan-1-one (CCG-208863). Compound K3 (94 mg, 0.178 mmol) was dissolved in 4M HCl-dioxane solution (1 mL). After 30 minutes, a white solid precipitates from solution. 5 mL diethyl ether was added to the solution and the solid was collected via filtration. Washing the solid with diethyl ether and drying under high vacuum delivered 89 mg of the free amine intermediate (quant.). A portion of this material (30 mg, 0.070 mmol) was dissolved in DCM (350 µL), and DIPEA (37 µL, 0.210 mmol) and pentanoyl chloride (10 µL, 0.084 mmol) were added. After stirring at RT for 12 hours, the solvent was removed in vacuo and column chromatography (10-50% EtOAc:hex) was used to purify the final product. Isolated 27 mg (74% yield). $^1$H NMR (400 MHz, Chloroform-d) δ 8.16 (d, J=8.6 Hz, 1H), 6.87 (dd, J=8.6, 2.1 Hz, 1H), 6.73 (d, J=2.1 Hz, 1H), 6.04 (ddt, J=16.9, 10.6, 5.6 Hz, 1H), 5.35 (d, J=16.9 Hz, 1H), 5.26 (d, J=10.6 Hz, 1H), 4.91 (d, J=5.6 Hz, 2H), 4.43 (d, J=13.7 Hz, 1H), 3.86 (s, 3H), 3.72 (t, J=6.8 Hz, 2H), 3.44-3.34 (m, 6H), 3.15-3.00 (m, 2H), 2.96 (t, J=12.0 Hz, 1H), 2.57 (td, J=13.3, 4.7 Hz, 1H), 2.44 (td, J=13.3, 4.7 Hz, 1H), 2.35 (td, J=7.3, 3.4 Hz, 2H), 1.70-1.58 (m, 3H), 1.58-1.46 (m, 2H), 1.46-1.33 (m, 2H), 0.94 (t, J=7.3 Hz, 3H).

Example Compound 52

4-(2-Methoxyethoxy)-2-((2-methoxyethyl)thio)-5-methyl-6-phenylpyrimidine (CCG-205360). 2-Bromoethyl methyl ether (0.35 g, 2.4 mmol) was added in one portion to a stirred mixture of cesium carbonate (0.82 g, 2.5 mmol) and 5-methyl-6-phenyl-2-thioxo-2,3-dihydropyrimidin-4(1H)-one (N3) (0.5 g, 2.29 mmol) in dimethylformamide (5 mL) at room temperature. The mixture was heated to 70° C. for 4½ hours then allowed to cool. Additional cesium carbonate (0.82 g, 2.5 mmol) was added followed by bromoethyl methyl ether (0.4 g, 2.9 mmol). After 18 hours the mixture was poured into water and stirred, then extracted with dichloromethane three times. The combined extracts were washed with water then saturated brine, and dried over MgSO$_4$. The solvent was removed in vacuo and further purification via flash chromatography (25-33% EtOAc:hex) furnished the title compound (0.4 g) as a clear colorless oil; mass spec ES+ m/z=335, 357 (m+1, m+23); $^1$H NMR (500 MHz, dmso) δ 7.58 (dd, 2H), 7.54-7.40 (m, 3H), 4.51 (t, 2H), 3.70 (t, 2H), 3.60 (t, 2H) 3.31 (s, 6H), 3.30 (m, 2H), 2.09 (s, 3H).

Example Compound 53

3-allyl-2-((2-methoxyethyl)thio)-5-methyl-6-phenylpyrimidin-4(3H)-one (CCG-205381). Compound N4 dissolved in dimethylformamide (5 mL) and stirred at room temperature. Cesium carbonate (0.55 g, 1.67 mmol) was added followed by allyl bromide (0.22 g, 1.82 mmol). After 3 hours the mixture was diluted with 40 mL of water and extracted twice with ethyl acetate. The combined extracts were washed with water then saturated brine and dried over MgSO$_4$. The solvent was removed under reduced pressure and the residue chromatographed on silica gel, eluting with Hxa/EtOAc 6:1 to afford the product (0.052 g) as a clear, pale yellow oil; mass spec ES+ m/z=317, 339 (m+1, m+23); $^1$H NMR (500 MHz, DMSO) δ 7.61 (d, 2H), 7.50-7.46 (m, 3H), 5.97-5.83 (m, 1H), 5.24 (d, 1H), 5.17 (d, 1H), 4.66 (d, 2H), 3.60 (t, 2H), 3.38 (t, 2H), 3.25 (s, 3H), 2.03 (s, 3H).

Example Compound 54

4-(Allyloxy)-2-((2-methoxyethyl)thio)-5-methyl-6-phenylpyrimidine (CCG-205382) The impure chromatography fractions from Example 53 were combined and stripped of solvent. The residue was chromatographed on silica gel eluting with Hxa/EtOAc 12:1 to afford the product (0.02 g) as a cloudy colorless oil; mass spec ES+ m/z=317, 339 (m+1, m+23); $^1$H NMR (500 MHz, dmso) δ 7.58 (dd, 2H), 7.52-7.49 (m, 3H), 6.22-6.01 (m, 1H), 5.43 (dd, 1H), 5.30 (d, 1H), 4.94 (d, 2H), 3.61 (t, 2H), 3.31-3.21 (m, 5H), 2.11 (s, 3H).

Example Compound 55

4-(2-Methoxyethoxy)-2-((2-methoxyethyl)thio)-5-methyl-6-phenylpyrimidine (CCG-205361). 2-Bromoethyl methyl ether (0.35 g, 2.4 mmol) was added in one portion to a stirred mixture of cesium carbonate (0.82 g, 2.5 mmol) and 5-methyl-6-phenyl-2-thioxo-2,3-dihydropyrimidin-4(1H)-one (0.5 g, 2.29 mmol) from Step 2 in dimethylformamide (5 mL) at room temperature. The mixture was heated to 70° C. for 4½ hours then allowed to cool. Additional cesium carbonate (0.82 g, 2.5 mmol) was added followed by bromoethyl methyl ether (0.4 g, 2.9 mmol). After 18 hours the mixture was poured into water and stirred, then extracted with dichloromethane three times. The combined extracts were washed with water then saturated brine, and dried over MgSO$_4$. The solvent was removed under reduced pressure leaving a crude mixture containing the title compound and its N-alkylated isomer. Chromatography on silica gel, eluting first with 2 column volumes of Hxa/EtOAc 4:1 then with Hxa/EtOAc 3:1 afforded the product (0.4 g) as a clear colorless oil; mass spec ES+ m/z=335, 357 (m+1, m+23); $^1$H NMR (500 MHz, dmso) δ 7.58 (dd, 2H), 7.54-7.40 (m, 3H), 4.51 (t, 2H), 3.70 (t, 2H), 3.60 (t, 2H) 3.31 (s, 6H), 3.30 (m, 2H), 2.09 (s, 3H).

Example Compound 56

Ethyl 3-allyl-2-((2-methoxyethyl)thio)-4-oxo-4,6-dihydro-3H-spiro[benzo[h]quinazoline-5,4'-piperidine]-1'-carboxylate (CCG-206233): 30 mg (82%); $^1$H NMR (CDCl$_3$/TMS) δ 8.08 (dd, 1H, J=7.5 & 1.4 Hz), 7.32-7.40 (m, 2H), 7.23 (d, 1H, J=7.0 Hz), 5.91 (m, 1H), 5.28 (m, 2H), 4.68 (d, 2H, J=5.2 Hz), 4.13 (q, 2H, J=7.1 Hz), 3.98-4.08 (m, 2H), 3.76 (t, 2H, J=6.2 Hz), 3.54 (t, 2H, J=6.2 Hz), 3.42 (s, 3H), 2.98-3.18 (m, 4H), 2.9 (m, 1H), 2.7 (m, 1H), 1.43 (m, 2H) and 1.25 (t, 3H, J=7.1 Hz).

Example 4

This example describes treatment and prevention of infections caused by drug-resistant *Staphylococcus* including methicillin resistant *Staphylococcus aureus* (MRSA), *Pseudomonas aeruginosa*, and *E. coli*. Treatments for humans and animals (companion and agriculture) are applications. These compounds may also be used in agricultural animals to control infections and reduce the use of classical antibiotics that leads to resistant bacteria and the diminished efficacy for humans. Infections examined in this example include: traumatic wounds, skin ulcers, skin and substructure infections, pneumonia, urinary tract and abdominal infections, food poisoning and sepsis.

Figure 12:
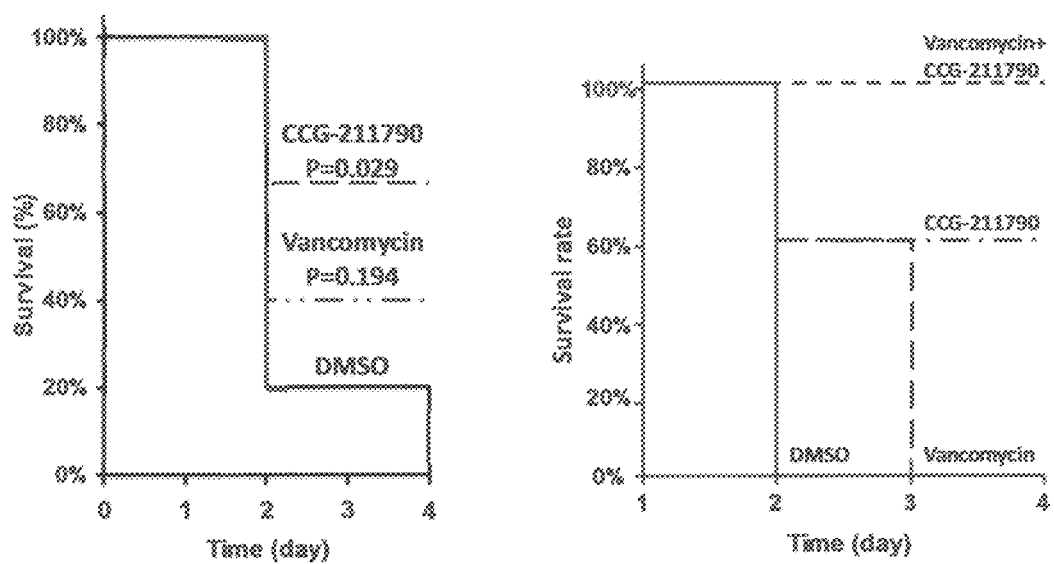
FIG. 12 shows the survival rate of mice intranasally infected with 10⁹ CFU *S. aureus* and treated with vancomycin alone, CCG-211790 alone, vancomycin and CCG-211790 in combination and DMSO.

*S. aureus* is one of the major causative agents of pneumonia. CCG-211790 was tested in a pneumonia model. Balb/C mice were intra-nasally infected with $10^7$ CFU *S. aureus* clinical strain NRS234 and treated with either 0.15 µmol CCG-211790 or DMSO two hours after infection. The mice were then treated with CCG-211790 or DMSO (control) twice a day after the day of infection for three days. Significant reduction of bacterial counts in both lungs and spleens were observed in mice treated with CCG-211790, compared with the control group treated with DMSO (FIGS. 11A and 11B), suggesting that the reduction of virulence enabled the host to exert better control of infection. Mice were also infected with higher dose of bacteria at $10^9$ CFU treated intraperitoneally (ip) with either 0.15 µmol CCG-211790, vancomycin, combination of CCG-21790 and vancomycin, or DMSO two hours after infection. The mice were then treated twice a day after the day of infection for three days. Significant protection of hosts was observed by monotherapy CCG-21790 (p=0.029) (FIG. 12A). A group of mice treated with a combination of vancomycin and CCG-211790 showed that the combination improved the survival rate (FIG. 12). These results demonstrate that CCG-211790 could inhibit *S. aureus* virulence in vivo alone and can enhance the potency and efficacy in combination with vancomycin.

Example 5

In this example, in vivo and in vitro efficacy for wound infection (against MRSA and *P. aeruginosa*) was investigated. Diabetic ulcer lesion is a major complication of people with diabetes and represents a form of chronic wounds. Bacteria can form biofilm in the lesions, which is recalcitrant to treatment. Therefore, diet induced obesity (DIO) mice were used as a model of obesity and insulin resistance diabetes to test the in vivo efficacy of CCG-211790 to fight wound infections.

Figure 13A:
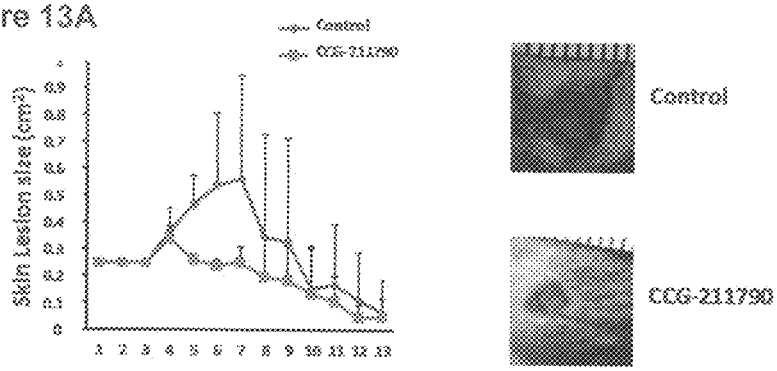
FIGS. 13A-13D show mitigation of wound infections by CCG-211790.
Figure 13B:
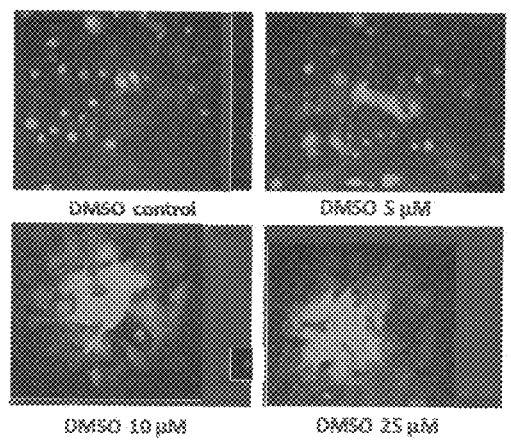

A skin punch wound was introduced to the DIO mice and infected with $10^8$ CFU MRSA. Mice were then treated locally at the wound site with ointment containing CCG-211790 (60 µg/wound) in an ointment (6% silica in cod liver oil) or ointment alone. The compound was able to reduce the skin lesion size in DIO mice (FIG. 13A), demonstrating that the compound could be used to treat wounds infected with MRSA both in healthy and diseased patients. Furthermore, CCG-211790 protected mouse fibroblast cells (CCL-1) from MRSA cytotoxicity in vitro (FIG. 13B).

Figure 13C:
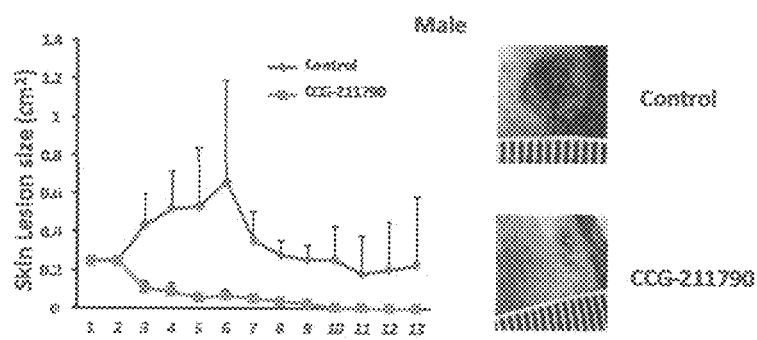
Figure 13D:
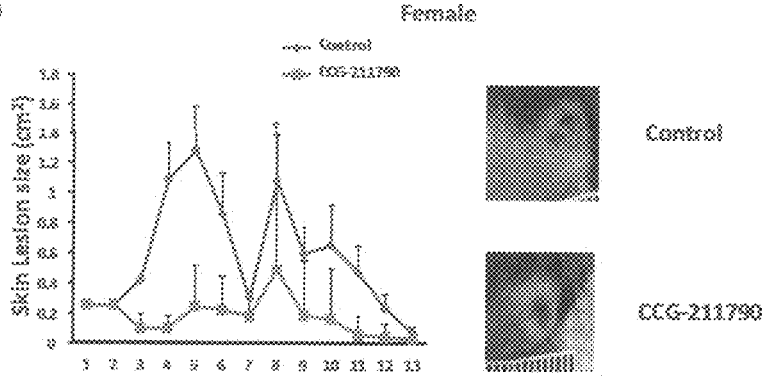

The compound was also tested in treating wounds infected with $10^8$ CFU *P. aeruginosa*. *P. aeruginosa* infection caused death in female DIO mice, indicating that *P. aeruginosa* can systemically spread from the wound infection site. Therefore, mice were treated by oral delivery of CCG-211790. Mice were also injected (ip) with vancomycin to decrease the chance of cross infection with *S. aureus*. 12 mg/kg CCG-211790 with 10 mg/kg vancomycin reduced mortality in female mice compared to vancomycin treatment alone (100% survival vs. 40% survival). Furthermore, skin lesion size was also reduced in both male and female DIO mice compared to control with only vancomycin treatment (FIGS. 13C & 13D).

Example 6

In this example, the effect of CCG-203592 on *S. aureus* gene expression was investigated. Real time RT-PCRs were performed at mid-logarithmic growth phase (ML), late logarithmic growth phase (LL) and stationary (S) phase.

Biofilm formation was used as a virulence marker in a microtiter plate-based phenotypic functional assay to rapidly test a large number of compounds. Biofilms are complex structures consisting of bacteria enveloped in extracellular polymeric matrix involved in a wide variety of infections. Many of the genes involved in biofilm formation are also critical virulence factors and make the bacteria harder to treat with antibiotics. Compounds CCG-203592 and CCG-205363 demonstrated strong inhibition of *S. aureus* biofilm formation with $IC_{50}$ in the low µM range without inhibiting bacterial growth. As shown in FIG. 2C, these compounds inhibited gene expression of a number of critical virulence factors, including genes that are important for *S. aureus* biofilm formation and structures, and key virulence factors such as protein A (SPA), α-toxin (Hla), sigma B and phenol soluble modulins (PSMs).

Figure 14A:
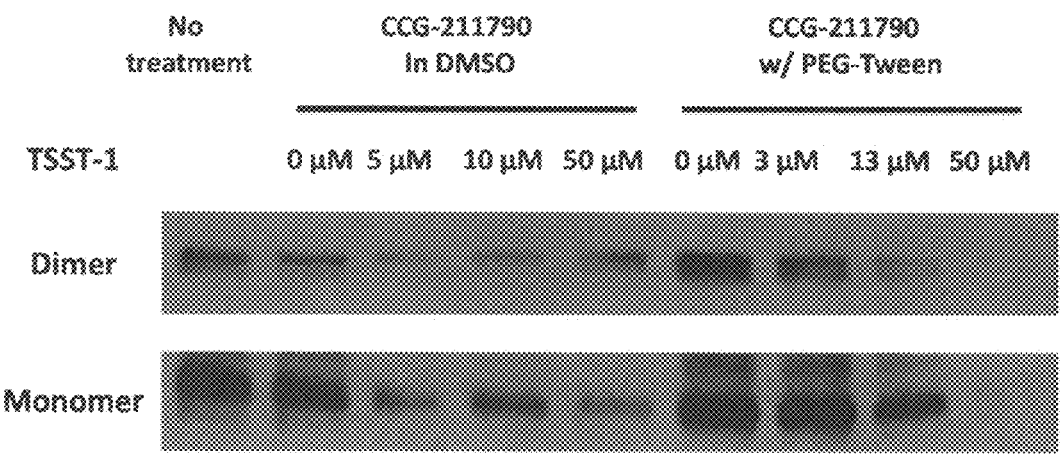
FIG. 14A shows the reduction in the production of TSST-1 in *S. aureus* by CCG-211790.
Figure 14B:
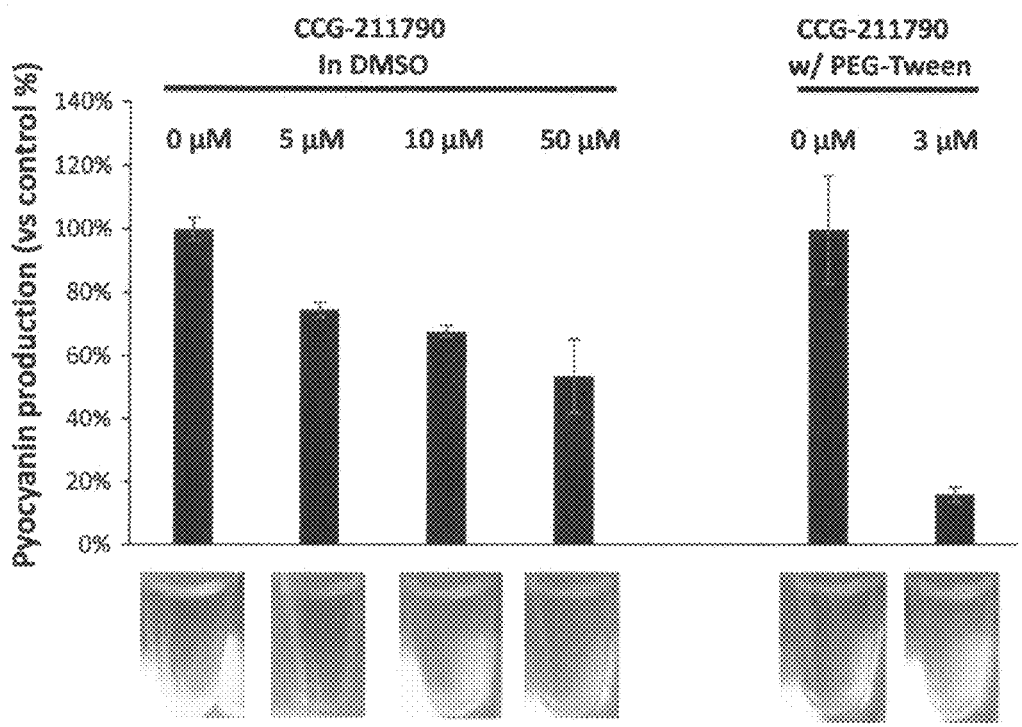
FIG. 14B shows the reduction in the production of pyocyanin in *P. aeruginosa* by CCG-211790.

The *S. aureus* virulence genes analyzed were SPA, α-toxin, sigma B, toxic shock syndrome toxin (TSST) (FIG. 14A), and PSM (FIG. 2C). These virulence factors play roles in helping to establish infection, evade the immune response, and some are associated with biofilm formation that contributes to bacterial virulence and reduced susceptibility to antibiotics. Compounds inhibited the production of α-toxin at the gene level measuring RNA (FIG. 2C) and at the functional level as demonstrated by cell cytotoxicity assay (FIG. 13B). The inhibition of *S. aureus* toxins, most notably α-toxin, agrees with its role in the pathogenesis of skin infections. This cytolytic pore-forming protein lyses human cells, including skin fibroblasts, keratinocytes, and immune cells, interferes with the innate and adaptive immune responses in skin infection models, and is involved in biofilm development on mucosal surfaces. *S. aureus* strains isolated from patients with skin infections displayed a higher a-toxin production than strains from healthy controls, and the amount of α-toxin produced correlated with disease severity. α-Toxin has been reported to play a significant role in lung tissue damage during murine staphylococcal pneumonia. Research has determined that virulence correlated with expression levels of α-toxin and that it may be a key virulence factor in lung infections. Biofilm and virulence factors are also involved in skin and pulmonary infections caused by the opportunistic pathogen, *P. aeruginosa*. Pyocyanin, a representative pigment produced by *P. aeruginosa*, dyes bacteria medium blue-green, and is contributes to lung destruction during chronic *P. aeruginosa* infection in patients with bronchiectasis and cystic fibrosis. Pyocyanin inhibits the ciliary beating of airway epithelial cells, and enhances superoxide production that damages lung tissue. The compounds disclosed herein inhibited skin infections by *P. aeruginosa* (FIGS. 13C & 3D) and blocked the production of pyocyanin (FIG. 14B).

These results demonstrate that the efficacy is in part is due to antivirulence mechanisms including reduction gene expression or proteins regulating toxin production, adhesion and colonization, biofilm formation, flagella for motility and attachment to human cells, bacterial secretory systems, cell-to-cell signaling pathways, gene regulatory pathways, and antibiotic resistance mechanisms, such as efflux pumps (multidrug resistance). The compounds disclosed herein down-regulated the mechanisms that bacteria use to evade the immune system thus disarming pathogens, allowing the body's innate and adaptive immune response to more efficiently remove the bacteria.

Example 7

In this example, compounds were analyzed for effect on *Escherichia coli* (*E. coli*) virulence.

*E. coli* is a major pathogen that can cause urinary tract infections (75-95% of all cases), food poisoning (Shiga toxin-producing STEC *E. coli*), hemorrhagic colitis (HC) and hemolytic uremic syndrome (HUS); serotype O157:H7. Urinary tract infections caused by *E. coli* have been show to depend on the flagella that allows the organism to be mobile and attach to urinary tract epithelial cells and establish an infection in the bladder (cystitis). Furthermore, flagella contribute to dissemination throughout the urinary tract contributing to the serious infection of the kidneys (pyelonephritis).

Figure 15A:
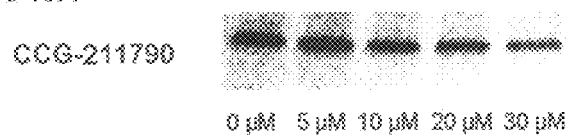
FIGS. 15A and 15B show CCG-211790 (NV001) inhibited *E. coli* virulence.
Figure 15B:
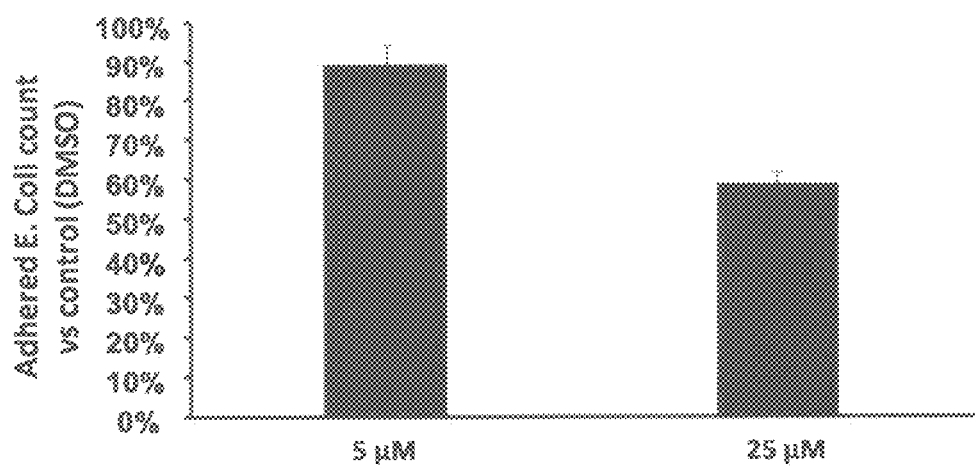

CCG-211790 (NV001) and a number of structural analogs inhibited the expression of the flagellin gene (fliC) (FIG. 15A) and also the bacterial adhesion to human epithelial cells (Caco2) (FIG. 15B). As summarized in Table 5, the effect of compounds on *E. coli* flagellin expression was also tested by incubating compounds (5 and 25 µM) with *E. coli* for 6 hours, flagellin expression in supernatant (IVG-00601, 607) or cell pellet (IVG-00608-006014) was examined by western and quantified. The results demonstrated that the compounds are useful for treating urinary tract infections alone or in combination with antibiotics to shorten the time to recovery and prevent progression to pyelonephritis.

TABLE 5

*E. coli* flagellin production inhibition.

| Analog No. | Analog Structure | Relative Level vs. Control | |
|---|---|---|---|
| | | 5 µM | 25 µM |
| IVG-00601-00A01 | | 0.85319 | 0.039587 |
| IVG-00607-00A01 | | 0.634281 | 0.275169 |
| IVG-00608-00A01 | | 0.827619 | 0.488782 |
| IVG-00609-00A01 | | 0.754417 | 0.152685 |
| IVG-00610-00A01 | | 0.316378 | 0.088293 |

TABLE 5-continued

*E. coli* flagellin production inhibition.

| Analog No. | Analog Structure | Relative Level vs. Control | |
| --- | --- | --- | --- |
| | | 5 μM | 25 μM |
| IVG-00611-00A01 | | 0.195729 | 0.135654 |
| IVG-00612-00A01 | | 0.181084 | 0.129484 |
| IVG-00613-00A01 | | 0.342318 | 0.139367 |
| IVG-00614-00A01 | | 0.243843 | 0.261527 |
| NV001 | | 0.56907 | 0.153615 |
| IV501 | | 0.36186 | 0.475361 |
| DMSO | | 1 | 1 |

While *E. coli* is the most common bacteria associated with UTIs, *Pseudomonas aeruginosa* and *Staphylococcus aureus* are also commonly found in UTIs associated with biofilm formation. The ability these compounds to prevent the expression of virulence factors allows these agents to disarm or counteract the pathogenic mechanism of a number of very important pathogenic bacteria.

Example 8

In this example, compounds were analyzed as combination therapies with antibiotics and tested for efficacy against antibiotic resistant bacteria.

Examples of combination antibiotics included amoxicillin, vancomycin, clindamycin, tetracycline, and erythromycin. These represent major classes of antibiotics many of which have lost their efficacies due to the emergence of resistance in important bacteria that cause diseases.

Figure 16A:
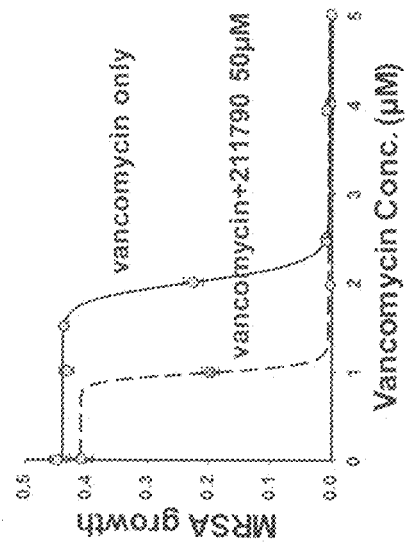
FIGS. 16A-16F show antivirulence compound enhanced antibiotic potency against MRSA.
Figure 16B:
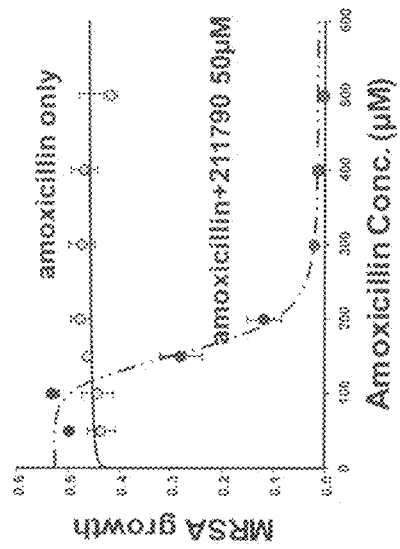
Figure 16C:
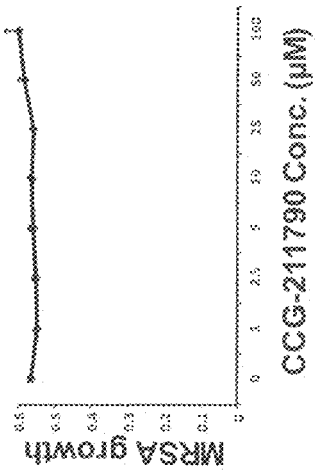
Figure 16D:
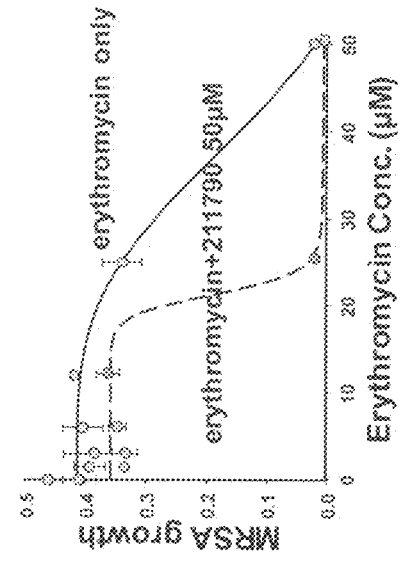
Figure 16E:
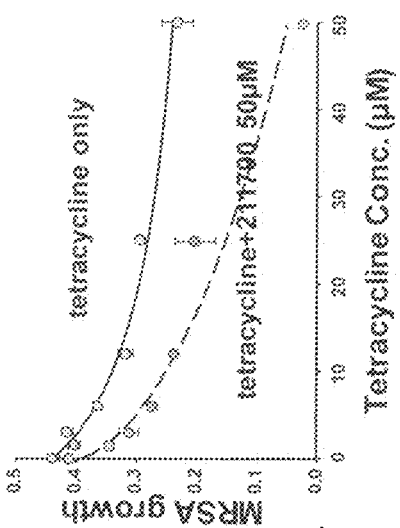
Figure 16F:
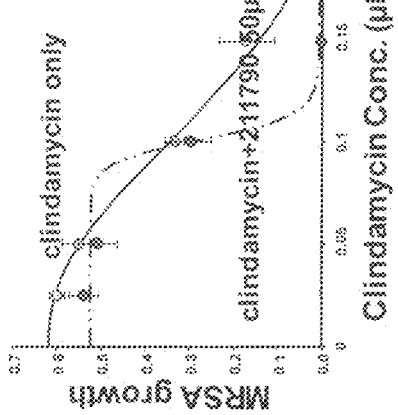
Figure 17A:
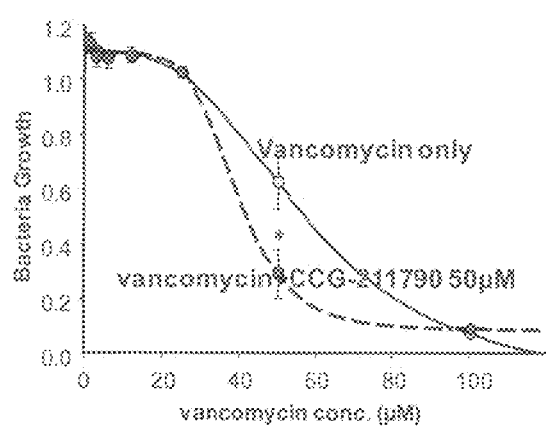
FIGS. 17A and 17B show enhancement of antibiotic potency by CCG-211790.
Figure 17B:
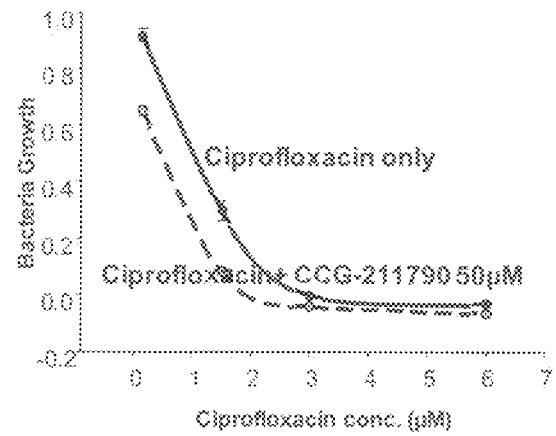

The response of MRSA to amoxicillin, vancomycin, clindamycin, tetracycline and erythromycin in the presence of compound CCG-211790 was tested. CCG-211790 enhanced the antibiotic potency against MRSA (FIG. 16), including reducing resistance to amoxicillin. These results further confirm the increase in vivo efficacy of the combined treatment of the compound with vancomycin than either the compound or vancomycin alone (FIG. 12). The synergy was not related to any effect of compound on bacteria growth, since compound CCG-211790 had little to no effect on bacteria growth (FIG. 16A). Similarly, CCG-211790 enhanced the potency of vancomycin against *Acinetobacter baumannii* and ciprofloxacin potency against *P. aeruginosa* (FIG. 17).

These results demonstrate that the disclosed compounds have efficacy as monotherapy and improved the efficacy of classical antibiotics in combination therapies. The compounds in combination therapies can reduce the dose and time course for more efficient use of current antibiotics that are becoming ineffective. Surprisingly and unexpectedly, treatment of antibiotic resistance bacteria (MRSA) with the compounds in combination with the antibiotic to which the bacteria had resistance resulted in reduced growth of the antibiotic resistant bacteria. The combination therapy (fixed dose forms or separate drugs) with the compounds and standard antibiotics appeared to "rescue" utility of currently ineffective antibiotics in the antibiotic resistant bacteria (FIG. 16). Combination therapy above also demonstrated improved efficacy with Vancomycin (FIG. 12). Thus, the compounds disclosed herein are useful in methods of treating bacterial infections having antibiotic resistant bacteria when formulated as combination therapies with the antibiotic to which the bacteria are resistant.

Example 9

Synthetic Scheme for IVG-00608-00A01-IVG-00614-00A01

Figure 18:
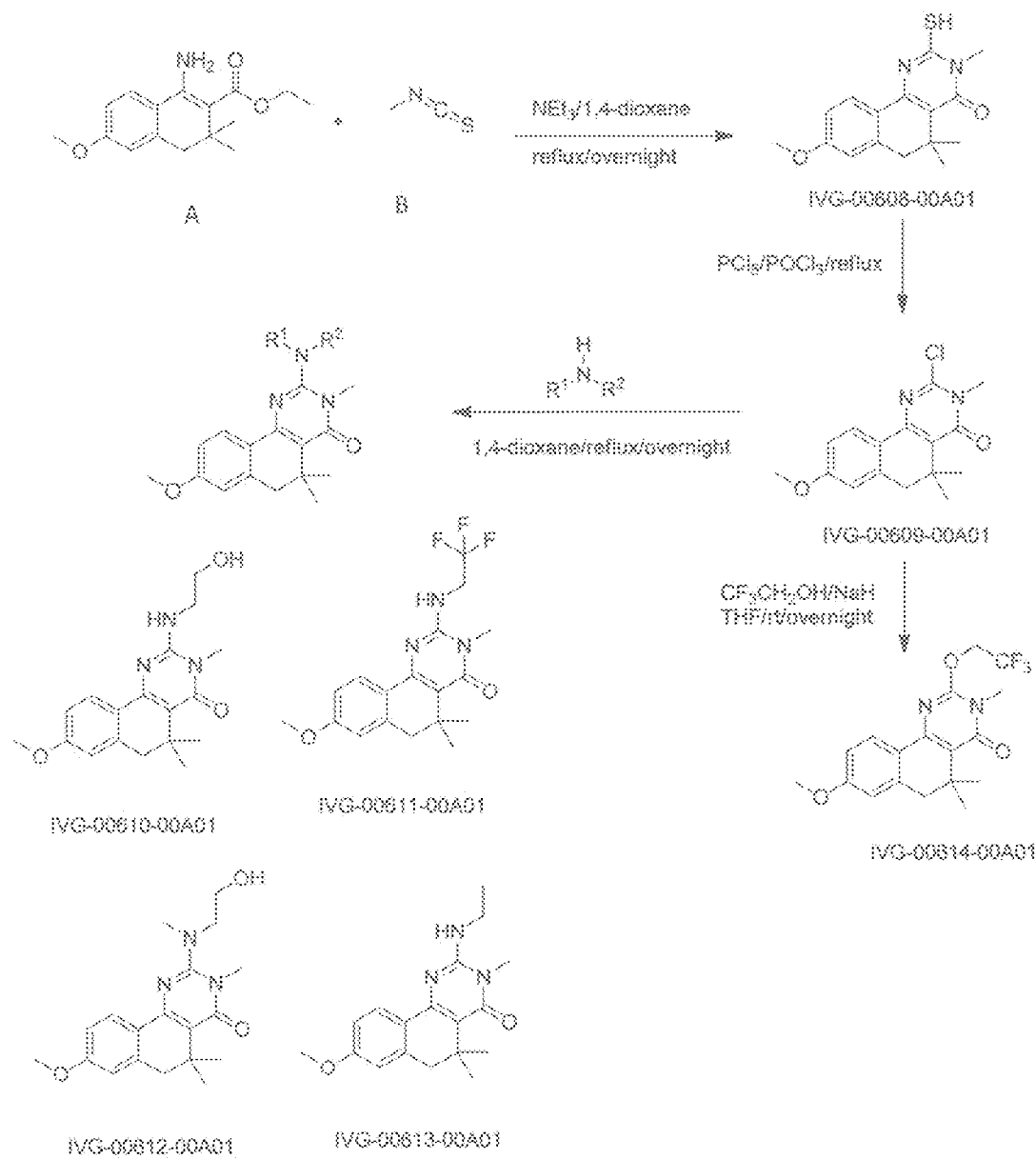
FIG. 18 is a scheme showing the synthesis of the IVG series of compounds of formula (V).

The synthesis of the series of compounds started with compound A as the starting material (FIG. 18). When compound A was treated with compound B (1.5 equiv) in 1,4-dioxane in the presence of 1 eq of NEt3 at reflux, compound IVG-00608-00A01 was obtained. Then by reaction of IVG-00608-00A01 with 1.8 equiv of PCl$_5$ in POCl$_3$ as solvent at reflux afforded IVG-00609-00A01. By treatment of IVG-00609-00A01 with 10 equiv of one of the chosen amines in 1,4-dioxane at reflux overnight (for IVG-00611-00A01) afforded IVG-00610-00A01, IVG-00611-00A01, IVG-00612-00A01, and IVG-00613-00A01. The synthesis of IVG-00614-00A01 was accomplished by the reaction of in situ generated sodium salt of 2,2,2-trifluoroethanol with IVG-00609-00A01 in THF at room temperature.

Example 10

Exemplary Topical Cream Formulations with compound 211790 (interchangeably used herein with "NV001")

In this Example, more details of exemplary topical compositions with one of the suitable compounds, 211790 (NV001), in cream emulsion are listed in the following tables, with Table 6a being blank (0%) cream formulation, Table 6b 0.3% cream formulation, Table 6c 1% cream formulation, Table 6d 3% cream formulation.

TABLE 6a

Blank cream (0% drug loading)

| Excipient | Percent/% |
| --- | --- |
| Isopropyl myristate (IPM) | 10.5 |
| Mineral oil | 42.2 |
| BRIJ ® 58 | 6.2 |
| Stearyl alcohol | 3.6 |
| Cetyl alcohol | 3.6 |
| Xanthan gum | 0.2 |
| Water | 33.4 |
| Citric acid | 0.07 |
| Sodium citrate | 0.23 |
| NV001 | 0 |
| Total | 100% |

TABLE 6b 0.3% cream (0.3% drug loading)

| Excipient | Percent/% |
| --- | --- |
| Isopropyl myristate (IPM) | 10.5 |
| Mineral oil | 42.2 |
| Brij ® 58 | 6.2 |
| Stearyl alcohol | 3.6 |
| Cetyl alcohol | 3.6 |
| Xanthan gum | 0.2 |
| Water | 33.1 |
| Citric acid | 0.07 |
| Sodium citrate | 0.23 |
| NV001 | 0.3 |
| Total | 100% |

TABLE 6c

1% cream (1% drug loading)

| Excipient | Percent/% |
| --- | --- |
| Isopropyl myristate (IPM) | 10.5 |
| Mineral oil | 42.2 |
| BRIJ ® 58 | 6.2 |
| Stearyl alcohol | 3.6 |
| Cetyl alcohol | 3.6 |
| Xanthan gum | 0.2 |
| Water | 32.4 |
| Citric acid | 0.07 |
| Sodium citrate | 0.23 |
| NV001 | 1.0 |
| Total | 100% |

TABLE 6d

3% cream (3% drug loading)

| Excipient | Percent/% |
|---|---|
| Isopropyl myristate (IPM) | 10.5 |
| Mineral oil | 41.2 |
| BRIJ ® 58 | 6.2 |
| Stearyl alcohol | 3.6 |
| Cetyl alcohol | 3.6 |
| Xanthan gum | 0.2 |
| Water | 31.4 |
| Citric acid | 0.07 |
| Sodium citrate | 0.23 |
| NV001 | 3.0 |
| Total | 100% |

The drug release testing and performance parameters of the above-mentioned cream formulations were conducted using the standard Franz Chamber testing method for drug release and penetration and performance analysis. The general Franz Chamber Protocol is included as following: 1) Prepare receiving medium (2% SDS in Ethanol/Water (40/60)), and degas the medium by ultrasound bath; 2) Turn on the machine and adjust the temperature at 32° C.; 3) Saturate the membrane (Polycarbonate (0.4 μm)) in receiving medium for 30 min; 4) Apply membrane on the dosage wafer, and apply spatula to spread out cream on the membrane (200 mg for 0.3% and 1.0%, 100 mg for 3.0%); 5) Add medium into receptor and place the wafer and membrane on the receptor without bubbles; 6) Use clamp to fix the donor and receptor; 7) Seal the donor chamber using sealing film; 8) Set the stirring speed at 600 rpm, and start the machine; 9) Stop stirring 30 s before sampling, take 300 μL medium at 0.5 h, 1 h, 2 h, 3 h, 4 h and 6 h, and refill with fresh medium.

Figure 19:
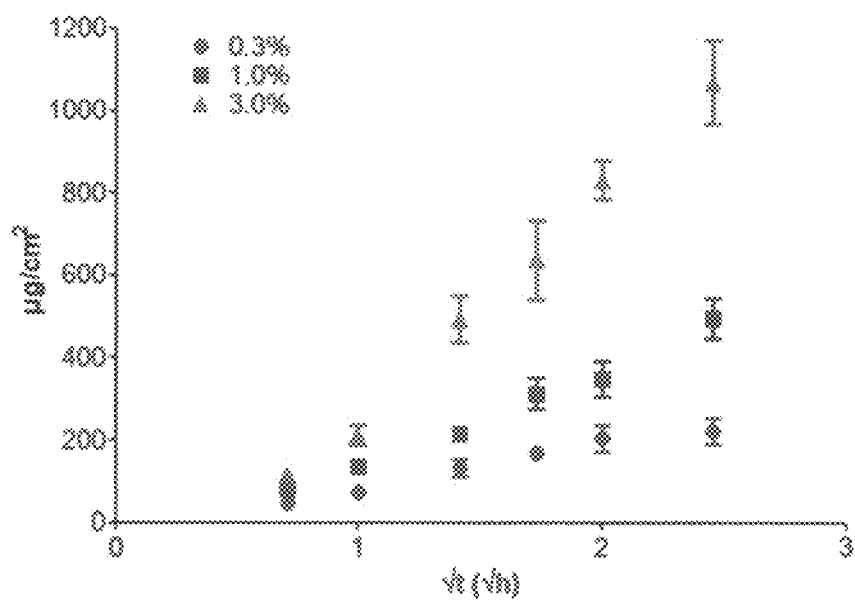
FIG. 19 is a drug release graph for three different concentrations of 211790 (NV001) in topical cream formulations.

The drug release parameters are included in Table 7. The drug release curves are illustrated in FIG. 19.

TABLE 7

Drug Release Parameters for Various Cream Formulations with 211790 (NV001)

| Drug loading | Release rate (μg/cm$^2$/√h) | Cumulative release rate (%) | Cumulative release (μg) | Final concentration (μg/mL) | $R^2$ |
|---|---|---|---|---|---|
| 0.3% | 107 ± 21 | 38 ± 7 | 251 ± 35 | 16 ± 2 | 0.9398 |
| 1.0% | 233 ± 18 | 27 ± 4 | 559 ± 55 | 36 ± 4 | 0.9637 |
| 3.0% | 562 ± 53.0 | 39 ± 3 | 1209 ± 116 | 77 ± 7 | 0.9899 |

Quality Target Product Profile of the NV001 Cream were also tested and summarized in Table 8, whereas the stability data is included in Table 9.

TABLE 8

Quality Target Product Profile

| QTPP Elements | | Target | Justification |
|---|---|---|---|
| | Dosage form | Cream | Match indication |
| | Dosage design | O/W emulsion cream with NV001 dissolved and dispersed in the cream base | |
| | Route of administration | Topical | |
| | Dosage strength | 0.3%, 1.0% or 3.0% w/w | To be determined by animal test |
| | Stability | No less than 24-month expiration dating period | Match the shelf life of similar products |
| Drug product quality attributes | Appearance | White smooth cream with dissolved and dispersed NV001 | Patient acceptability |
| | pH | 5.0~5.4 | No irritation |
| | Viscosity | 12000~14000 cP | Needed for applicability and drug release control |
| | Identification | Positive for NV001 | Needed for clinical effectiveness |
| | Assay | 90~110% of label claim | |
| | Content Uniformity | Top, middle and bottom of three containers. Nice assay values should be within 90.0%~110.0% label claim and RSD ≤5%. | Needed for clinical effectiveness |
| | Impurities | Any individual unknown: NMT 0.2%; total impurities: NMT 0.5% | Needed for safety |
| | Release behavior | Release rate within 10~30% in 6 h | To describe performance characteristics as a part of quality control procedure and rationalization for scale-up and post approval changes |
| | Preservatives content | Methyl paraben: 80.0~110.0% label claim; | Needed for ensuring antimicrobial effectiveness |
| | Microbial limits | Meet USP <61> | Needed for safety |
| | Residual solvents | Meet UPS <467> | Needed for safety |
| | Container closure system | Container closure system qualified as suitable for this drug product | Needed to achieve the target shelf-life and to ensure stability during shipping and storage |
| | Package integrity | No failure | Needed for stability, clinical effectiveness and safety |

TABLE 9

Stability

| Time | Viscosity/cP | pH |
|---|---|---|
| Day 1 | 13483 ± 104 | 5.14 |

| | Temperature | | | |
|---|---|---|---|---|
| | 25° C. | 40° C. | 25° C. | 40° C. |
| Day 14 | 17200 ± 312 | 15167 ± 1841 | 5.14 | 5.19 |
| Month 1 | 13783 ± 896 | 16600 ± 656 | 5.33 | 5.06 |
| Month 3 | 13170 ± 442 | 18683 ± 925 | 5.24 | 5.32 |
| Month 6 | 12383 ± 275 | 10667 ± 493 | 5.35 | 5.19 |
| Deceased by | 8% | 21% | | |

Example 11

In this Example, open wound infections (methicillin resistant *Staphylococcus aureus* (MRSA), *Pseudomonas aeruginosa*) were treated with a topical cream formulation.

As demonstrated above, CCG211790 (NV001) exhibited antivirulence activity and controlled biofilm wound infections with accelerated healing when delivered topically in oil or ip (see, FIG. 13A-13D). A topical formulation was developed as a pharmaceutical emulsion. The in vivo efficacy of the topical formulation was analyzed in the open wound infection mouse model in normal mice.

In this Example, open wound infections (methicillin resistant *Staphylococcus aureus* (MRSA), *Pseudomonas aeruginosa*) were treated with a topical cream formulation of compound NV001 (CCG-211790) at different concentrations.

Briefly, skin punches (0.5 cm×0.5 cm) were introduced in mice and inoculated with *P. aeruginosa* (POA1) biofilm (6.8×10⁷ CFU) for two days, then treated with topical cream formulation daily. Wound size was significantly decreased at day 3 (FIG. 20A) in drug treated groups (p<0.05, n=4 or 6, Day3 vs Day 0), and at day 8 (FIG. 20B) between control and 1% formulation, which performed better than 0.3 or 3.0% NV001.

Similarly, skin punches (0.5 cm×0.5 cm) were introduced in mice and inoculated with MRSA (NRS234) biofilm (6.8×10⁸ CFU) for two days, then treated with topical formulation daily. Wound size was significantly decreased at day 3 (FIG. 21A) in drug treated groups (p<0.05, n=10, vs Day 0). The 1% formulation performed better than 0.3 or 3.0% NV001 but efficacy was not distinguishable on day 8 (FIG. 21B) due to the variability in this study. Dosing schedules are being evaluated for further efficacy studies as are additional, more robust wound models for MRSA, *Pseudomonas aeruginosa*, and other bacterial pathogens.

Example 12

In this Example, surgical site infections (Shiga toxin producing *Escherichia coli* (STEC *E. coli*) were treated with a IP formulation of compound NV001 (CCG-211790)(10% DMSO, 10% Tween 80, 80% saline).

A deep skin incision was made and inoculated with 5×10⁶ CFU *E. coli* STEC O157:H7. *E. coli* is one of the most common causative agents of surgical site infections. Mice were treated (ip) with either vehicle control, 10 mg/kg NV001 twice a day. At day 4 post-infection, NV001 reduced the mortality compared to vehicle control (55.6% survival vs. 22.2% survival).

Figure 22:
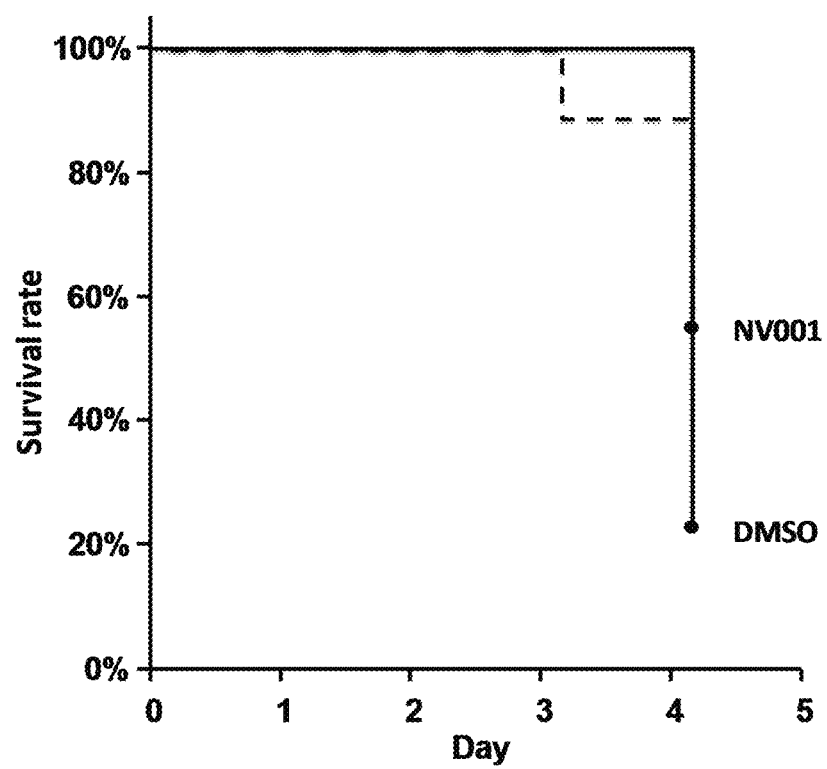
FIG. 22 is a graph depicting NV001 improved infection symptoms and survival in STEC *E. coli* infections.

As shown in FIG. 22, NV001 improved infection symptoms and survival in STEC *E. coli* infections.

Example 13

In this Example, open wound infections (*Acinetobacter baumannii*) were treated with a topical formulation of compound NV001 (CCG-211790).

Figure 23:
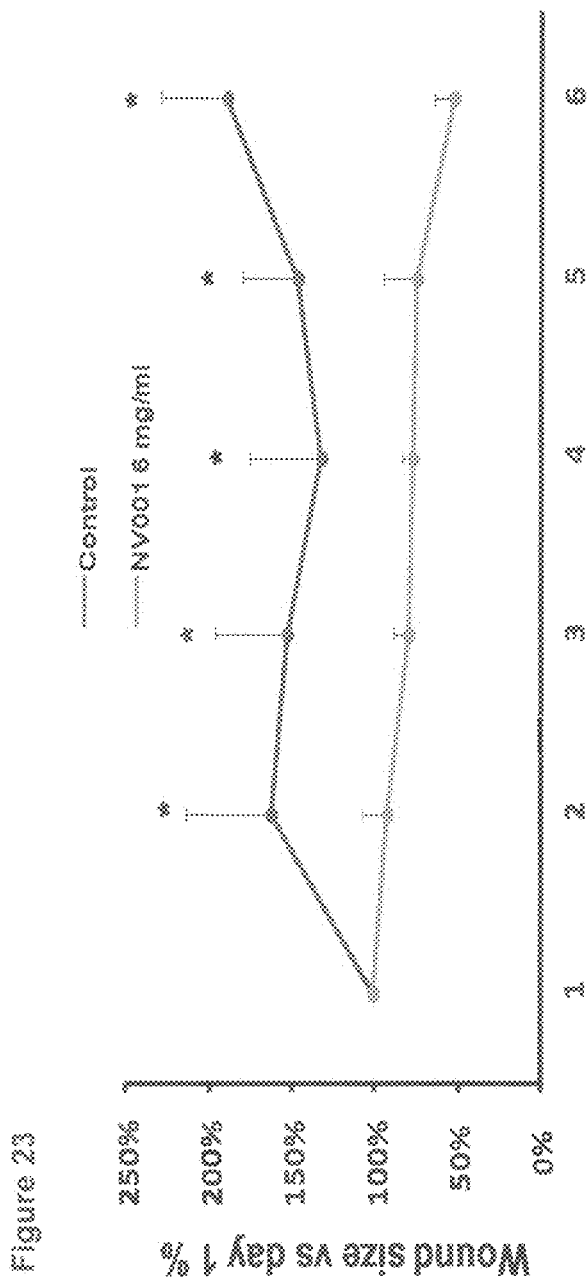
FIG. 23 is a graph depicting reduced *A. baumannii* infected wound lesion size in wounds treated with topical NV001.

A topical formulation (6 mg/ml in Polyehylene glycol; PEG) was tested for its in vivo efficacy on the open wound infection mouse model. Briefly, skin punches (0.5 cm×0.5 cm) were introduced in mice and inoculated with *A. baumannii* (AYE) biofilm (4.5×10⁶ CFU) for 1 day, then treated with 100 µl topical formulation daily. As shown in FIG. 23, wound size was significantly decreased from day 2 to day 6 in treated animals.

Together these data support that an antivirulence agent such as CCG-211790, which does not directly kill bacteria but disarms the bacteria, has a protective effect in a number of animal models of wound infections. The antibacterial activity is seen against multiple bacteria (Gram-positive and Gram-negative) when administered either locally or systemically. A pharmaceutical emulsion has been prepared and has the potential to be developed as a topical cream to fight bacterial infections, including antibiotic resistant strains as a monotherapy or in combination with existing antibiotics.

All publications and patents mentioned in the above specification are herein incorporated by reference. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the relevant fields are intended to be within the scope of the following claims.

What is claimed is:

1. A topical formulation for treating a bacterial infection comprising:
   a compound having the structure of Formula V

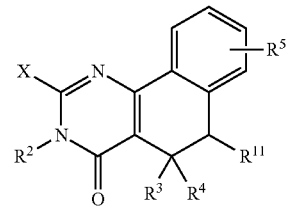

(V)

wherein X is SR¹, NH₂, NHR¹, NR¹R, OH, OR¹, or Cl; wherein R and R¹ are, independently, H, a C1-C8 alkyl or alkenyl or cycloalkyl, optionally substituted with F, CN, OR⁶, NR⁶₂, COR⁶, CO₂R⁶, CONHR⁶, aryl or heteroaryl, wherein one or more alkyl carbons may be replaced by O; R² is H or a C1 alkyl; R³ and R⁴ are, independently, a C1-C8 alkyl; R⁵ is C1-C6 alkyl, CN, OR⁶, NR⁶₂, COR⁶, CO₂R⁶, CONHR⁶, aryl, heteroaryl, SO₂R⁶, NHCOR⁶, SO₂NHR⁶, or OCOR⁶; R⁶ is H, C1-C6 alkyl, C0-C3 alkyl-aryl, or C0-C3 alkyl-heteroaryl, all optionally substituted; and R¹¹ is H or a C1 alkyl; and
   a base comprising a hydrocarbon base, an oil, and combinations thereof.

2. The topical formulation of claim 1, wherein the compound is selected from the group consisting of:

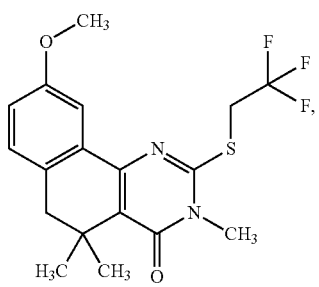

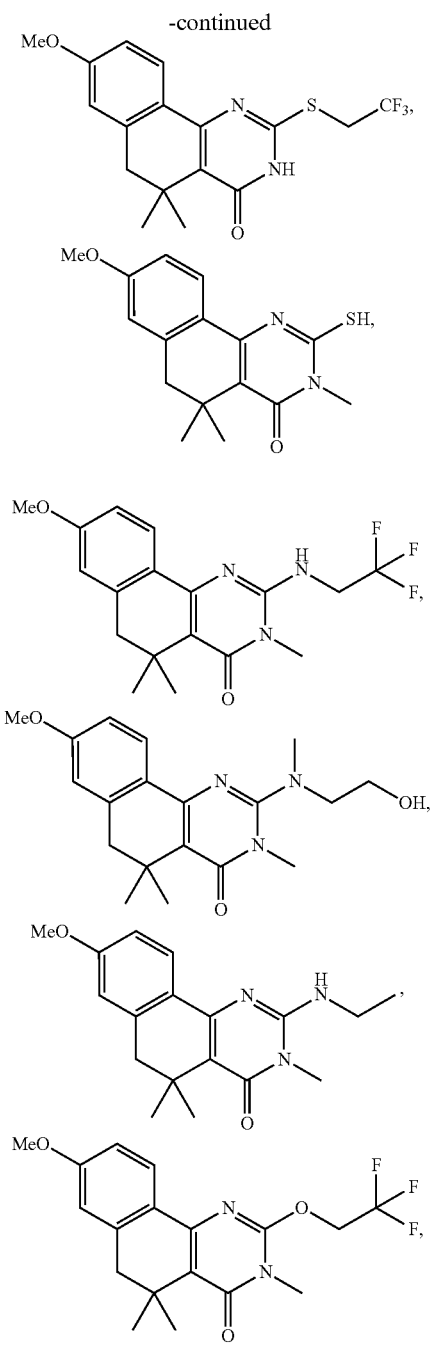

and combinations thereof.

3. The topical formulation of claim 1 comprising about 0.05 wt. % to about 5.0 wt. % of the compound having the structure of Formula V.

4. The topical formulation of claim 1, wherein the hydrocarbon base comprises liquid paraffin, white petrolatum, a wax, esters of fatty alcohols, saturated fatty acids, oleic acid, olive oil, starch glycerin, purified lanolin, cetyl alcohol, glyceryl monostearate, methylparaben, propylparaben, glycol ethers, gelation hydrocarbon, polyethylene glycol, polyoxyl 40 stearate, polysorbates, hydrophilic ointment base, ceresine, white ointment base, absorptive ointment base, Macrogol ointment base, simple ointment base, beeswax, wool fat, mineral oil, and combinations thereof.

5. The topical formulation of claim 1, wherein the oil comprises a vegetable oil.

6. A topical formulation for treating a bacterial infection comprising:
a compound having the structure of Formula V

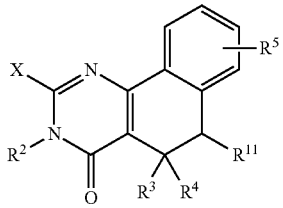

(V)

wherein X is $SR^1$, $NH_2$, $NHR^1$, $NR^1R$, OH, $OR^1$, or Cl; wherein R, $R^1$ and $R^2$ are, independently, H, a C1-C8 alkyl or alkenyl or cycloalkyl, optionally substituted with F, CN, $OR^6$, $NR^6{}_2$, $COR^6$, $CO_2R^6$, $CONHR^6$, aryl or heteroaryl, wherein one or more alkyl carbons may be replaced by O; $R^3$ and $R^4$ are, independently, a C1-C8 alkyl; $R^5$ is H, C1-C6 alkyl, CN, $OR^6$, $NR^6{}_2$, $COR^6$, $CO_2R^6$, $CONHR^6$, aryl, heteroaryl, $SO_2R^6$, $NHCOR^6$, $SO_2NHR^6$, or $OCOR^6$; $R^6$ is H, C1-C6 alkyl, C0-C3 alkyl-aryl, or C0-C3 alkyl-heteroaryl, all optionally substituted; and $R^{11}$ is H or a C1 alkyl; and a base comprising a vegetable oil,
wherein the formulation is a topical formulation.

7. The topical formulation of claim 6, wherein the compound is selected from the group consisting of:

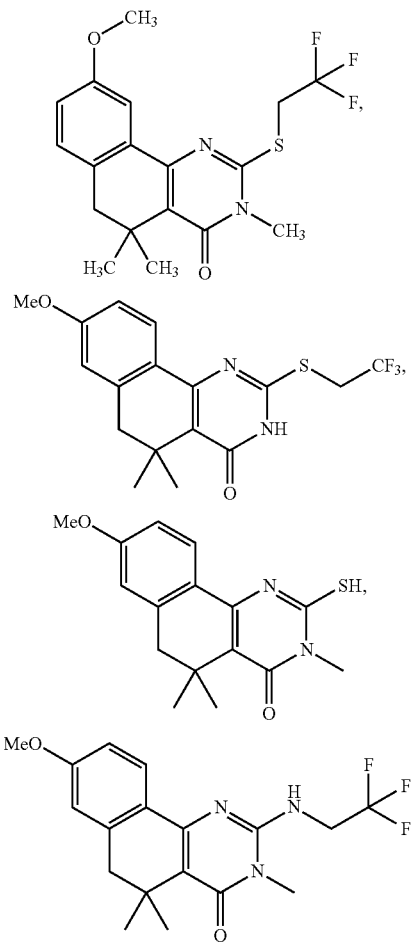

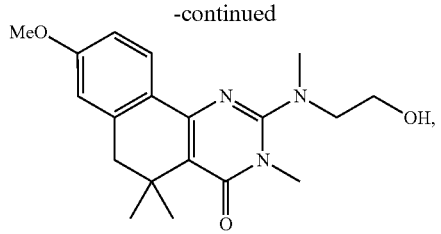
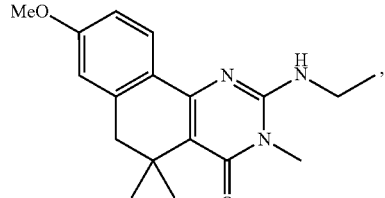
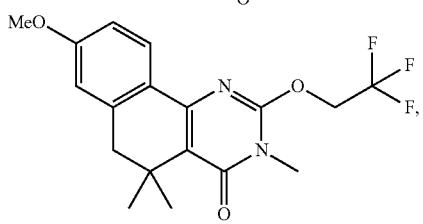
and combinations thereof.
8. The topical formulation of claim 6 comprising about 0.05 wt. % to about 5.0 wt. % of the compound having the structure of Formula V.
* * * * *